US008460895B2

(12) United States Patent
Eisenkraetzer et al.

(10) Patent No.: US 8,460,895 B2
(45) Date of Patent: Jun. 11, 2013

(54) METHOD FOR PRODUCING RECOMBINANT PROTEINS WITH A CONSTANT CONTENT OF $pCO_2$ IN THE MEDIUM

(75) Inventors: Detlef Eisenkraetzer, Iffeldorf (DE); Jochen Gaetgens, Juelich (DE); Alexander Jockwer, Muenchen (DE); Christian Klinger, Benediktbeurn (DE); Thomas Noll, Beilefeld (DE); Barbara Bezdek-Sueess, Aesch (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 12/920,915

(22) PCT Filed: Mar. 11, 2009

(86) PCT No.: PCT/EP2009/001742
§ 371 (c)(1),
(2), (4) Date: Mar. 7, 2011

(87) PCT Pub. No.: WO2009/112250
PCT Pub. Date: Sep. 17, 2009

(65) Prior Publication Data
US 2011/0159539 A1    Jun. 30, 2011

(30) Foreign Application Priority Data

Mar. 12, 2008   (DE) .......................... 10 2008 013 899

(51) Int. Cl.
*C12P 21/06* (2006.01)
(52) U.S. Cl.
USPC ........................................................ 435/69.1
(58) Field of Classification Search
None
See application file for complete search history.

(56) References Cited

U.S. PATENT DOCUMENTS 6,706,524 B2 *  3/2004  Wagner et al. ................ 435/325
2002/0052046 A1  5/2002  Wagner et al.

FOREIGN PATENT DOCUMENTS
WO    WO 2005/035748    4/2005

OTHER PUBLICATIONS

Bollati-Fogolin, "Expression of yeast pyruvate carboxylase in hGM-CSF-producing cho cells," Animal Cell Technology: From Target to Market, Proceedings of the 17th ESACT Meeting, pp. 241-243 (2001).
Bollati-Fogolin et al., "Impact of temperature reduction and expression of yeast pyruvate carboxylase on hGM-CSF-producing CHO cells," Journal of Biotechnology, vol. 109, No. 1-2, pp. 179-191 (2004).
Dezengotita et al., "Effects of CO2 and osmolality on hybridoma cells: Growth, metabolism and monoclonal antibody production," Cytotechnology, vol. 28, No. 1-3, pp. 213-227 (1998).
Kim et al., "Functional expression of human pyruvate carboxylase for reduced lactic acid formation of Chinese hamster ovary cells," Applied Microbiology and Biotechnology, vol. 76, No. 3, pp. 659-665 (2007).
Kimura et al., "Effects of elevated pCO2 and/or osmolality on the growth and recombinant tPA production of CHO cells," Biotechnology and Bioengineering, vol. 52, No. 1, pp. 152-160 (1996).
Pattison et al., "Measurement and Control of Dissolved Carbon Dioxide in Mammalian Cell Culture Processes Using an in Situ Fiber Optic Chemical Sensor," Biotechnology Progress, American Institute of Chemical Engineers, vol. 16, pp. 769-774 (2000).
Takuma et al., "Dependence on glucose limitation of the pCO2 influences on CHO cell growth, metabolism and IgG production," Biotechnology and Engineering, vol. 97, No. 6, pp. 1479-1488 (2007).
Zhu et al., "Effects of elevated pCO2 and osmolality on growth of CHO cells and production of antibody-fusion protein B1: a case study," Biotechnology and Progress 2005, vol. 21, No. 1, pp. 70-77 (2005).

* cited by examiner

*Primary Examiner* — Nashaat Nashed
(74) *Attorney, Agent, or Firm* — Bryan Cave LLP

(57) ABSTRACT

A method for the recombinant production of a polypeptide in a eukaryotic host cell modified in the citrate cycle is described, wherein the method comprises cultivating the eukaryotic host cell in a suitable medium under conditions which allow the expression of the polypeptide, wherein the content of dissolved $CO_2$ ($pCO_2$) in the medium is maintained at a constant value in the range of 10% to 20%.

13 Claims, 36 Drawing Sheets

METHOD FOR PRODUCING RECOMBINANT PROTEINS WITH A CONSTANT CONTENT OF PCO₂ IN THE MEDIUM

CROSS-REFERENCE TO RELATED APPLICATIONS

This application is the National Stage of International Application No. PCT/EP2009/001742, filed Mar. 11, 2009, which claims benefit to German Application No. 10 2008 013 899.1 filed on Mar. 12, 2008. The contents of the applications cited above are incorporated by reference in their entirety.

FIELD OF THE INVENTION

Background of the Invention

The present invention relates to a method for the recombinant production of a polypeptide in a eukaryotic host cell modified in the citrate cycle, wherein the cell is cultured in a medium with a content of dissolved $CO_2$ ($pCO_2$) which is maintained at a constant value in the range of 10% to 20%.

The ton-scale production of therapeutic proteins for specific therapies implies new requirements regarding expression and production systems. The main expression systems used are, amongst others, animal cell culture systems. The capability of animal cells to correctly fold and post-translationally modify proteins is, above all, a requirement for clinical application in humans. At present, almost 70% of all recombinant proteins are produced in animal cells in the pharmaceutical industry, most of these in CHO cells (*Chinese Hamster Ovary cells*) (Wurm, 2004). In comparison to microbiological systems, however, animal cell culture processes are characterized by longer generation time and lower final cell density in fermentations. Thus, product titres and space-time yields are lower than in microbiological processes. One possibility to compensate this disadvantage is metabolic engineering, i.e. controlling cell growth and minimizing apoptosis, programmed cell death, by genetic modification of the producing cells. In addition to genetic approaches, culture control strategies prove to be suitable optimization approaches the potential of which is often underestimated. It is, for example, possible to efficiently influence glycosylation, carbon metabolism, cell growth and cell death by using procedural monitoring and control strategies as well as the composition of culture media.

Thus, procedural development aims not only at the development of metabolically optimized cell lines but also at maximum exploitation of the potential of an existing cell line by optimum medium conditions and optimum process control. Apart from process parameters easily controllable such as oxygen content and temperature, more complex influence factors such as the content of dissolved carbon dioxide are taken into consideration for process control. In animal cell culture processes, $CO_2$ accumulates as final product in physically dissolved form and chemically dissociated as hydrogen-carbonate in aqueous culture media. Today, the development towards high cell density processes using animal cells in fed batch processes results, in conjunction with industrially used large-volume fermenters and hydrostatic pressures prevailing therein, i.e. in $CO_2$ partial pressures of 150-200 mm Hg which, consequently, are five times higher than the cell physiological values of 31-54 mm Hg. For example, for the provision of polypeptides (cytokines) produced by recombinant CHO cells, said cells were cultivated at 37° C. and 5% $CO_2$ (36 mm Hg $pCO_2$) in order to express the recombinant cytokines (U.S. Pat. No. 6,406,888B1). Fogolin et al., Journal of Biotechnology, 2004, 109, 179-191 shows that the genetic modified cell line CHO-K1-hGM-CSF expresses a recombinant yeast pyruvate carboxylase (PYC2) at 37° C. and 5% $CO_2$. The results of this study revealed that the expression of PYC2 and a reduced culture temperature have an additive effect on the cell specific productivity of the genetic modified cell line CHO-K1-hGM-CSF. Moreover, the effects of elevated $pCO_2$, osmolarity on the growth rate and specific human tPA production rate of a recombinant CHO cell line have been studied by Kimura and Miller, Biotechnology and Bioengineering, 1996, 52, 152-160. The media used for the experiments in this study contain 36 mm Hg $pCO_2$ (5% $CO_2$), 140, 195, 250 mm Hg $pCO_2$. However, these authors were of the opinion that the highest recombinant protein production rate can be achieved at 37° C. and 36 mm Hg $pCO_2$ (5% $CO_2$). Adverse effects on growth and productivity for hybridomas, NS0, CHO, BHK and insect cells have been reported for such high $pCO_2$ concentrations. In industrial large-scale fermenters, the accumulation of $CO_2$ is a restrictive factor. The desorption of dissolved $CO_2$ from the culture medium is a challenge for process engineering. Thus, the oxygen supply for the cultured cells has to be provided. Correcting variables for enhancing the oxygen transfer into the liquid phase are, for example, stirrer velocity and volumetric gas flow. However, these cannot be freely modified due to the partially cell disrupting shear stress and foaming.

BRIEF SUMMARY OF THE INVENTION

Thus, the technical problem underlying the present invention is to provide an optimized method for the recombinant production of proteins in eukaryotic host cells which overcomes the disadvantages described above, i.e. which throughout provides an optimum content of physically dissolved $CO_2$ in the medium.

The solution of this technical problem is provided by the embodiments characterized in the patent claims. The strategy leading to the present invention was based on the approach of controlling the set value of $pCO_2$ with simultaneous control of dissolved oxygen, pH value and overpressure in the reactor. This rational approach of the decoupled control of as many parameters as possible associated with $pCO_2$-related difficulties resulted in the surprising finding that the yield of recombinantly produced protein unexpectedly increased with a $pCO_2$ value maintained constant in the range of 10% to 20% of dissolved $CO_2$. Moreover, the control of the $pCO_2$ concentrations over the entire process of fermentation had a positive effect on culture viability and allowed for a prolonged stationary phase of high cell density. The respective results of the strategy resulting in the present invention when applied to the culture of animal cells are summarized below:

(a) $pCO_2$ Control

Based on an in situ sterilisable $pCO_2$ probe, a $pCO_2$ controller was developed for the studies which would meet industrial requirements and which was implemented successfully in development fermentation. With simultaneous, independent control of $pO_2$ and pH, this $pCO_2$ controller allows both, $pCO_2$-static culture and the generation of set value profiles for $pCO_2$. Applications in fed-batch mode and chemostat mode were established successfully on the 1 L and 10 L scale. The control range is 1.5-25.0% $pCO_2$. Thus, for the parameter $CO_2$, it is possible to deal with problems in industry on a small scale.

(b) Overpressure Control

An overpressure valve was developed for scales 1 L (up to 150 mbar overpressure) and 10 L (up to 1000 bar overpressure) which may be used independently from the controls for $pCO_2$, $pO_2$ and pH. Thus, problems of scale transmission in industrial bioprocesses (hydrostatic pressure, mixing time) can be represented on a small scale.

(c) pH Adjustment Agents

It was possible to show that the use of $Na_2CO_3$ for basic pH-adjustment results in increased viable cell density, prolonged viable culture period and, consequently, an increased space-time yield of a monoclonal antibody fusion protein in CHO cultures.

(d) Pressure-Controlled Sampling

The pressure-controlled sampling system allows the treatment of fermentation samples under bioreactor conditions (temperature, overpressure, $pCO_2$). For the first time, it is possible to study intracellular processes (e.g. intracellular pH) under bioprocess conditions.

(e) Effect of $pCO_2$ on the Intracellular pH Value of CHO Cells

The developed $pCO_2$ controller in combination with the pressure-controlled sampling allowed, for the first time, to observe the two-phase reaction of the intracellular pH-value with respect to changes in the $pCO_2$-value in the culture medium. Due to the dissociation equilibrium of $CO_2$ in aqueous solutions, the "chemical effect" as a direct effect causes a temporary change of the intracellular value (acidification of cytosol upon $pCO_2$ increase, alkalisation of cytosol upon $pCO_2$ neutralization). Contrary to this effect, there is a long-term and permanent reaction of the cell, the "physiological effect". For the first time, it was possible to observe this super-compensation by the deflection of the intracellular pH caused by the "chemical effect" in vitro and in situ (chemostat). The higher the $pCO_2$ gradient, the greater was the change of the intracellular pH.

(f) Findings Resulting from $pCO_2$-Controlled Bioprocesses with Recombinant CHO Cell Lines Static $pCO_2$ set value control increases process robustness.

Set value profiles of $pCO_2$ may be used in combination with cell physiology studies under bioprocess for a rational development of bioprocesses.

The $pCO_2$ levels are related directly to the intracellular pH value.

The intracellular pH value is related to cell cycle phase distribution.

An increasing gradient between the extracellular pH value and the intracellular pH value promotes formation and export of lactate.

Apart from the pH control of the culture medium, a $pCO_2$ control in pH-static bioprocesses may influence the lactate formation via the intracellular pH value, even in glucose-limited process conditions.

The recombinant cell line CHO-hGM-CSF-PYC2, which expresses the cytosolic pyruvate carboxylase, exhibited a $pCO_2$-sensitive energy metabolism. By increasing the controlled static $pCO_2$ level, it was possible to intensify the oxidative metabolism via an increase in the intracellular pH value in the course of culture. Furthermore, together with an increase in the statically controlled $pCO_2$ level, a prolonged viable culture period, efficient maintenance of the cell cycle in the G1 G0-phase, increased cell-specific productivity and an increase in the space-time yield by 100% was observed.

In statically controlled $pCO_2$ bioprocesses, a prolonged culture period has to be attributed, primarily, to the increased $pCO_2$ level, not to osmolality.

The optimum process values for controlled $pCO_2$ levels are found at 15% $pCO_2$.

The control of $pCO_2$ and, thus, the inhibition of the accumulation of $CO_2$ in the aqueous medium of bioprocesses allows, also in $HCO_3^-$-buffered media, a reliable online-determination of the respiratory quotient RQ in cell culture processes with exhaust gas analysis.

Undercut of the set value of $pCO_2$: PID 1 controls the opening width of the $CO_2$-MFC (0-5 $L \cdot h^{-1}$) installed in ratio-mode until the set value is reached. Exceedance of the set value for $pCO_2$: PID 1 initially closes $CO_2$-MFC and, upon continuous positive deviation of the set value, opens an additional $N_2$-MFC (0-15 $L \cdot h^{-1}$) via PID 2 (controller cascade).

Figure 2:
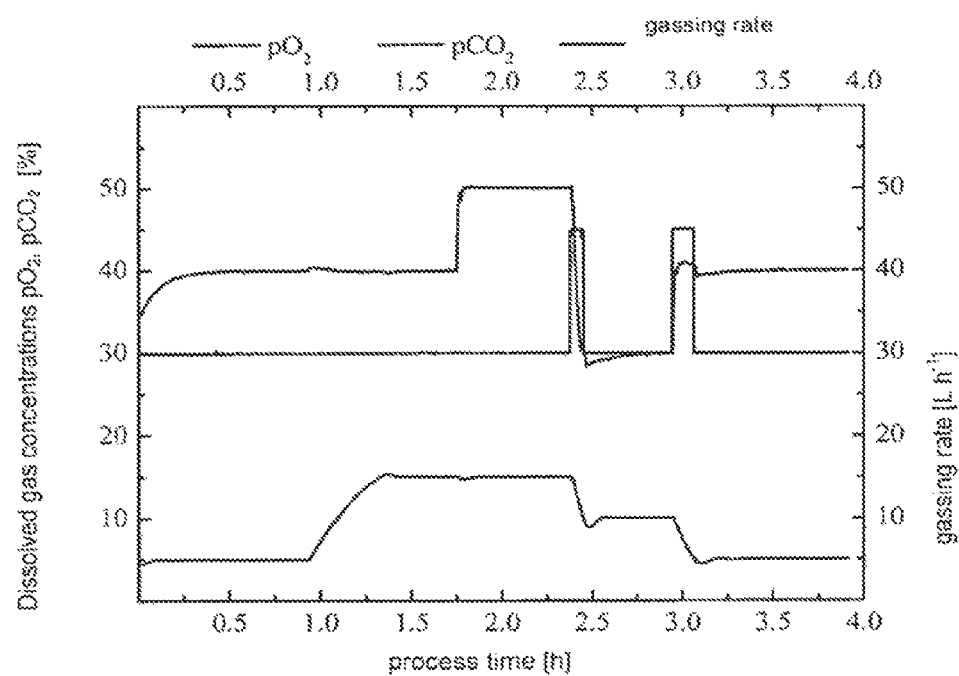

FIG. 2: Controlled gas concentrations of dissolved $pO_2$ and $pCO_2$ by ratio gassing and maximized $CO_2$-discharge due to increased gassing ratio in the 10 L stirring vessel reactor 50 mbar overpressure, 0.15 M NaCl, 37° C., 200 rpm, pH uncontrolled.

Figure 3:
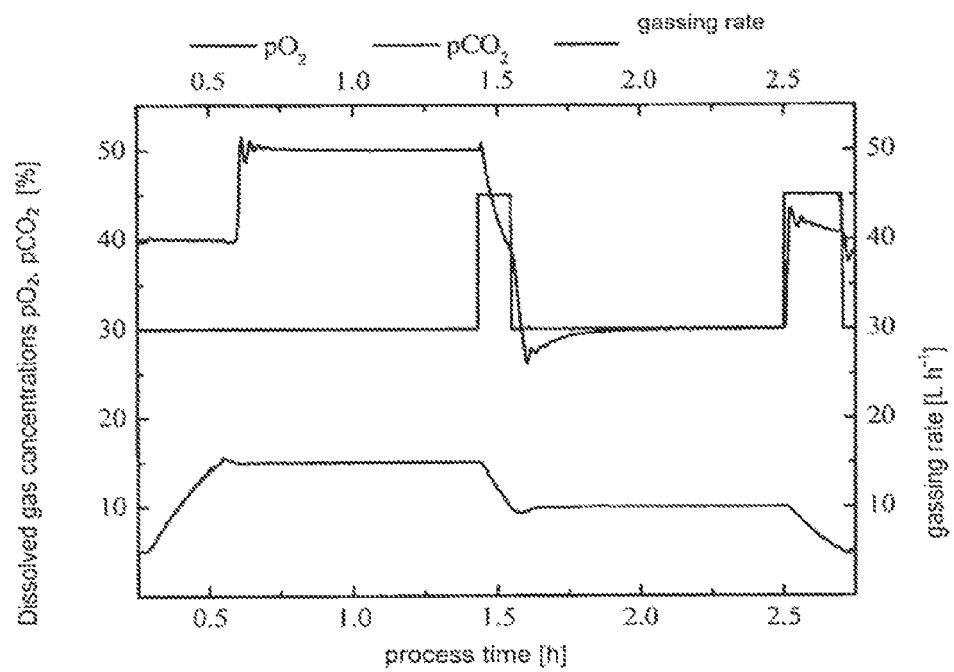

FIG. 3: Controlled gas concentrations of dissolved $pO_2$ and $pCO_2$ by ratio gassing and maximized $CO_2$-discharge due to increased gassing ratio in the 10 L stirring vessel reactor at 750 mbar overpressure 0.15 M NaCl, 37° C., 200 rpm, pH uncontrolled.

Figure 4:
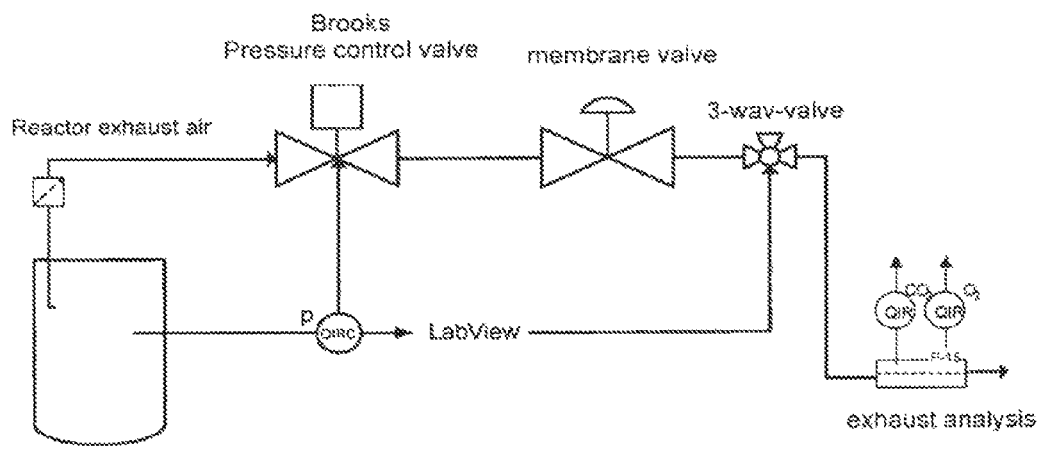

FIG. 4: Process scheme of the controlled overpressure system implemented in Biostat ES FIG. 5: Dynamic set value control of the control factors concentration of dissolved carbon dioxide $pCO_2$ (continuous line) and overpressure p (interrupted line) in the stirring vessel reactor (Biostat ES, B. Braun International; industrial production medium, standard fermentation parameters) by developed PID controller in process control software LabView.

Figure 6:
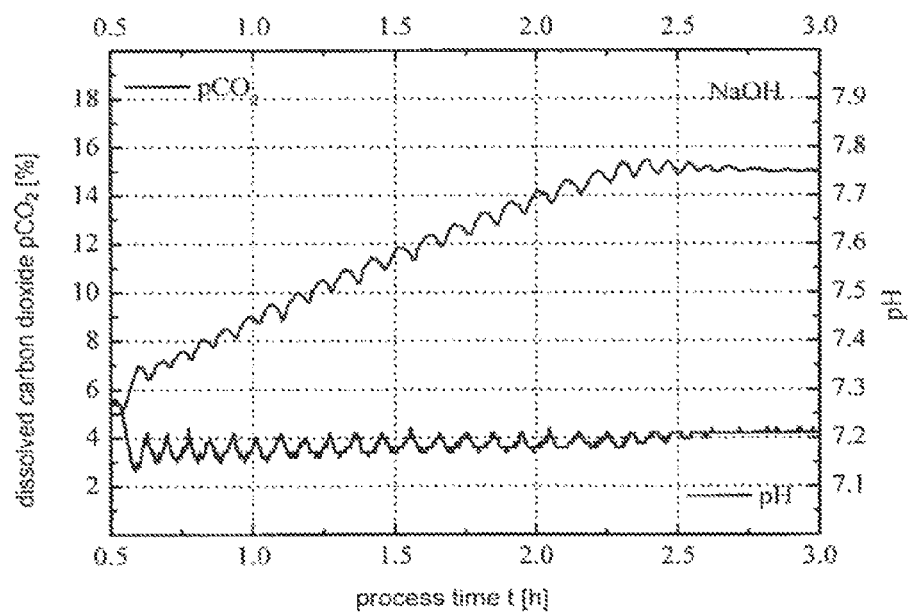

FIG. 6: Titration profile of the pH control to pH 7.2 with 1 M NaOH upon a set value surge from 5% $pCO_2$ to 15% $pCO_2$ Biostat ES, ratio gassing 30 $L \cdot h^{-1}$, 10 L working volume, aqueous buffer solution with $NaHCO_3/NaH_2PO_4/Na_2HPO_4$ analogous to industrial production medium, 37° C., 750 mbar overpressure.

Figure 7:
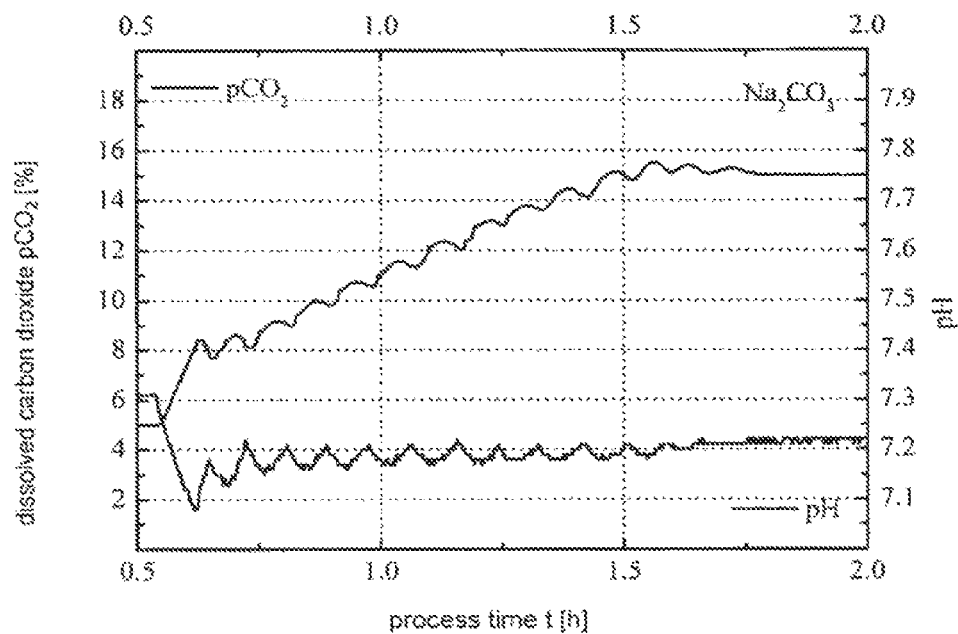

FIG. 7: Titration profile of the pH control to pH 7.2 with 1 M $Na_2CO_3$ upon a set value surge from 5% $pCO_2$ to 15% $pCO_2$ Biostat ES, ratio gassing 30 $L \cdot h^{-1}$, 10 L working volume, aqueous buffer solution with $NaHCO_3/NaH_2PO_4/Na_2HPO_4$ analogous to industrial production medium, 37° C., 750 mbar overpressure.

Figure 8:
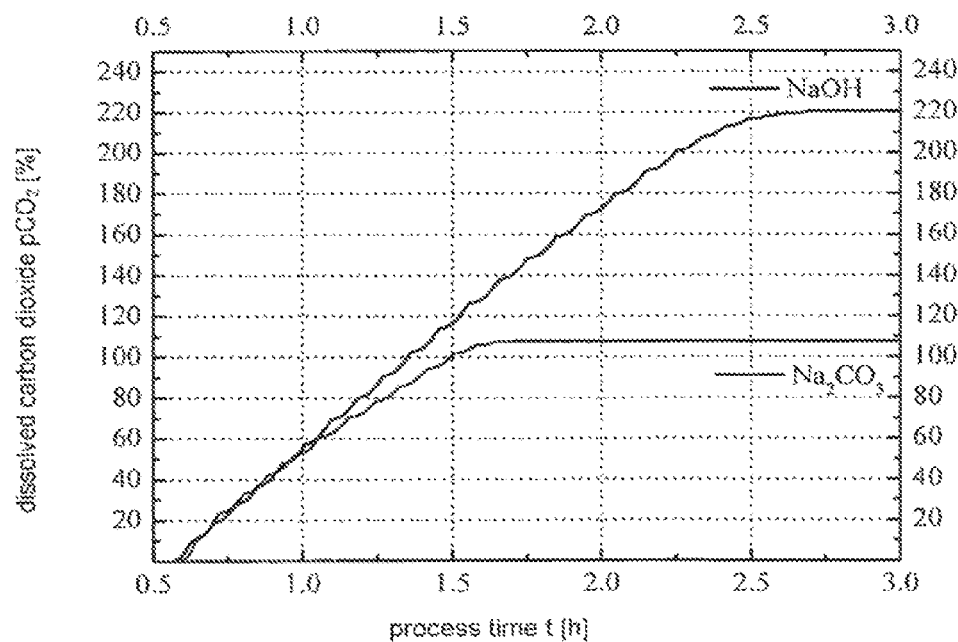

FIG. 8: Cumulative entry of the 1 M bases for pH control upon set value surge from 5% $pCO_2$ to 15% $pCO_2$ Biostat ES, ratio gassing 30 $L \cdot h^{-1}$, 10 L working volume, aqueous buffer solution with $NaHCO_3/NaH_2PO_4/Na_2HPO_4$ analogous to industrial production medium, 37° C., 750 mbar overpressure.

Figure 9:
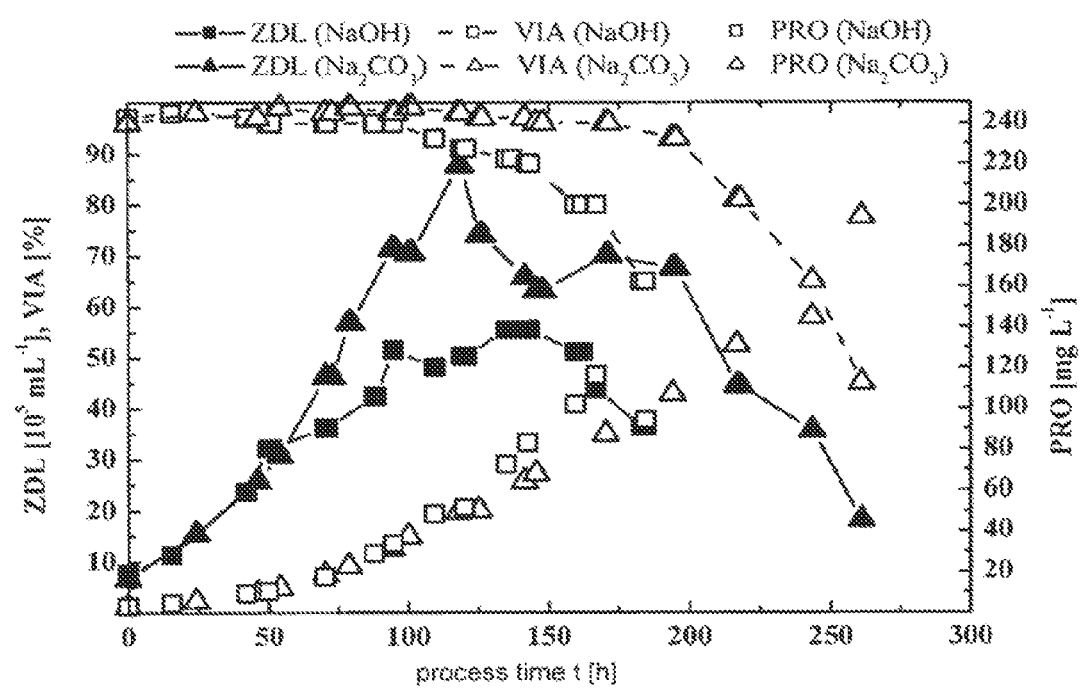

FIG. 9: Fed-batch fermentation with constant 5% (v/v) of $CO_2$ in the gassing mixture and pH-adjustment agent NaOH and $Na_2CO_3$, respectively Viable cell densities ZDL, viabilities VIA, product titre PRO (1 L, CHO-MUC1, 150 mbar overpressure, pH 7.2, 200 rpm, membrane gassing).

Figure 10:
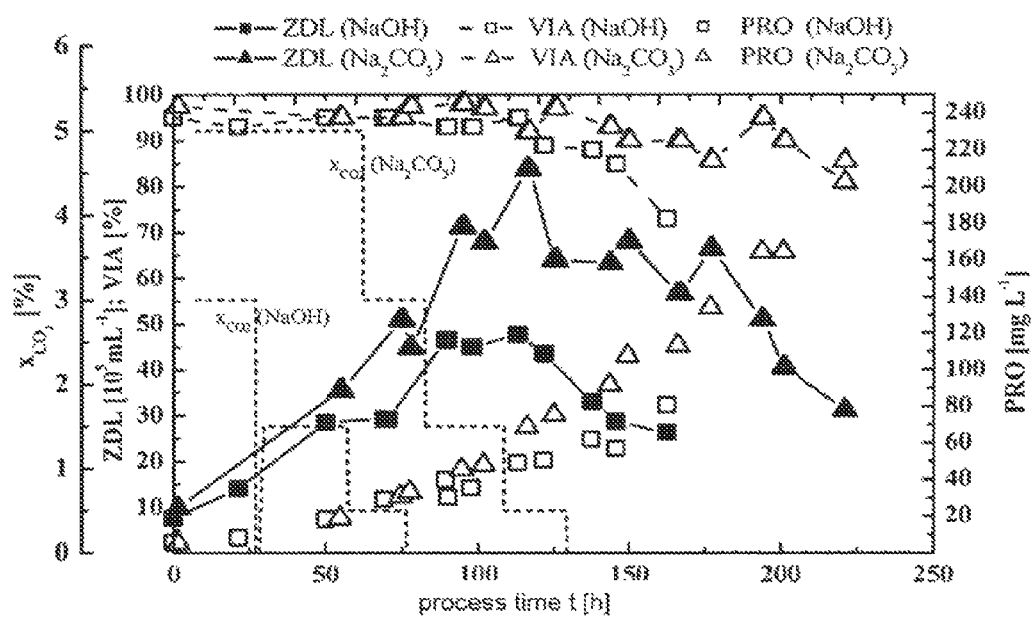

FIG. 10: Fed-batch fermentation with variable $CO_2$ ratios in the gassing mixture and pH adjustment agent NaOH and $Na_2CO_3$, respectively Viable cell densities ZDL, viabilities VIA, product titre PRO (1 L, CHO-MUC1, 150 mbar overpressure, pH 7.2, 200 rpm, membrane gassing; cf. also FIG. 11).

Figure 11:
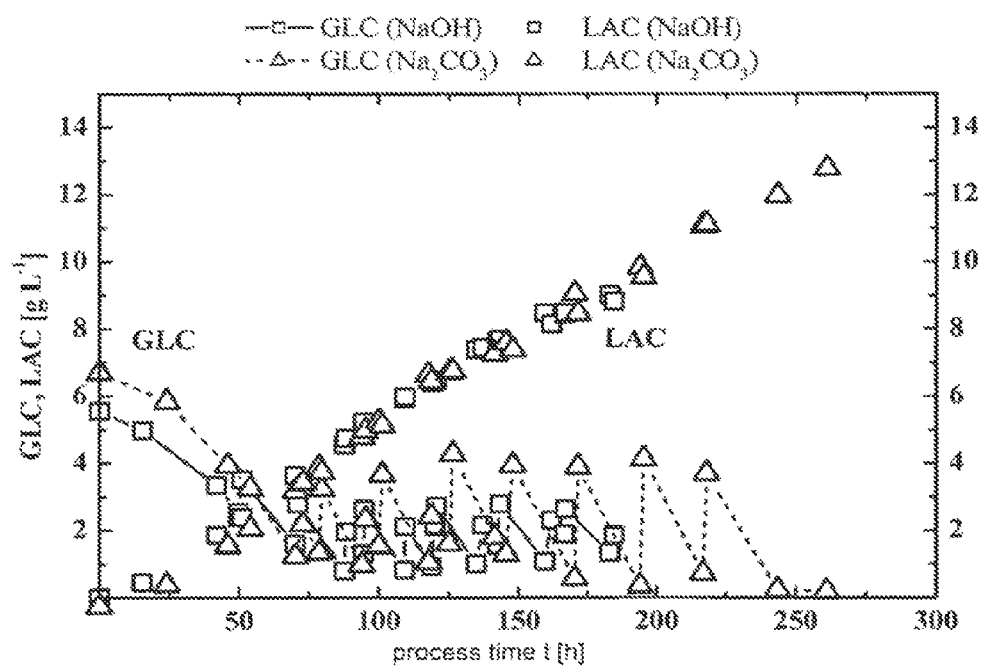

FIG. 11: Glucose and lactate concentrations in fed-batch cultivation of cell line CHO-MUC1 with pH-dependent variable $CO_2$ ratios in the gassing mixture 1 L, CHO-MUC1, 150 mbar overpressure, pH 7.2, 200 rpm, membrane gassing; cf. also FIG. 10.

Figure 12:
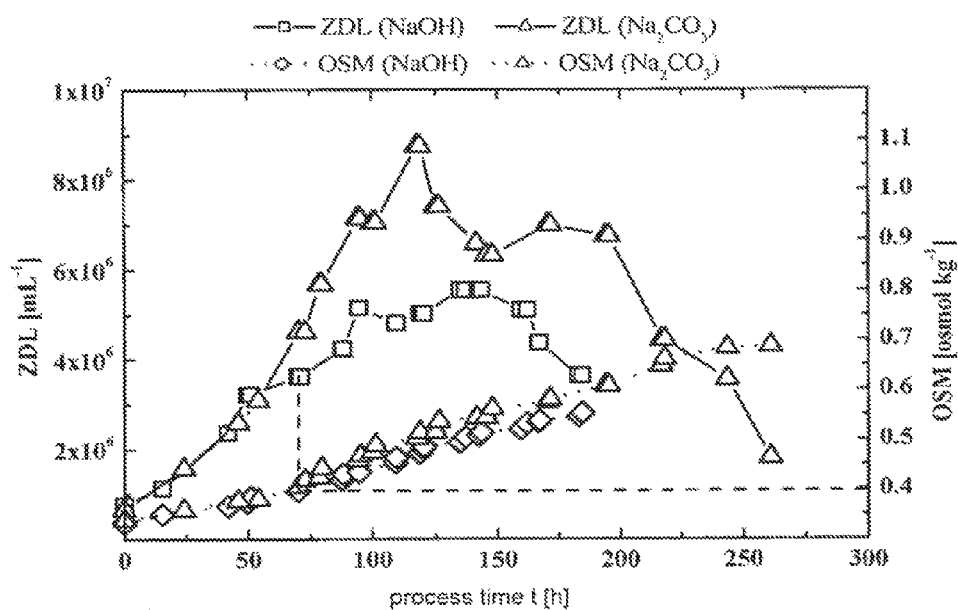

FIG. 12: Osmolalities OSM and viable cell densities ZDL of a fed-batch fermentation 1 L, CHO-MUC1, 150 mbar overpressure, pH 7.2, 200 rpm, membrane gassing.

Figure 13:
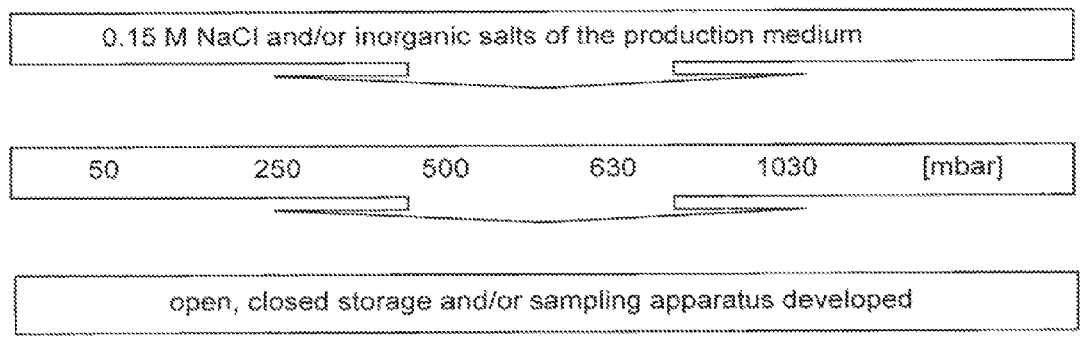

FIG. 13: Combined parameters for the characterization of the different sampling methods in Biostat ES (10 L)

open, closed storage: reaction tubes completely filled with medium (50 mL, Falcon); sampling apparatus developed: gas-tight and closed syringe without overpressure completely filled with medium.

Figure 14:
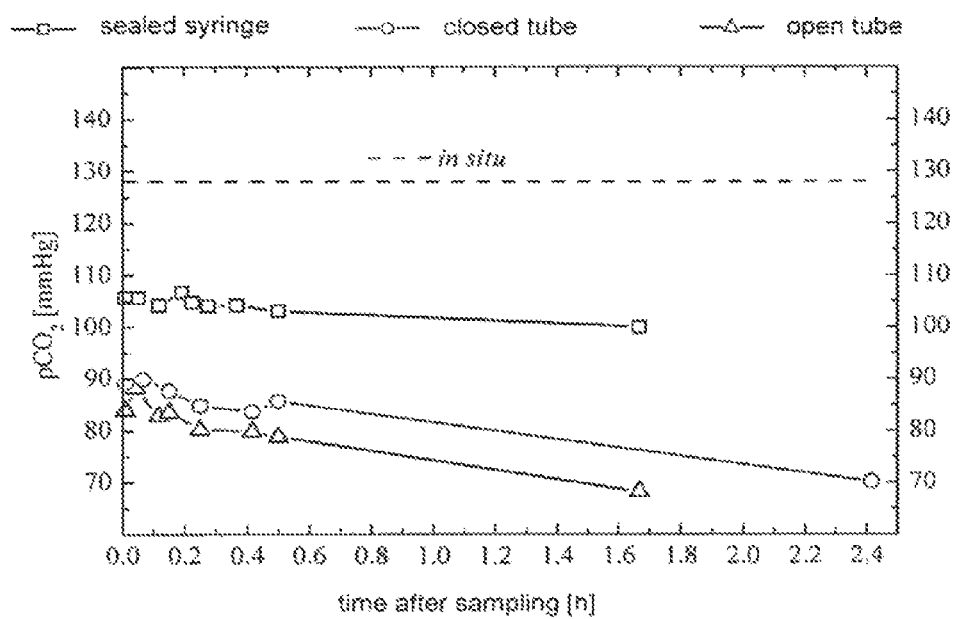

FIG. 14: $CO_2$ loss with different sampling types under atmospheric pressure in Biostat ES (0.15 M NaCl, 630 mbar overpressure), in situ and off-line $CO_2$ measurement YSI and AVL Compact 3; reaction tubes (50 ml, Falcon) completely filled with medium.

Figure 15:
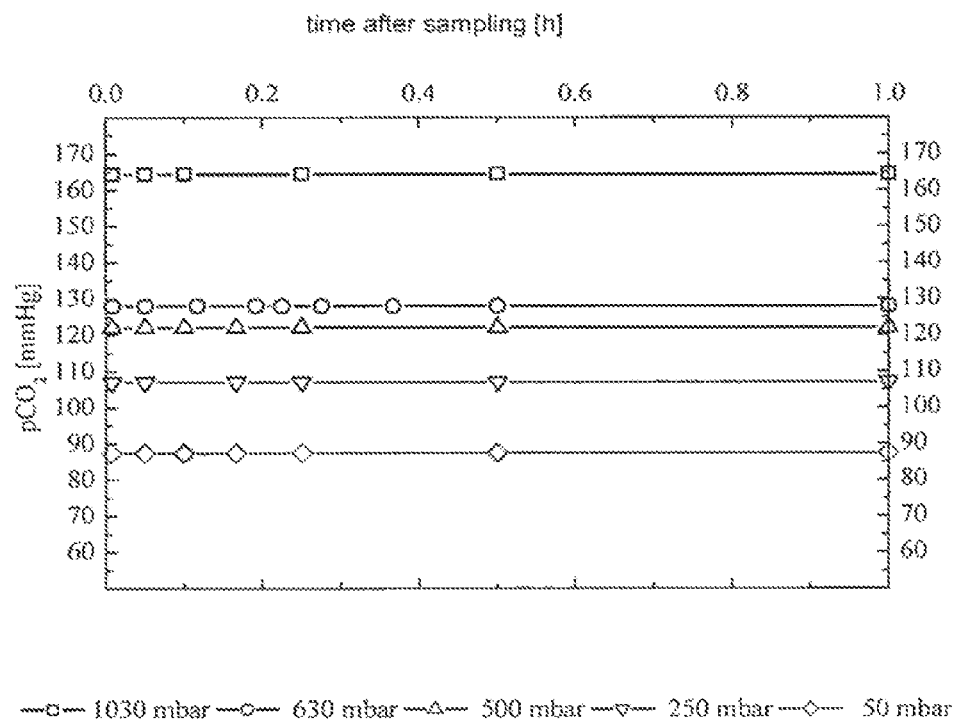
Figure 15:
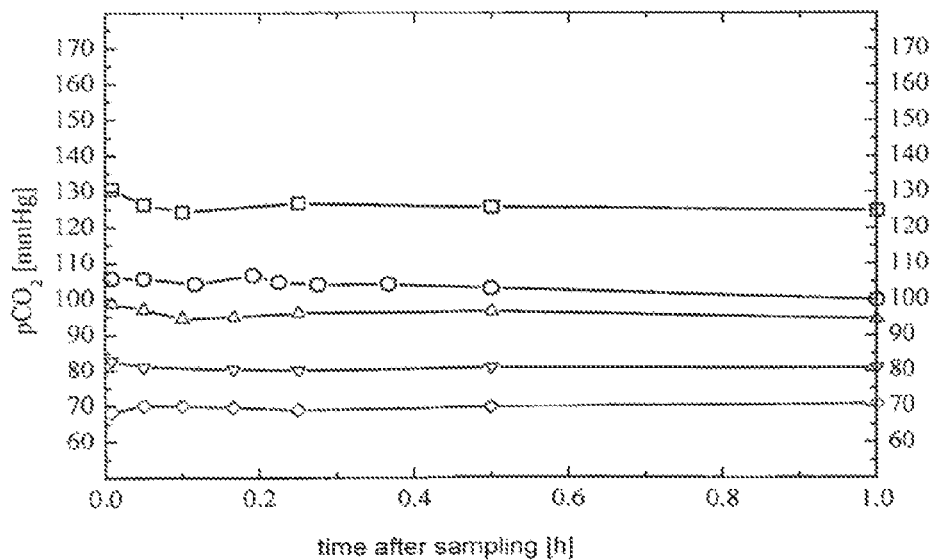

FIG. 15: In situ $CO_2$ equilibrium concentrations (Biostat ES) for different overpressures (A), time-dependent $CO_2$ concentrations in the sample subsequent to collection by means of gas-tight syringe and subsequent storage without overpressure (B)

0.15 M NaCl, 37° C., otherwise standard fermentation conditions in the stirring vessel.

Figure 16:
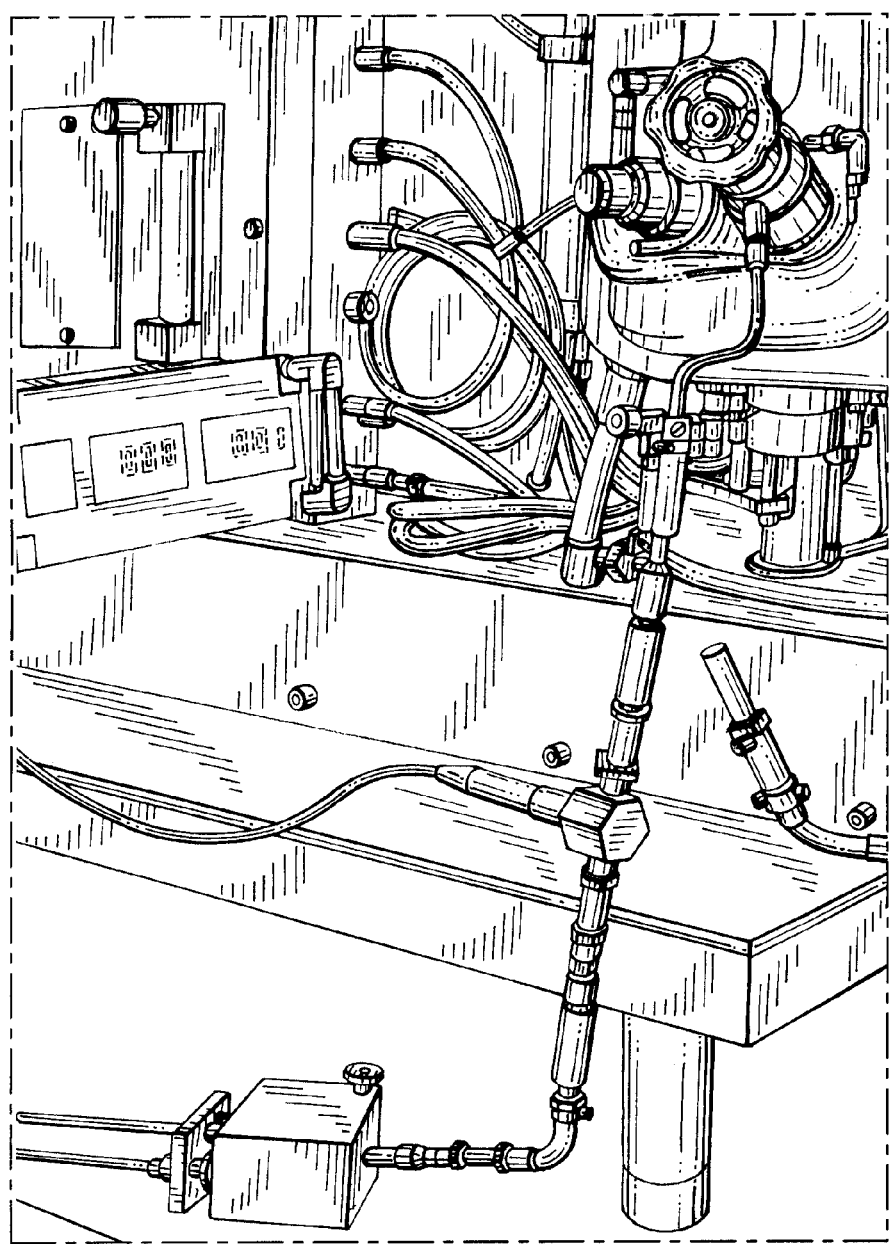

FIG. 16: Photo of the pressure-controlled sampling unit of Biostat ES with reference to the components described in the text FIG. 17: Transparent support unit (1) of the pressure-controlled sampling apparatus developed with three different syringes (2-4) for different sample volumes and adapter sleeve (5) for precise insertion of the syringes into the support Sample volumes can be pre-selected by locating the posterior stop plate (6) in position.

Figure 18:
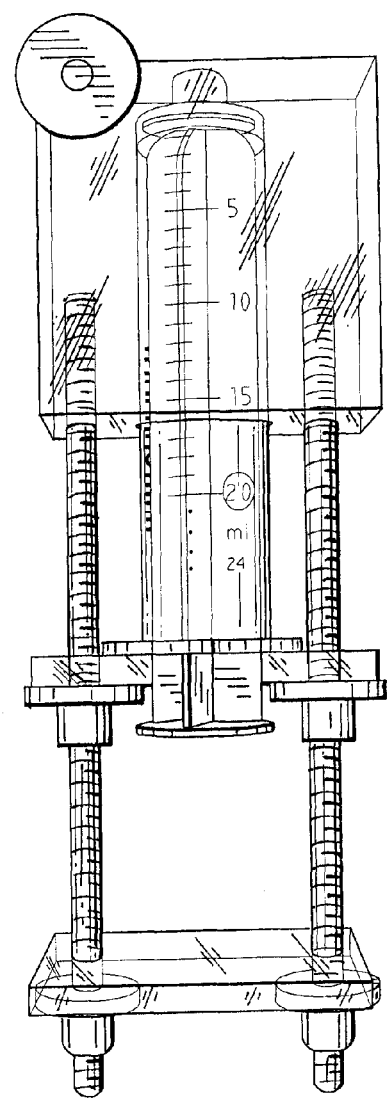

FIG. 18: Top view of the support unit of the developed pressure-maintaining sampling apparatus with installed syringe FIG. 19: Comparison of the in situ $CO_2$ concentrations (in situ YSI; off-line AVL Compact 3) in the cell-containing production medium at the end of a fermentation of the CHO-MUC1 cell line at 750 mbar overpressure Storage of the samples at 37° C. and without agitating during the measurement period; reaction tubes (50 mL, Falcon) completely filled with medium.

Figure 20:
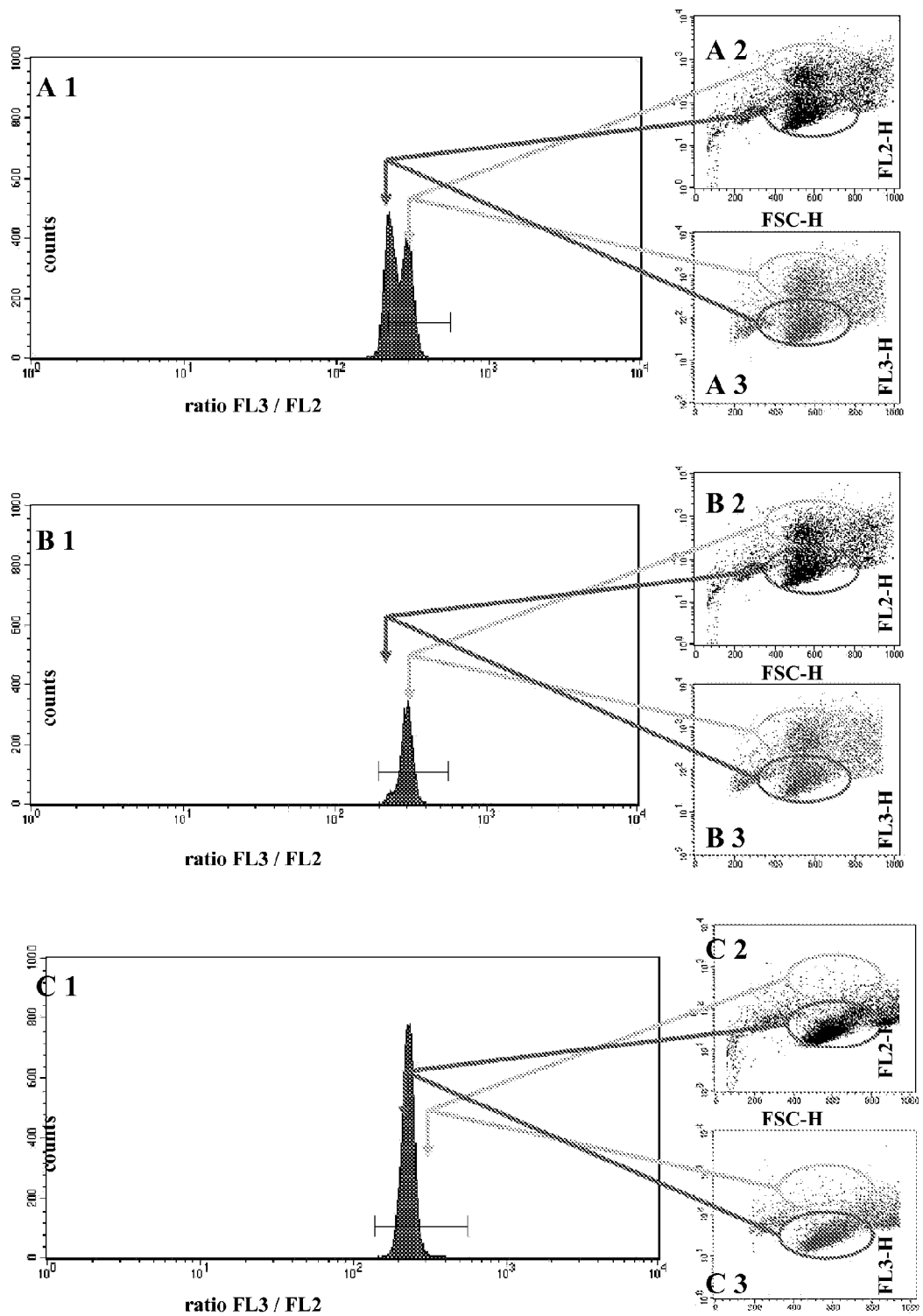

FIG. 20: Flow cytometric $pH_i$ measurements after 25 min (A,B) and 50 min (C), respectively, of pressureless incubation with the fluorescence dye SNARF-1; fluorescences (FL2, FL3) and their intensity ratio (ratio), respectively Explanations: see text.

Figure 21:
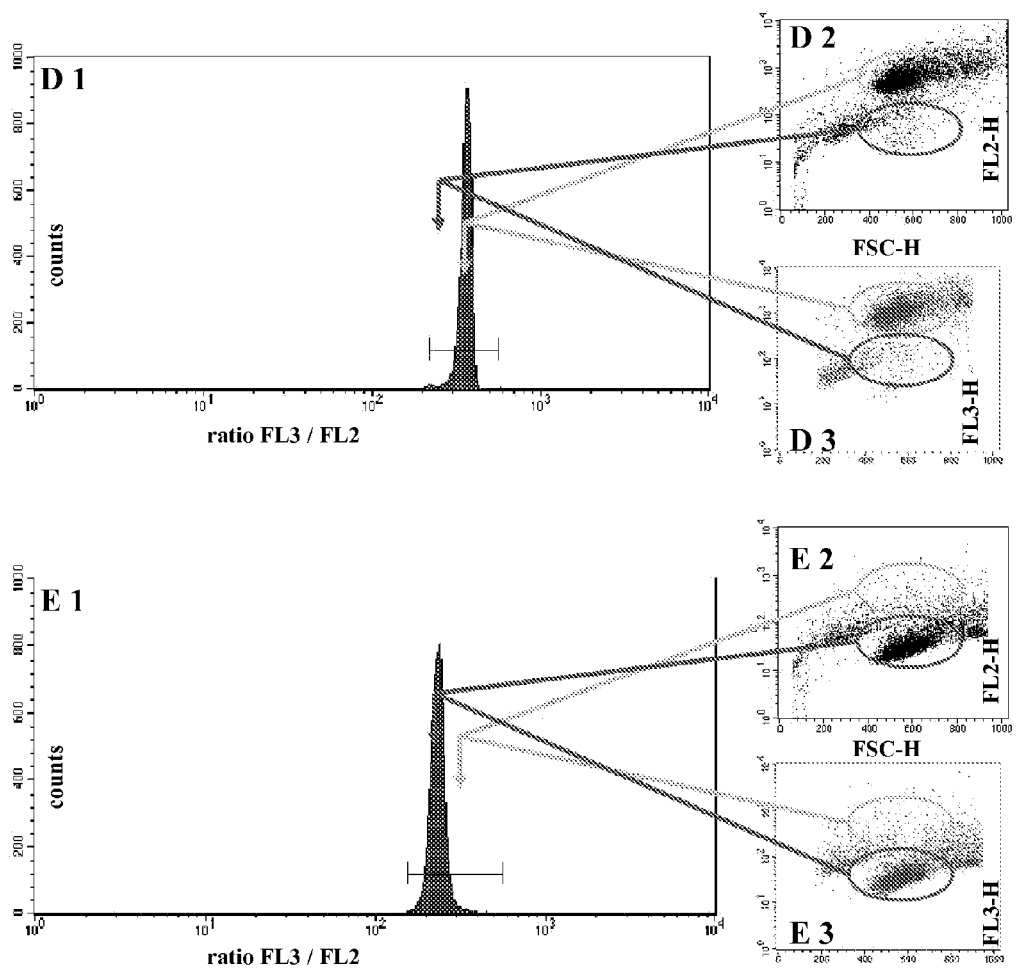

FIG. 21: Flow cytometric $pH_i$ measurements after 25 min isobaric incubation in the developed pressure-controlled sampling apparatus with the fluorescence dye SNARF-1 (D) and after isobaric storage (25 min) and subsequent pressureless incubation (25 min) with the fluorescence dye SNARF-1 (E); fluorescences (FL2, FL3) and their intensity ratio (ratio), respectively Explanations: see text.

Figure 22:
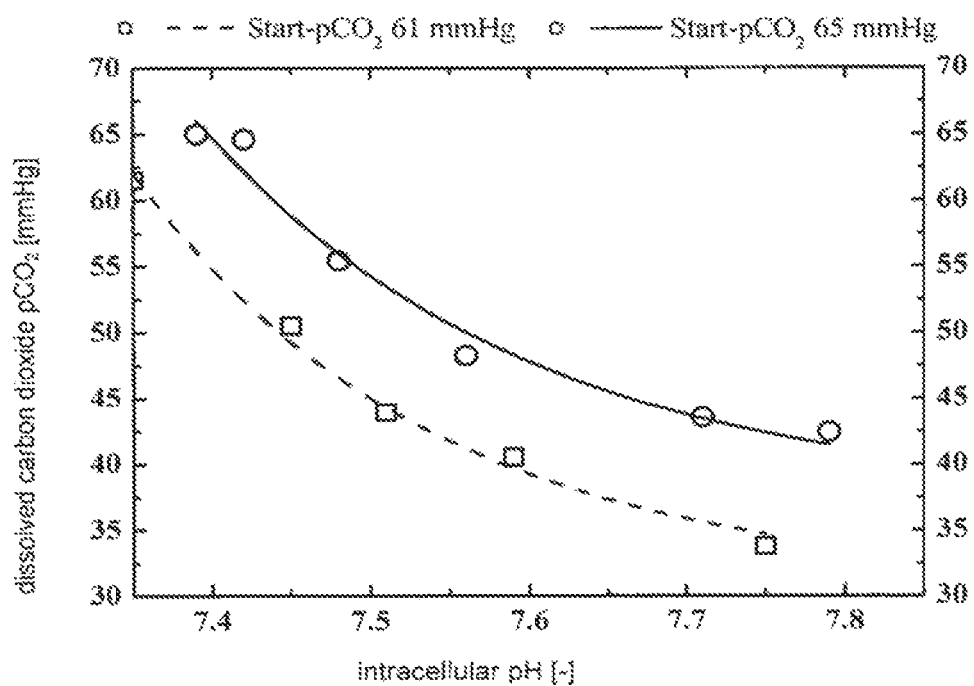

FIG. 22: Temporary intracellular alkalizing effect of different $pCO_2$ depletions in the medium on the CHO-MUC1 cell line cultured in the medium $pCO_2$ depletion by gassing the SNARF-1-dyed cell suspension in vitro with air at different incubation time. For all samples, the total duration of incubation prior to flow cytometric evaluation of intracellular pH is identical with the duration of neutralization by gassing with air.

Figure 23:
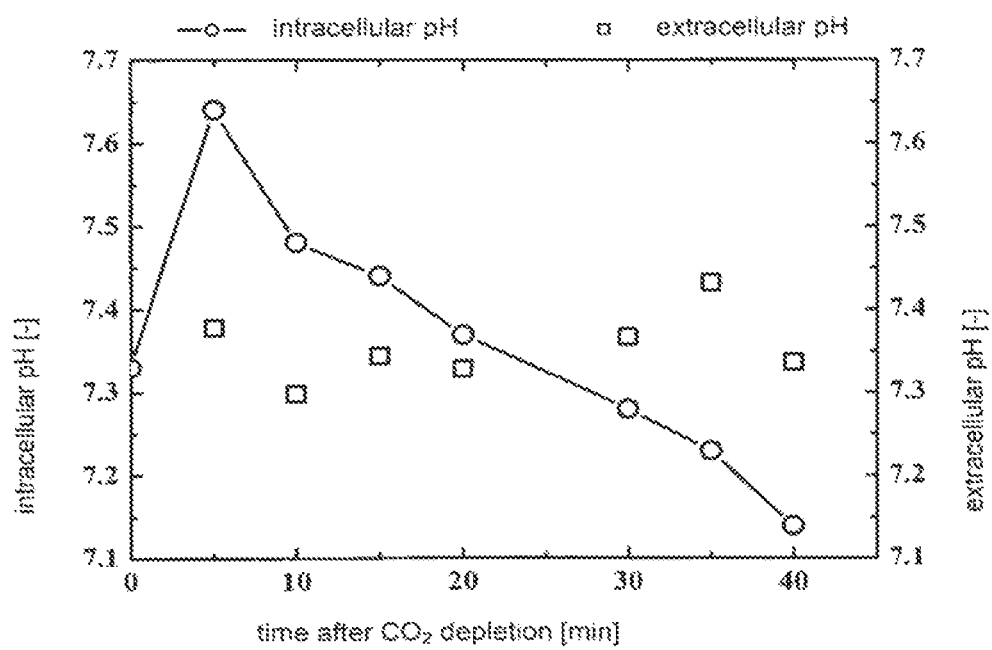

FIG. 23: Initial intracellular alkalizing effect (<5 min) upon depletion of dissolved $CO_2$ from the culture medium on the CHO-MUC1 cell line cultured therein and subsequent acidification of cytosol due to physiological effect (<40 min)

$CO_2$ depletion by gassing the SNARF-1-dyed cell suspension in vitro with air at different incubation stages. For all samples, the total duration of incubation prior to flow cytometric evaluation of intracellular pH is identical with the duration of neutralization by gassing with air.

Figure 24:
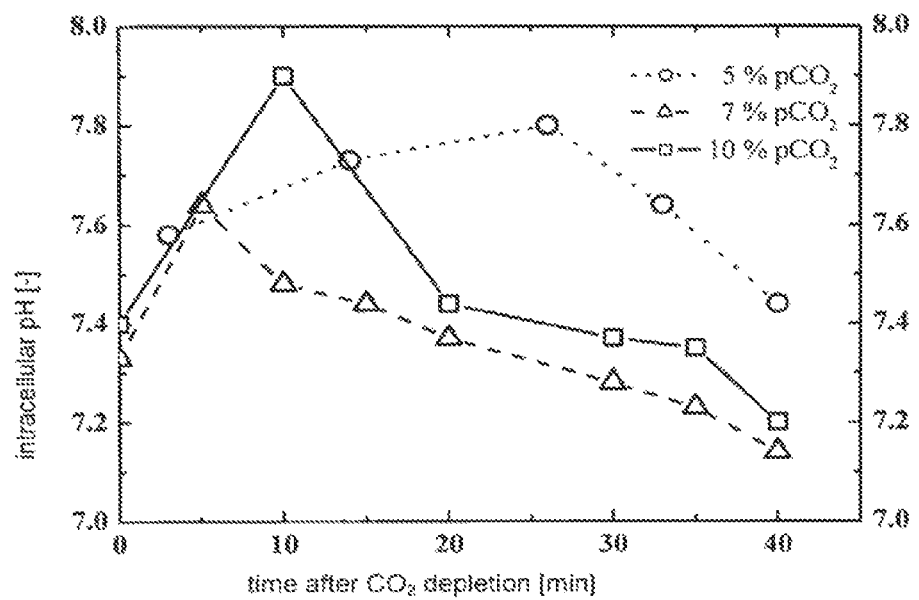

FIG. 24: Biphasic $pH_i$ curves at different start $pCO_2$ concentrations of 5%, 7% and 10%. Initial intracellular alkalizing effect upon depletion of dissolved $CO_2$ from the culture medium on the CHO-MUC1 cell line (chemical effect) and subsequent supercompensation of the alkalization due to the physiological effect below initial $pH_i$ $CO_2$ depletion by gassing the SNARF-1-dyed cell suspension in vitro with air at different incubation time. For all samples, the total duration of incubation prior to flow cytometric evaluation of intracellular pH is identical with the duration of neutralization by gassing with air.

Figure 25:
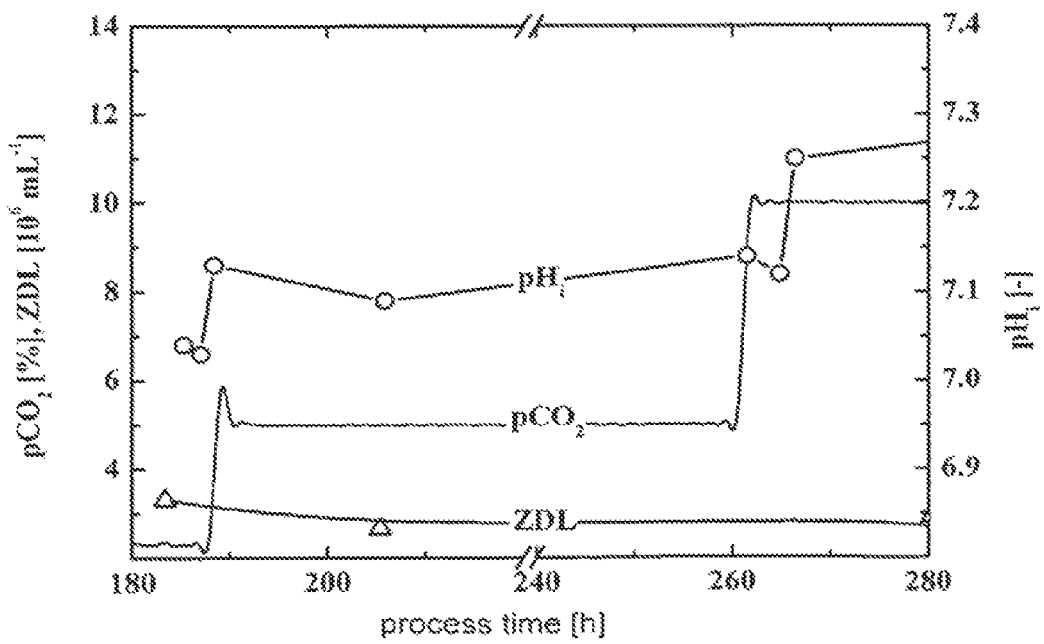

FIG. 25: Continuous $pCO_2$-controlled process (1.0 L, D=0.8 d$^{-1}$, pH 7.0, adjustment agent $Na_2CO_3$ surges of 2.5% to 5.0% and from 5.0% to 10%, respectively FIG. 26: Viable cell numbers ZDL and viabilities VIA at 5%, 15%, 25% and 5-15% $pCO_2$, respectively CHO-MUC1, 10 L fed batch, 750 mbar overpressure, standard fermentation conditions.

Figure 27:
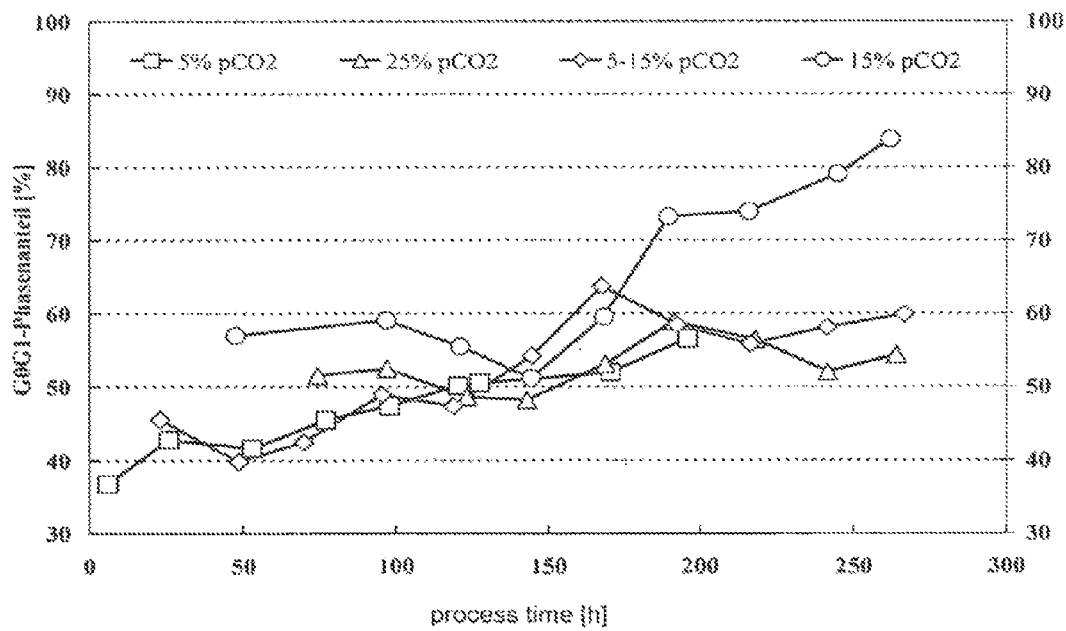

FIG. 27: G0G1 phase fraction of the cell cycle distributions in processes with different $pCO_2$ set value controls CHO-MUC1, 10 L fed batch, 750 mbar overpressure, standard fermentation conditions.

Figure 28:
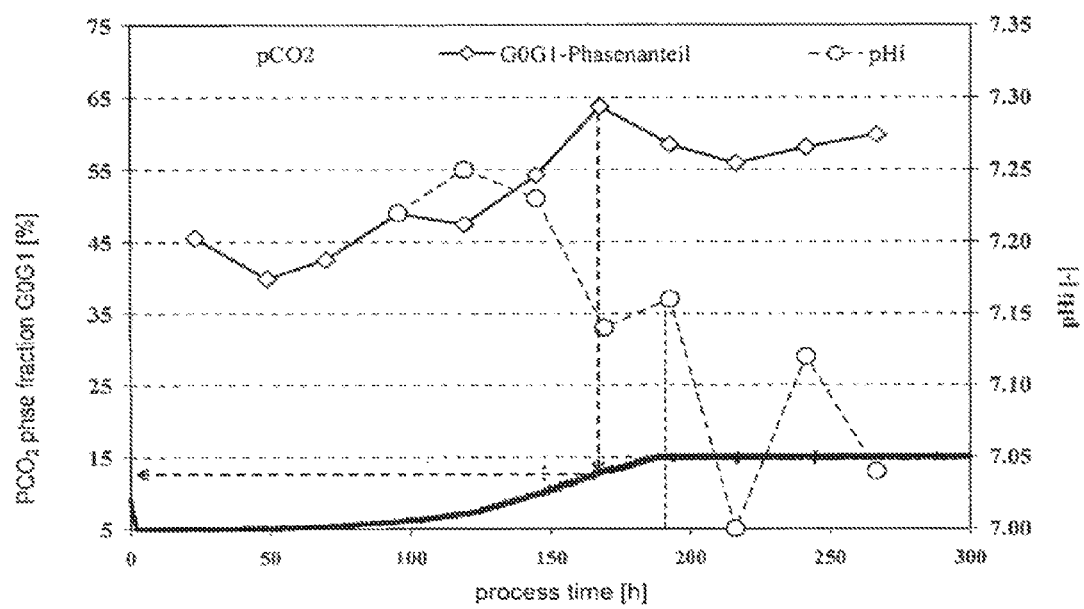

FIG. 28: Turning point in the cell cycle phase fraction G0G1, corresponding $pCO_2$ value and intracellular $pH_i$-value in the industrial $pCO_2$ profile 5-15%, CHO-MUC1, 10 L fed batch, 750 mbar overpressure, standard fermentation conditions.

Figure 29:
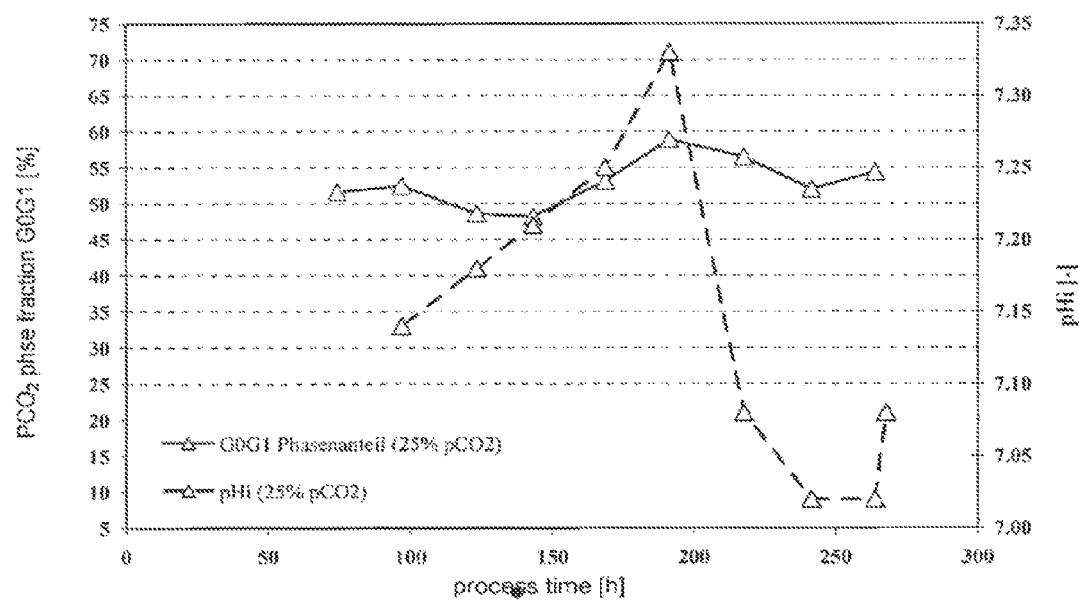

FIG. 29: G0G1 phase fraction and intracellular pH-value $pH_i$ at 25% $pCO_2$ CHO-MUC1, 10 L fed batch, 750 mbar overpressure, standard fermentation conditions.

Figure 30:
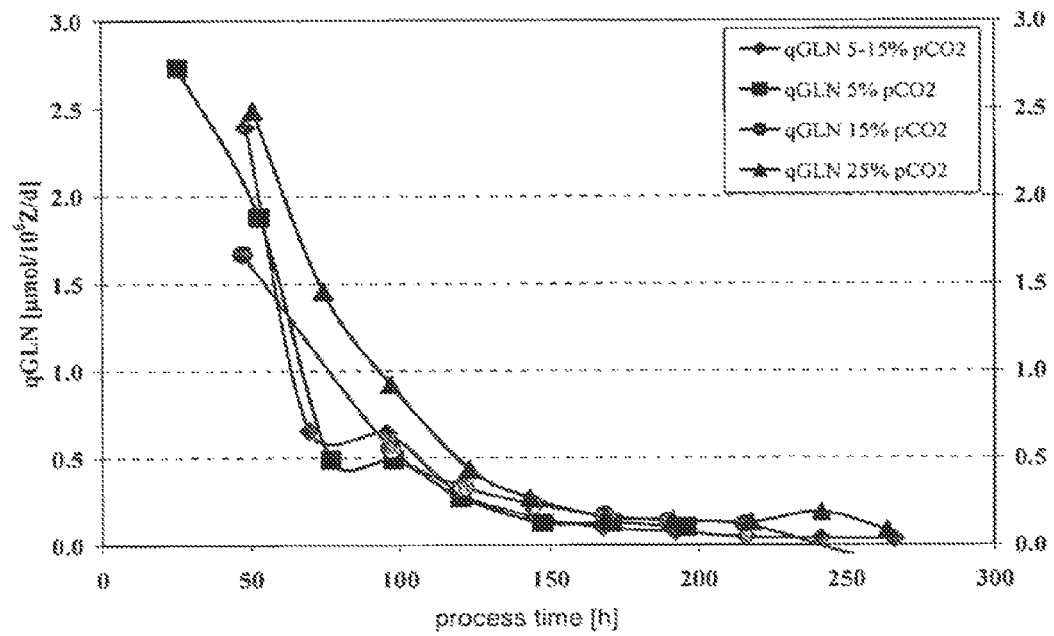

FIG. 30: Specific rates of glutamine consumption qGLN for different $pCO_2$ set value profiles CHO-MUC1, 10 L fed batch, 750 mbar overpressure, standard fermentation conditions.

Figure 31:
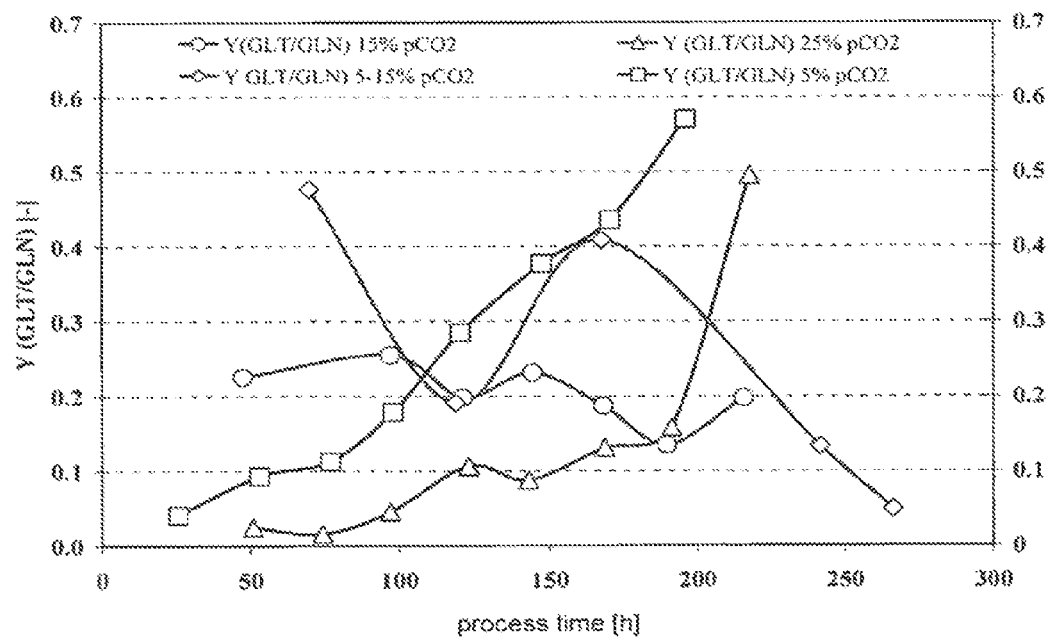

FIG. 31: Specific yield coefficients Y related to glutamate GLT per glutamine GLN CHO-MUC1, 10 L fed batch, 750 mbar overpressure, standard fermentation conditions.

Figure 32:
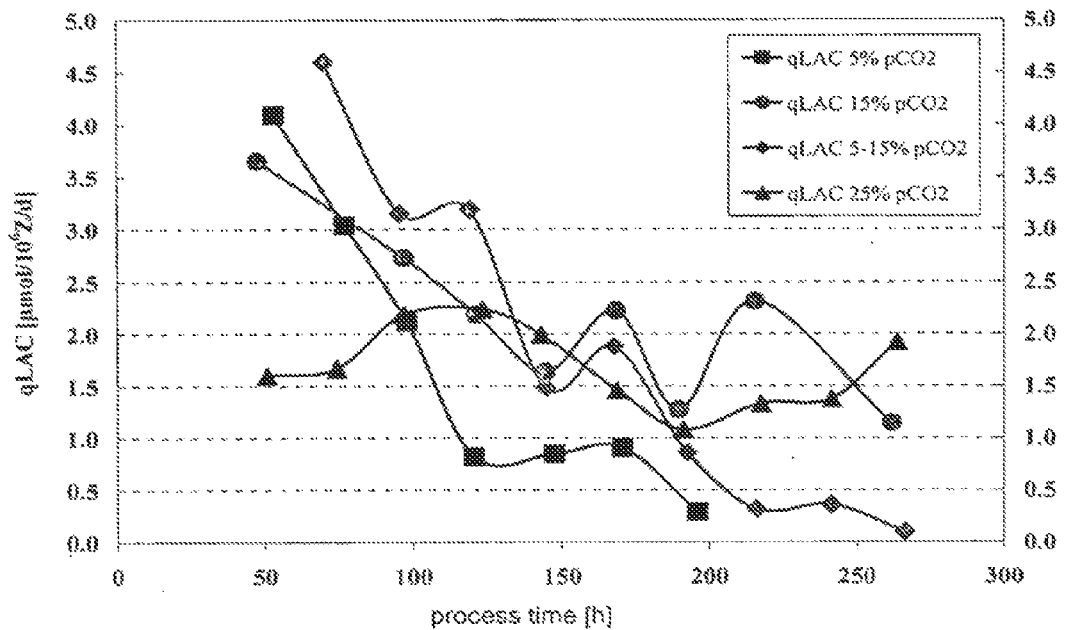

FIG. 32: Cell-specific lactate formation rates qLAC for different $pCO_2$ set value profiles CHO-MUC1, 10 L fed batch, 750 mbar overpressure, standard fermentation conditions.

Figure 33:
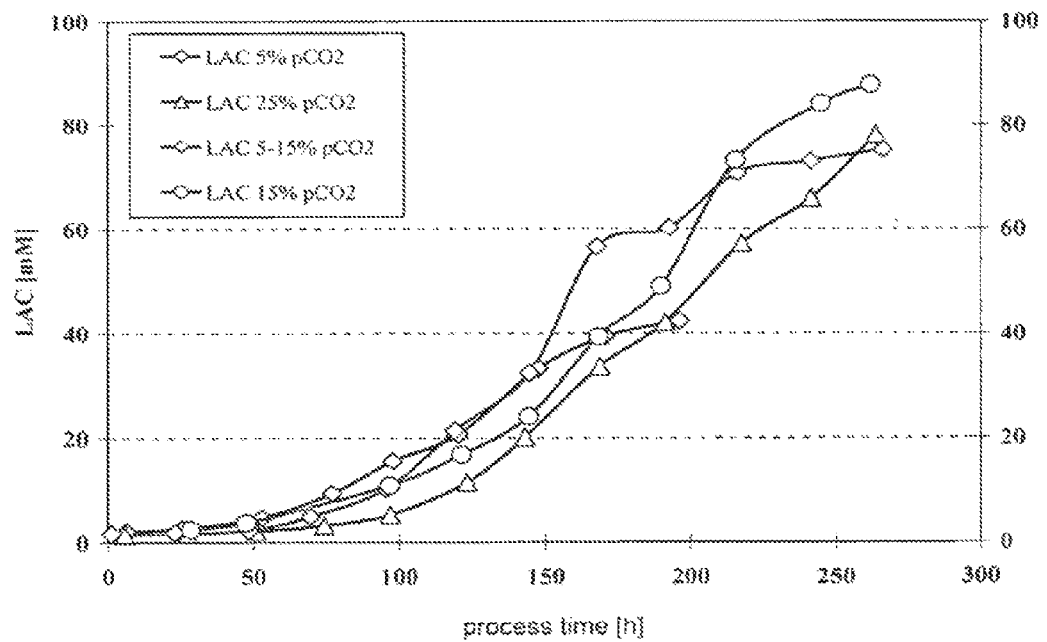

FIG. 33: Lactate formation LAC for different $pCO_2$ set value profiles

CHO-MUC1, 10 L fed batch, 750 mbar overpressure, standard fermentation conditions.

Figure 34:
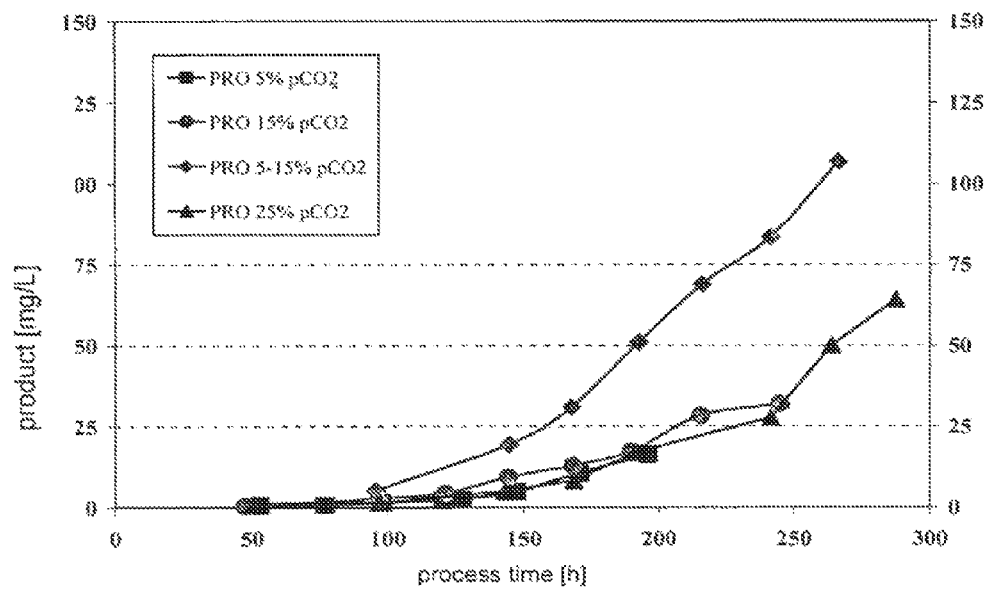

FIG. 34: Product titre PRO MUC1-IqG

10 L fed batch, 750 mbar overpressure, standard fermentation conditions.

Figure 35:
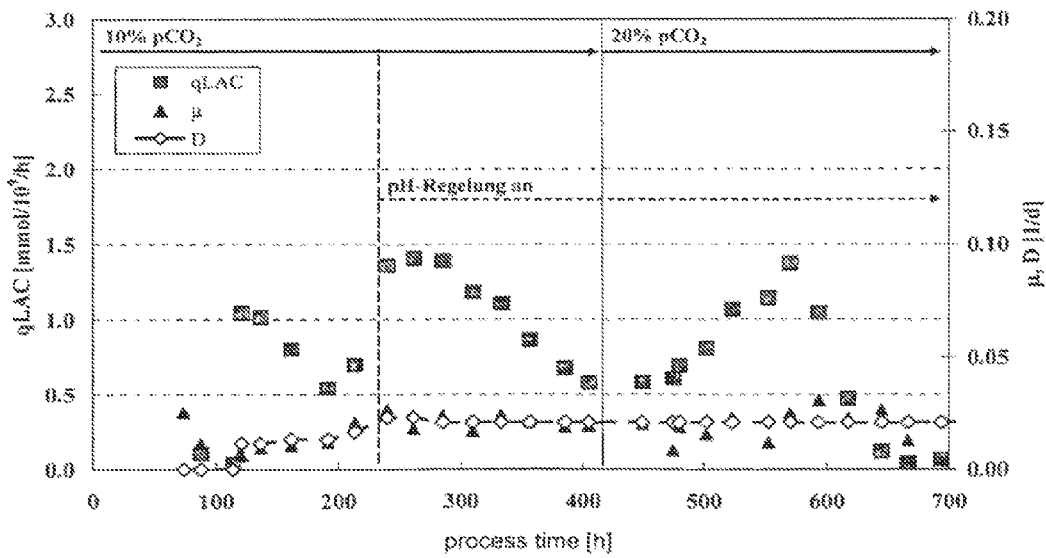

FIG. 35: Glucose-limited chemostat process (1 L) of cell line CHO-MUC1

Cell-specific lactate formation qLAC increased by pH control and increase in $pCO_2$ set value, respectively; specific growth rate μ, flow rate D.

Figure 36:
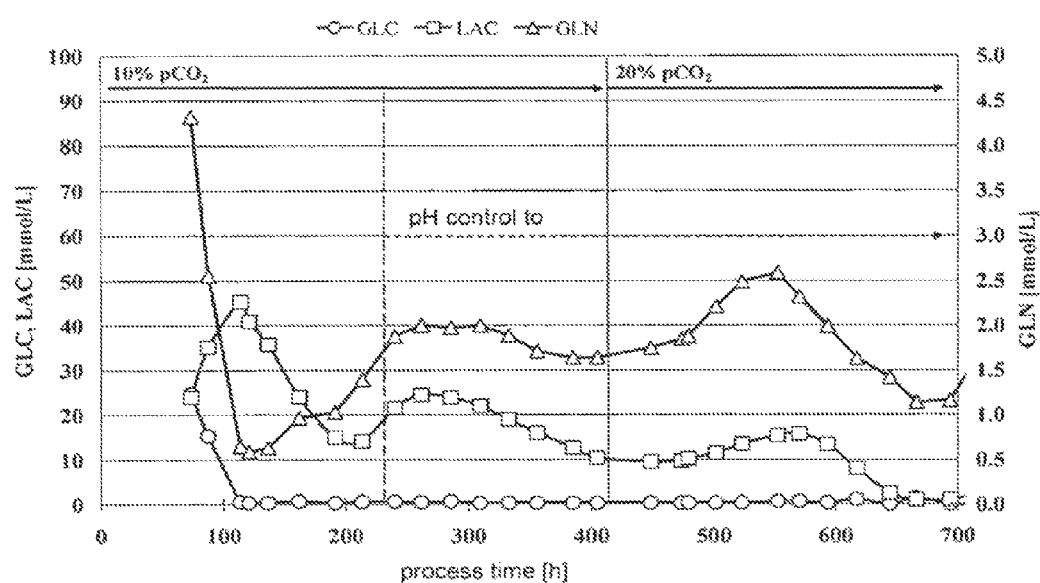

FIG. 36: Glucose-limited chemostat process (1 L) of cell line CHO-MUC1

Curves of glucose, lactate and glutamine concentration, respectively (GLC, LAC and GLN).

Figure 37:
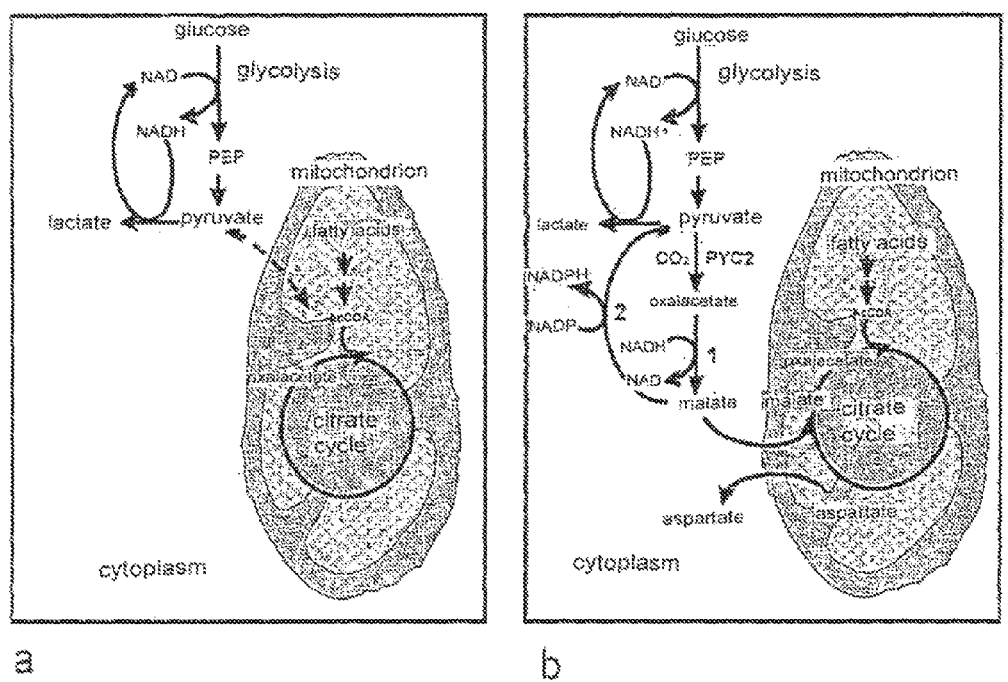

FIG. 37: (a) conventional metabolic pathway of the substrate glucose via pyruvate to lactate; (b) enabling the transformation of pyruvate and hydrogen carbonate into oxaloacetate and transfer of subsequent malate into the tricarbonic acid cycle (TCA) by cytosolic pyruvate carboxylase PYC2; modified according to Irani (1999)

Figure 38:
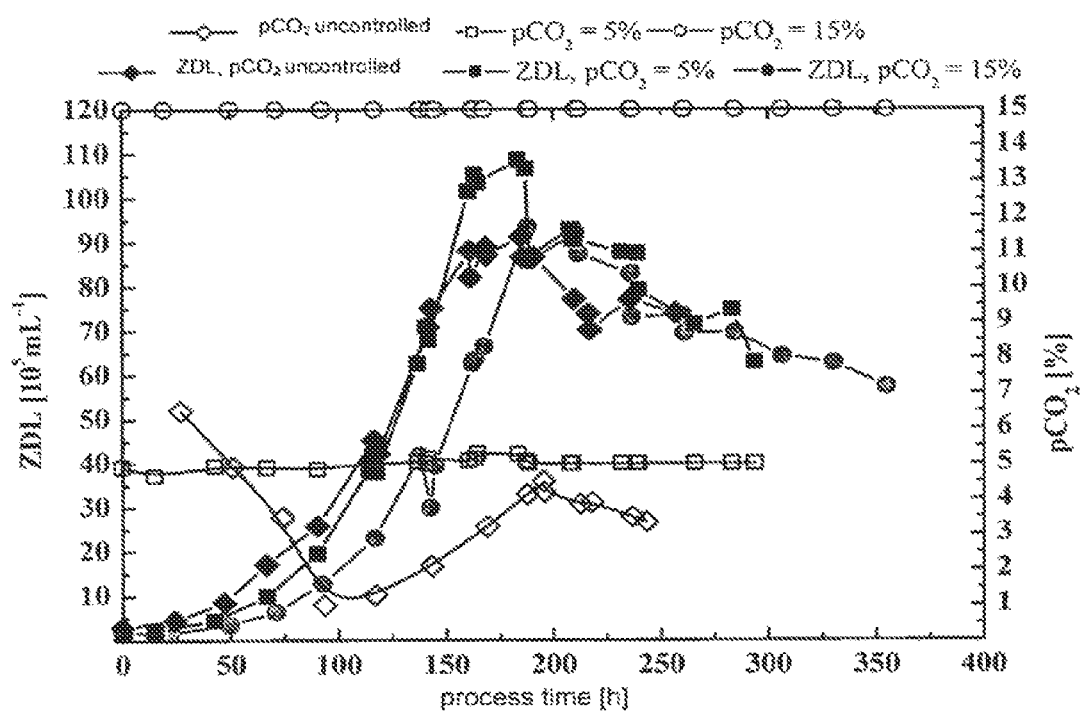

FIG. 38: Fed-batch cultivation of cell line CHO-hGM-CSF-PYC2: curve of viable cell densities (filled symbol) and $pCO_2$ concentrations (open symbol), adjustment of $pCO_2$ to 5% and 15% and/or no adjustment of $pCO_2$, respectively FIG. 39: Viable cell densities ZDL and viabilities VIA at uncontrolled and controlled pCO2 concentrations of 5% and 15%, respectively, in 1 L fed-batch of cell line CHO-hGM-CSF-PYC2: $pCO_2$ control allows prolonged production period with highly viable cells FIG. 40: Osmolality OSM and cumulative lye inlet (1 M $Na_2CO_3$) with uncontrolled $pCO_2$, controlled $pCO_2$ at 5% and 15%, respectively Enhanced lye inlet during the exponential growth phase with uncontrolled $pCO_2$ in comparison to $pCO_2$-controlled processes; the osmolality curve is similar in all processes.

Figure 41:
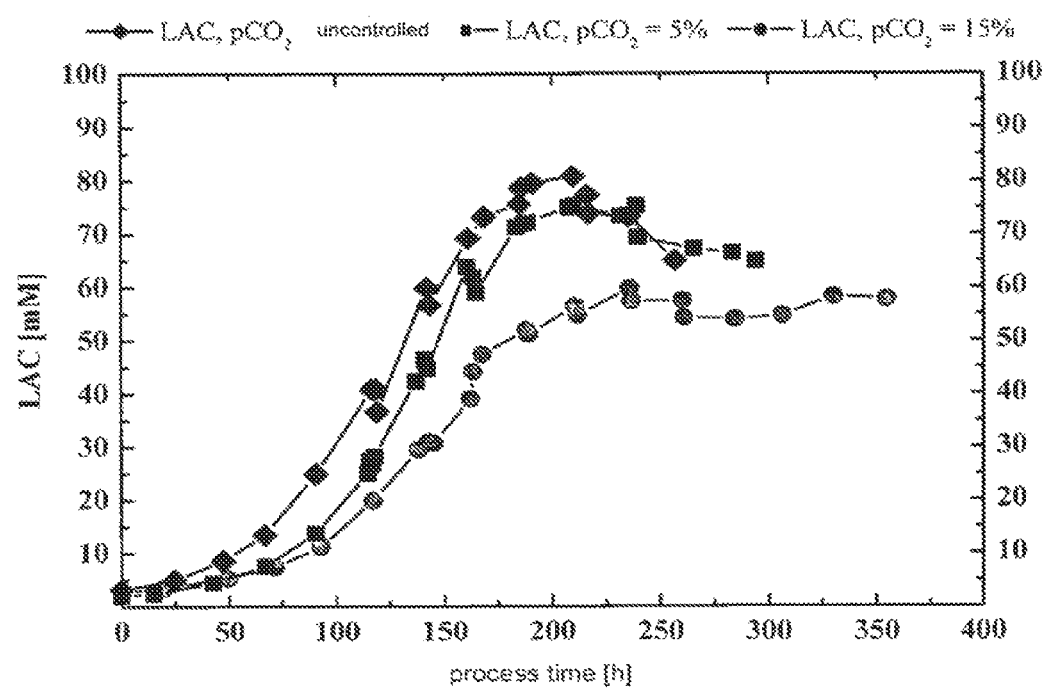

FIG. 41: Lactate concentrations LAC in the individual bioprocesses $pCO_2$ control prevents rapid and high lactate formation.

Figure 42:
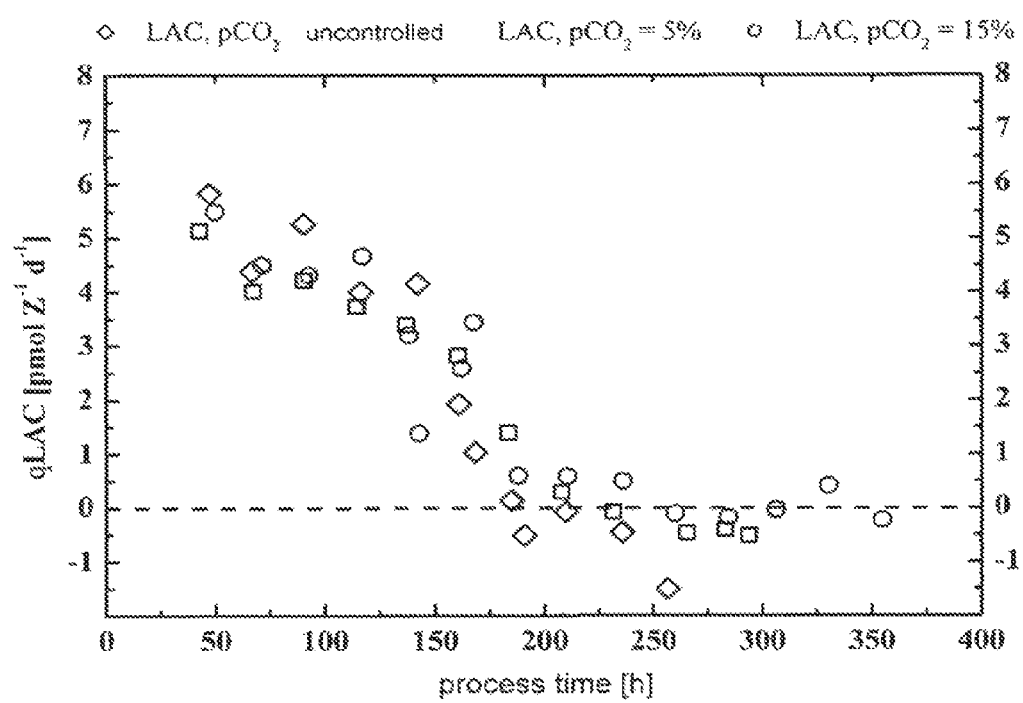

FIG. 42: Cell-specific lactate formation rates qLAC

Lactate metabolism with uncontrolled $pCO_2$ ($\geq$180 h) and controlled $pCO_2$ of 5% ($\geq$220 h) can be observed; no metabolism of lactate with controlled $pCO_2$ of 15%.

Figure 43:
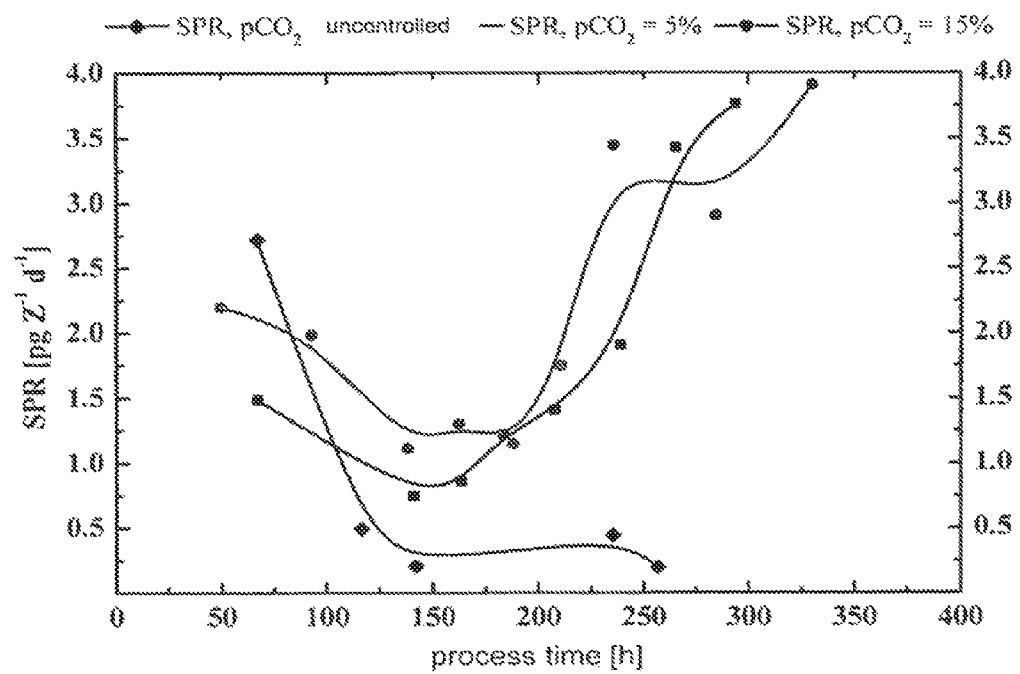

FIG. 43: Cell-specific product formation rates SPR of the recombinant growth factor hGM-CSF with different $pCO_2$ process conditions Inverse activity in $pCO_2$-uncontrolled process in comparison to $pCO_2$-controlled processes: decrease of SPR upon entry into stationary growth phase without $pCO_2$ control; in contrast, high increase in SPR with controlled $pCO_2$ of 5% and 15%, respectively.

Figure 44:
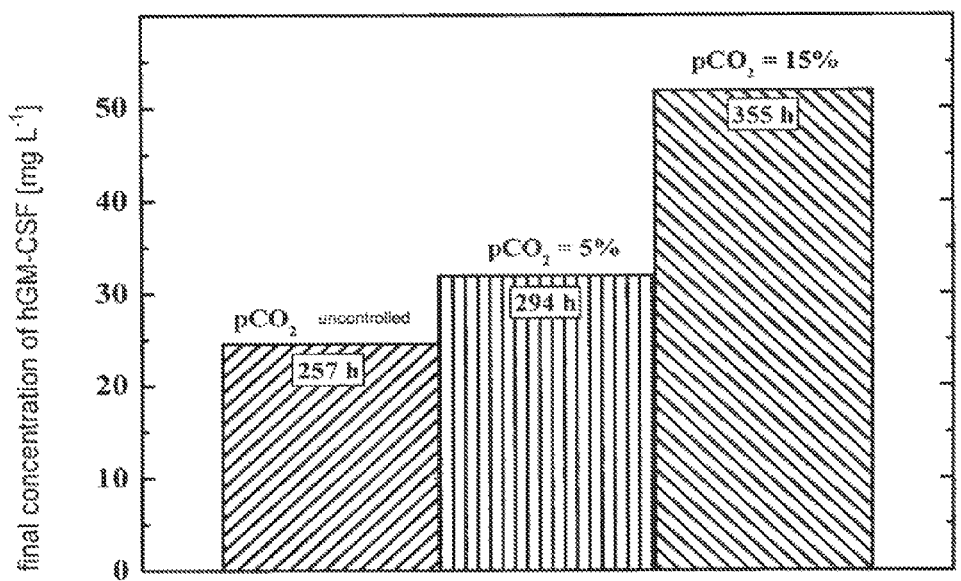

FIG. 44: Absolute final concentration of growth factor hGM-CSF produced at the end of fermentation (80% viability of the culture) for the relevant $pCO_2$ profile FIG. 45: Cell cycle distribution ratio S/(G0G1), cell-specific product formation rate SPR and intracellular pH value $pH_i$ in the course of a $pCO_2$-uncontrolled-uncontrolled fed-batch culture of cell line CHO-hGM-CSF-PYC2

Decrease of $pH_i$ of about 0.3 subsequent to the beginning of feed, increase in $pH_i$ at entry into the growth phase.

Figure 46:
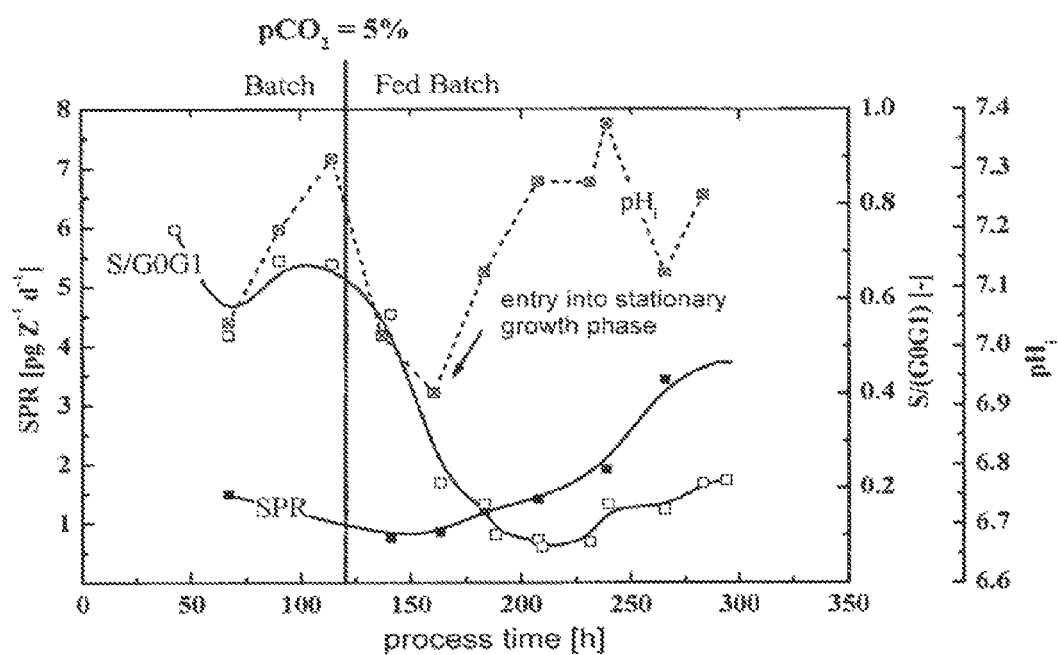

FIG. 46: Cell cycle distribution ratio S/(G0G1), cell-specific product formation rate SPR and intracellular pH value $pH_i$ in the course of a fed-batch culture of cell line CH-hGM-CSF-PYC2 $CO_2$-controlled to 5%

Decrease of $pH_i$ of about 0.4 subsequent to the beginning of feed, increase in $pH_i$ at entry into the stationary growth phase.

Figure 47:
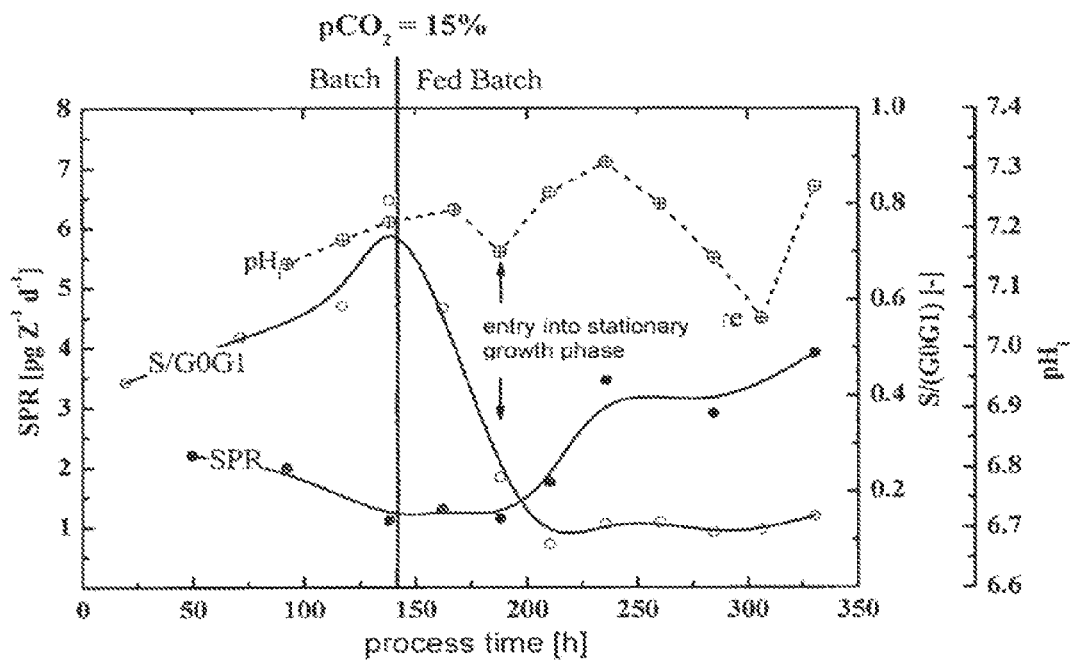

FIG. 47: Cell cycle distribution ratio S/(G0G1), cell-specific product formation rate SPR and intracellular pH value $pH_i$ in the course of a fed-batch culture of cell line CH-hGM-CSF-PYC2 $pCO_2$-controlled to 15%

No decrease of $pH_i$ subsequent to the beginning of feed, initially minor reduction of the $pH_i$ increase at entry into the stationary growth phase, subsequently increase with the SPR.

Figure 48:
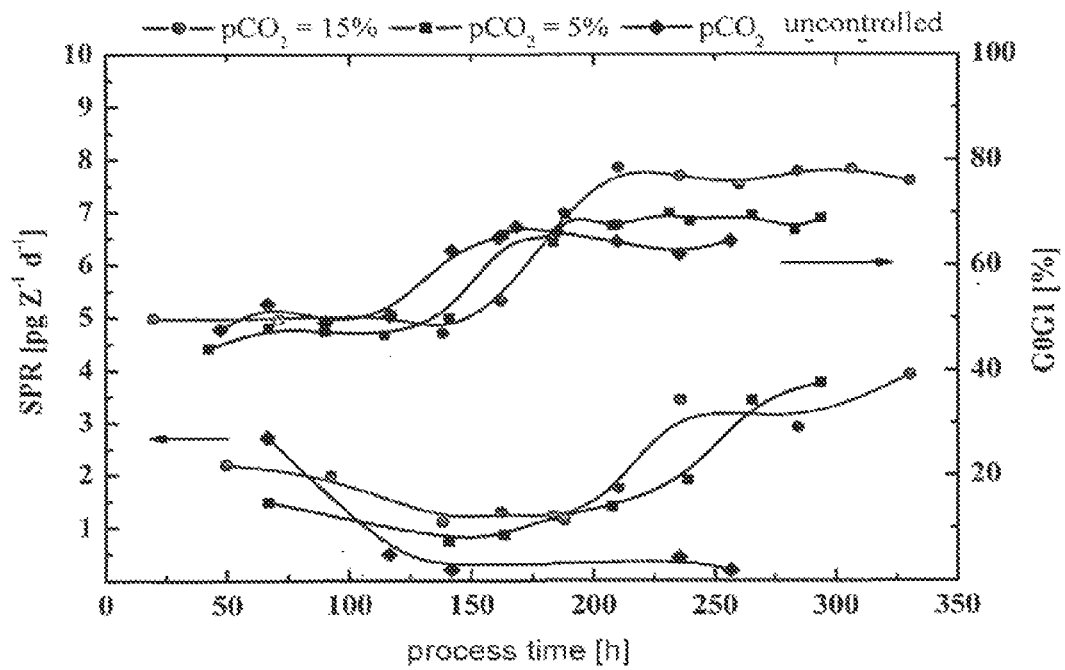

FIG. 48: Cell-specific productivities and cell cycle phase fractions G0G1 of the fed-batch processes with uncontrolled and/or up to 5% and 15% $pCO_2$ controlled $pCO_2$ 1 L scale, cell line CHO-hGM-CSF-PYC2, standard fermentation conditions.

Figure 49:
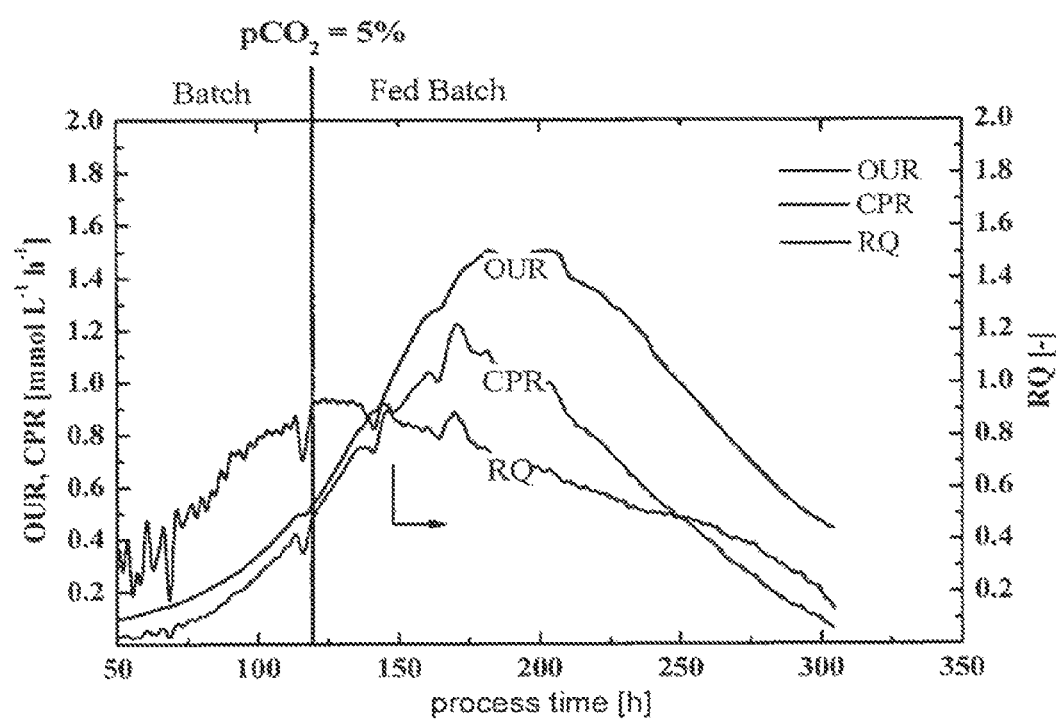

FIG. 49: OUR, CPR and RQ of the fed-batch process with controlled $pCO_2$ of 5%

CHO-hGM-CSF-PYC2, 1 L fed batch, standard fermentation conditions.

Figure 50:
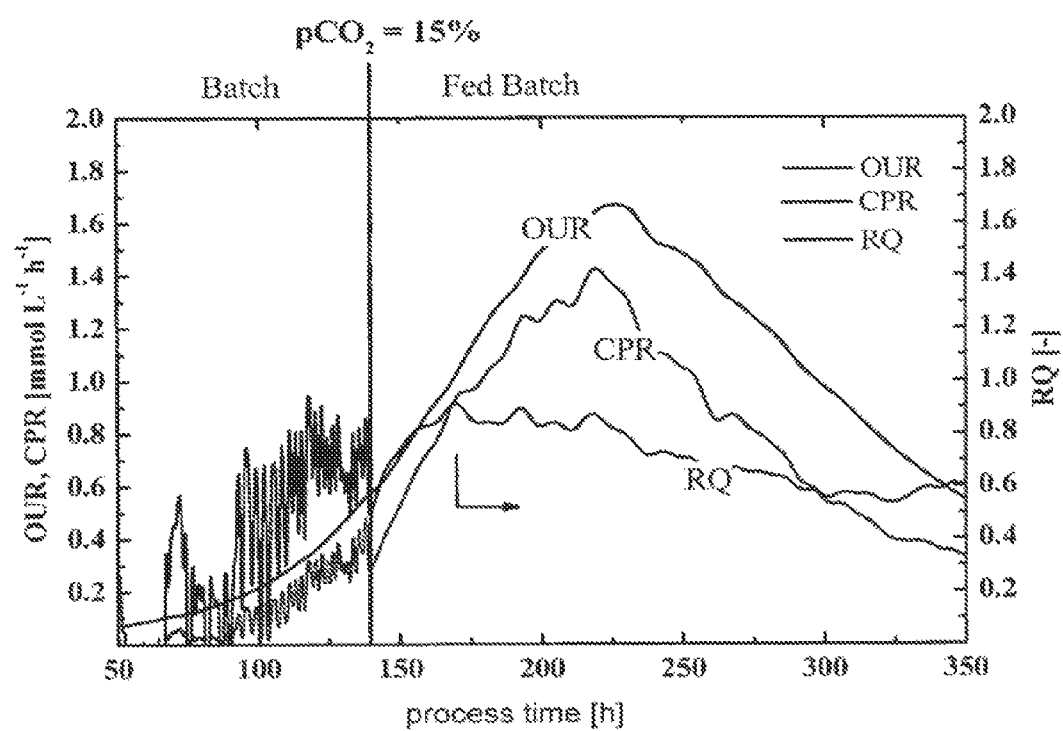

FIG. 50: OUR, CPR and RQ of the fed-batch process with controlled $pCO_2$ of 15%

CHO-hGM-CSF-PYC2, 1 L fed batch, standard fermentation conditions.

FIG. 51 shows the removal of flanking yeast-specific sequences from the 5'- and 3'-regions of the PYC2 gene.

DETAILED DESCRIPTION OF THE INVENTION

Thus, the present invention relates to a method for the recombinant production of a polypeptide in a eukaryotic host cell modified in the citrate cycle, wherein the method comprises the following steps:

(a) cultivating the eukaryotic host cell in a suitable medium under conditions which allow the expression of the polypeptide, wherein the content of dissolved $CO_2$ ($pCO_2$) in the medium is maintained at a constant value in the range of 10% to 20%; and (b) recovering the polypeptide from the cell or from the medium.

Due to the method of the present invention, a very high product concentration is achieved, resulting in a reduction of recovery costs. Thus, the increase in the product titre allows the production of a desired amount of products in a small culture volume, which results in lower investment costs.

The person skilled in the art is familiar with genes the products of which are involved in the citrate cycle and, thus, he is able to produce eukaryotic host cells which are modified in the citrate cycle and which are suitable for the method of the present invention (cf., e.g., Irani et al., (1999), Chen et al., (2001); Paredes et al., (1999), Bell et al., (1995)). In addition, the person skilled in the art can use host cells exhibiting modifications as the above which are already obtainable from sources accessible to the public. Furthermore, the person skilled in the art is also familiar with suitable culture conditions and media for the cultivation of such cells as well as with conditions under which the gene expressing the desired recombinant protein is expressed to a high degree. In order to achieve a constant content of dissolved $CO_2$ in the medium, the person skilled in the art can preferably make use of the control units which are described in the following Examples.

The term "constant value" or "stable value" as used herein refers to the fact that the content of dissolved $CO_2$ does not deviate more than 20% from the desired or programmed set value, i.e., for example, it is in the range of 8-12% for a set value of 10%.

The method of the present invention can be carried out using different eukaryotic production cell lines. The modification in the citrate cycle, preferably a genetic modification, can be effected, for example, by insertion of additional genes of the same organism or of another organism into the DNA or by a vector or by enhancing or attenuating the activity or expression of a gene by introducing a more effective promoter, e.g. from CMV, or by corresponding mutations in the coding region of the gene which lead to the substitution, deletion or addition of one or more amino acid residues.

In a preferred embodiment of the method of the present invention, the host cell is an animal cell, preferably a mammalian cell or insect cell. Such cells, in particular cells for the efficient production of recombinant polypeptides are known to the person skilled in the art. The following cell lines can be indicated by way of example: mammalian cells such as CHO cell lines, e.g. CHO-K1, BHK, such as BHK-21, hybridoma, NS/0, other myeloma cells and insect cells or other higher cells. The use of cells which do not produce in a growth-dependent manner is particularly preferred.

In a further embodiment of the method of the present invention, the host cell is a host cell that is modified in the citrate cycle. The different metabolic pathways of the citrate cycle have been known for a long time, as have the genes involved and their control. Thus, the person skilled in the art is able to carry out the desired modification(s) according to standard methods. A particularly preferred host cell modified in the citrate cycle is a cell expressing cytosolic pyruvate carboxylase, preferably a cytosolic pyruvate carboxylase from Saccharomyces cerevisiae (PYC2, isoenzyme 2). The gene coding this carboxylase and suitable expression vectors for the transformation of eukaryotic cells are described, amongst others, in U.S. Pat. No. 6,706,524 and Stucka et al. (1991); see also Wagner (1998); Irani (1999); Bollati Fogolin (2003); WO 00/46378.

The cell line CHO-hGM-CSF-PYC2, which contains the plasmid pCMVSHE-PYC2, the production of which plasmid is also described in U.S. Pat. No. 6,706,524 in detail, is particularly preferred for the method of the present invention.

The method of the present invention allows to obtain high yields of polypeptides, such as glycoproteins, fusion proteins, antibodies and their fragments, interferons, cytokins, preferably hGM-CSF, growth factors, e.g. erythropoietin (EPO), hormones etc. in a recombinant manner.

An essential feature of the method of the present invention is the fact that the content of dissolved $CO_2$ is maintained constant using suitable measures as described in the following Examples. The person skilled in the art can—dependent on the cell line used—determine the particularly suitable content of $CO_2$ within the range of 10% to 20% by means of standard assays. The content of dissolved $CO_2$ ($pCO_2$), which is to be maintained constant, is preferably in the range of 10% to 20%, more preferably in the range of 11% to 19%, more preferably in the range of 12% to 18%, more preferably in the range of 12.5% to 17.5%, more preferably in the range of 13% to 17%, more preferably in the range of 14% to 16%.

The method of the present invention can be carried out using known methodologies, e.g. batch, fed-batch, chemostatic process or perfusion culture, with the fed-batch process being preferred. All established types of culture vessels, such as stirring vessels, can be used for these processes. Preferably, the culture system should allow for high cell densities.

In principle, any medium suitable for the cultivation of eukaryotic cells can be used as culture medium. For the cultivation of mammalian cells, it is possible to use media which are based on the known formulations, such as IMDM, DMEM or Ham's F12, and which possibly have been optimized for the method of the present invention so that there is no limitation with respect to specific individual components. This can be achieved, for example, by a higher concentration of individual components. In principle, it is also possible to dose single nutrients separately from the medium if necessary.

The pH range is preferably between 6.7-7.7, particularly preferred between 7-7.3. However, other pH ranges are also conceivable. The temperature range is preferably between 35° C.-38.5° C., particularly preferred at 37° C., e.g., for mammalian cells, such as CHO cells. However, other temperature ranges are also conceivable, such as e.g. <35° C. in the case of non-mammalian cells.

In order to maintain the content of dissolved $CO_2$ in the medium constant, it is preferably maintained constant by using a control system with a cascaded $pCO_2$ controller via mass flow controllers (MFC), for example, as described in the Examples below. An approach, wherein, via the MFC (a), the $CO_2$ ratio in the supply air is increased by an overcut of the set value of $pCO_2$ in the medium, (b) the $CO_2$ ratio in the supply air is decreased by an exceedance of the set value of $pCO_2$ in the medium, and (c) the cascaded controller opens an additional MFC for the delivery of $N_2$, preferably in combination with step (b), if the exceedance of the set value cannot be sufficiently compensated by a decrease of the $CO_2$ ratio in the supply air, is particularly preferred and advantageous.

Example 1

Material and Methods (A) Cell Lines

All cell lines used were adapted to culture in suspension in serum-free media.

(1) CHO-MUC1

The cell line CHO-MUC1 used in the present invention is based on a CHO-K1 cell line of ATCC (American Type Culture Collection, Rockville, USA) (CCL-61). It was transfected with the recombinant plasmid MUC1-IgG2a-pcDNA3 (Link et al., 2004) in confluent culture using electroporation. Apart from resistance against the antibiotic geneticin (G418), the construct, which is under constitutive control of the cytomegalovirus promoter (CMV), also mediates the expression of the MUC1-IgG2a fusion protein. The extracellular part of the human breast cancer-associated mucin glycoprotein MUC1 (C-terminal) is fused (N-terminally) to the Fc part of a murine immunoglobulin of subclass 2a (IgG2a) via an enterokinase cleavage site and, thus, it is secreted into the medium. Selection and subsequent subcloning resulted in clone CHO-MUC1-IgG2a-PH3931-16TR which was used in the present invention (Link, 2003). This cell line exhibits genicitin resistance up to a concentration of 400 µg mL$^{-1}$.

(2) CHO-hGM-CSF-PYC2

Clones of the recombinant CHO-hGM-CSF-PYC2 cell lines were provided by courtesy of M. Bollati Fogolin (GBF mbH, Braunschweig). They were generated by co-transfection of the recombinant cell line CHO-K1-hGM-CSF (Bollati Fogolin, 2001) with plasmids pCMVSHE-PYC2, which contains the gene coding cytosolic pyruvate carboxylase from yeast (Wagner, 1998; Irani, 1999) and pHMR272, which codes hygromycin resistance.

The plasmid pCMVSHE-PYC2 was generated as follows. The cDNA of pyruvate carboxylase (PYC2, isoenzyme 2) from Saccharomyces cerevisiae was obtained from R. Stucka (Stucka et al., 1991). In order to avoid possible interactions of the yeast vector fragment bordering the coding region, the cDNA was trimmed down to the essential coding sequences by endonuclease restriction and ligation with small PCR fragments according to a procedure well known in the art (FIG. 51).

The modified cDNA was placed under the transcription control of a CMV promoter. The resulting pCMVPYC2 plasmid also contains an ampicillin-resistance gene. It will be clear that other promoters and resistance genes or general selection markers can be used.

FIG. 51 shows the removal of flanking yeast-specific sequences from the 5'- and 3'-regions of the PYC2 gene.

First using PvuII, a 678 bp fragment was cut out from the 5'-end, the missing 381 bp were ligated by means of PCR (polymerase chain reaction) via specific primers, and a HindIII restriction site was built on before the coding sequence.

For the 3'-end, a corresponding procedure was carried out via the ClaI restriction site by removal of 469 bp and ligation with a fragment 176 bp long. The fragment was provided with a HindIII and SmaI restriction site at the 3'-end.

Clone CHO-hGM-CSF-PYC2-4D5 (Bollati Fogolin, 2003) was used for the studies carried out in the present invention. The cell line secretes the recombinant, glycosylated "human granulocyte-macrophage colony-stimulating factor" (hGM-CSF) into the culture medium and exhibits hygromycin resistance up to a concentration of 250 μg mL$^{-1}$.

(3) CHO-hGM-CSF

The cell population that was derived by analogous transfection of the CHO-hGM-CSF cell line with plasmid pHMR272 alone and subsequent selection was used as reference for the PYC2 expressing clone. This mixed population of different individual clones exhibits hygromycin resistance up to a concentration of 250 μg mL$^{-1}$ (Bollati Fogolin, 2003).

(B) Culture Media

For strain maintenance and selection, the above-indicated antibiotics were used in appropriate concentrations.

(1) ProCHO4-CDM

The serum and protein-free medium ProCHO4-CDM (Biowhittaker Europe) which is commercially available was used for the cultivation of the CHO-MUC1 cell line in strain maintenance and small scale fermenter system (1 L, Applikon) for preliminary studies of the effect of the pH tritration agents. The medium has a glucose content of 4.30 gL$^{-1}$ and contains 5.00 gL$^{-1}$ HEPES. It was supplemented with NaHCO$_3^-$ (final 3.78 gL$^{-1}$), glutamine (final 4.1 mM), hypoxanthine (final 0.1 mM) and thymidine (final 0.1 mM). The pH value was adjusted to pH 7.0.

(2) Industrial Production Medium (Roche Diagnostics GmbH)

This medium was prepared according to the instructions with ultrapure water (SQ, Millipore) and supplemented for all cell lines. All media were adjusted to pH 7.0 by titration with 4 M NaOH. Subsequent to sterile filtration (0.2 μm) and sterile test (72 h, RT), these serum-free media were stored for up to one month (4° C.). The glucose concentration of the main fermentation medium is 8.0 gL$^{-1}$. For the feeding method, a medium concentrate with high glucose concentration was used.

(C) Off-Line Analysis (1) Assessment of Cell Number, Viability and Sterility

The sample which were collected daily from the appropriate suspension cultures were examined microscopically for contamination (bacteria, fungi). Cell number and viability were assessed manually (light microscopy) and automatically (ViCell XR, Beckman Coulter, Krefeld). The ratio of live cells was determined using the exclusion method with a 0.5% (w/v) trypan blue solution. In order to identify dead cells, 0.2% trypan blue solution was added to the cell suspension in a mixture ratio of 1:1, carefully mixed and the number of dyed cells was determined by counting eight large squares of a counting chamber according to Neubauer (depth 0.100 mm, haemacytometer) under a light microscope with 100-fold magnification. By subtracting the resulting concentration of dead cells from the concentration of the cells in total, the concentration of viable cells in suspension is determined. Their ratio with respect to the concentration of the cells in total is referred to as viability. This measuring principle was automated in ViCell XR. Mixing with trypan blue and the discrimination between live and dead cell is effected by means of the contrast ratio. To this aim, an integrated camera supplies the corresponding images for the computer-assisted analysis.

(2) Analysis of the Media

Substrate, metabolite and product concentrations contained in the medium are accessible from the cell-free medium supernatants (10 min., 200 g) of the culture using the methods described below. The temporary storage of the cell-free supernatants is carried out at −80° C. If not indicated otherwise, all measurements and calibrations are carried out according to the manufacturer's instructions.

Glucose

In order to evaluate the content of glucose in culture supernatants, an automatic glucose analyser (EBIO Compact, Eppendorf, Hamburg) was used. The measurement is based on a coupled enzymatic electrochemical process wherein the hydrogen peroxide which, in addition to gluconic acid, is released by the immobilized glucose oxidase is measured amperometrically at a Pt/AgCl/Ag electrode. The electrode current resulting from the oxidation of the hydrogen peroxide into oxygen is directly proportional to the hydrogen peroxide concentration and, thus, to the glucose concentration of the sample.

Lactate

Lactate is also quantified according to an electro-enzymatic principle in an analyser (Yellow Springs Instruments, Ohio, USA). By means of immobilized lactate oxidase, lactate is reacted into pyruvate and hydrogen peroxide. The latter can be quantified as in glucose quantification.

Glutamine and Glutamate

The simultaneous quantification of glutamine and glutamate is carried out according to the principle described for glucose quantification using two immobilized enzymes on different sensors. Glutamate oxidase catalyses the reaction of glutamate with oxygen into α-ketoglutarate and hydrogen peroxide with elimination of ammonia. At the glutamine sensor, glutaminase first effects the formation of glutamate which is then reacted in an analogous manner. Thus, the glutamine sensor also detects free glutamate in the solution which is factored in by the analyser.

Osmolality

Osmolality is a measure for the number of dissolved particles per measuring unit of the solvent. According to the definition, deionised water freezes at 0° C. under normal conditions. A related depression of the freezing point of 1.858 K corresponds to an osmolality of 1 osmol/kg. The measurement of osmolality using the freezing point osmometer starts with cooling the sample to −7.0° C. The crystallisation of the subcooled solution is induced by means of a seed crystal and the quantity of heat produced is measured until the freezing point is reached. This difference to the pure solvent water is directly proportional to the osmolality of the sample.

Amino Acids

The concentration of free amino acids in the culture supernatant was determined by reverse-phase HPLC (High Performance/Pressure Liquid Chromatography) (Büntemeyer, 1988). To carry out the analyses, a fully automated HPLC system D450 (Kontron Instruments, Echingen) with two high pressure pumps (Model 420), automatic sampling (Model 460) as well as a fluorescence detector (Model SFM 25) and computer-assisted evaluation unit (KromaSystem 2000, version 1.60) was used. Separation was carried out using a RP$_{18}$, column (Ultrasphere ODS, 150 mm×4.6 mm, particle size 5 μm, Beckman, Munich) with octadecylsilicate as stationary phase. To this, a further RP$_{18}$ column (Hypersil ODS, 10 mm×4.6 mm, particle size 10 μm, Techlab, Erkerode) was proposed in order to increase the dwell time. Prior to separation, the derivatization of the amino acids by ortho-phthaldialdehyde (OPA) (Sigma, Deisenhofen) (Lim, 1987; Büntemeyer, 1991) occurred. The primary amino groups of the amino acids react in alkalic medium (pH>9) with OPA and 3-mercaptopropionic acid to fluorescent isoindol derivatives (FIG. 2.1). Detection was carried out at an emission wavelength of 450 nm subsequent to excitation with light of a wavelength of 340 nm.

The cell-free culture supernatants (500 μl) were mixed with trichloroacetic acid (100 μl, 36% w/v) and the precipitated proteins were sedimented (10 minutes, 15000 g). The intermediate phase was recovered (250 μl) and neutralized (12.5 μl NaOH 1 M). This stock solution was added to the derivatization in suitable pre-dilution and alkalization with sodium borate buffer (0.4 m, pH 9.5), wherein, due to the instability of the isoindol derivatives, the derivatization was carried out only immediately before HPLC separation by automatic addition of the derivatization reagent (50 mg OPA in 1 ml methanol, 100 μl 3-mercaptopropionic acid and 9 ml 0.6 M sodium borate buffer, pH 10.4) to the sample. The gradient used for the HPLC separation of the amino acid derivatives (Büntemeyer, 1991) was run from the more polar (99% v/v 0.1 m sodium acetate pH 7.5, 1% v/v tetrahydrofurane) to the more non-polar buffer (30% 0.085 M sodium acetate pH 5.2, 70% methanol) which allowed to quantify all amino acids with the exception of cysteine and proline. Proline as secondary amine exhibits no reaction and cysteine forms, together with OPA, a non-fluorescent derivative.

(3) MUC1-IgG2a ELISA

The MUC1-IgG2a antibody produced by the CHO-MUC1 cell line cultivated in this study is a representative of the murine immunoglobulin G (IgG) whose H chain is of type y and whose subclass is 2a. It is N-terminally linked to MUC1 whereby the detection of a molecule of this antibody always includes the detection of a molecule of fused MUC1. In order to prevent the detection of incompletely translated product, only cell viabilities of more than 80% were taken into consideration. The quantitative evaluation of MUC1-IgG2a in culture supernatant was carried out by means of ELISA.

The quantification of the MUC1-IgG fusion protein was carried out according to the studies by Link (2003) (Parker, 1990; Link, 2003). 96-well immunoplates (F96 Maxisorp, Nunc, Wiesbaden) were used as adsorbing solid phase for MUC1-IgG quantification by means of ELISA. The catching antibody adsorbed to the solid phase was a commercially available goat anti-mouse IgG (M-8642, Sigma, Deisenhofen) which was obtained by immunisation of goats against murine IgG. The supplied antibody (1 mg) was dissolved in PBS (25 ml, final 40 μg mL$^{-1}$), aliquoted (1 mL) and stored at −20° C. Prior to use, it was diluted in PBS to 3 μg mL$^{-1}$. The supernatants to be quantified as to MUC1-IgG2a as well as a MUC1-IgG2a standard were used as determinable antigens. The standard was pre-diluted to 1 μg mL$^{-1}$ in dilution buffer prior to use in ELISA.

The alkaline phosphatase conjugate goat anti-mouse IgG AP of the catching antibody (A-5143, Sigma, Deisenhofen) which carries alkaline phosphatase (AP) as substrate-reacting enzyme and specifically binds to the heavy y chain of the murine IgG was used as enzyme-marked antibody. It was stored at 4° C. By the alkaline phosphatase, the substrate p-nitrophenol phosphate (pNPP, N-2770, Sigma, Deisenhofen) was reacted into yellow p-nitrophenol which was determined photometrically. The extinction of the resulting staining was evaluated using a spectrophotometric analyser (405 nm, Wallac Victor$^2$, Perkin Elmer Life Sciences, Bad Wildbach).

In order to coat the Maxisorp immunoplates with the catching antibody goat anti-mouse IgG, this was pipetted into each of the wells of the microtitre plate (100 μL per well). Subsequently, the closed test plate was incubated (4° C., 14 h) and after removing the buffer by rapidly turning the microtitre plate upside down and slapping it, it was rinsed with washing buffer (10 times) and tapped dry. In order to block the unspecific binding sites of the catching antibody, blocking buffer was added to each well (200 μL per well) and the covered plate was incubated (37° C., 2 h). The plate was then washed with washing buffer (3 times) and tapped to dry it off.

The cell-free culture samples to be analysed were first centrifuged (15000 g, 3 minutes) and the resulting supernatant was used as product-containing sample for further analysis. A suitable pre-dilution in dilution buffer was carried out in order to obtain comparable resulting intensities from standards and samples for the evaluation of the colour reaction, allowing conclusions with respect to product concentrations. BSA contained in the dilution buffer served as neutralizing agent for unspecific binding sites. For a double-determination of the samples (columns 3-12) and the standard (columns 1 and 2), respectively, 280 μL per well were pipetted into row H of pre-dilution plates (96 wells, Nunc, Wiesbaden) divided into A1 to H12. Subsequently, a 1:2 dilution was carried out step-by-step by transferring 140 μL per step into the wells of the following row which each contained 140 μL of dilution buffer.

The wells of the coated test plate are loaded each with 100 μL of the pre-diluted samples and standards with the dilution increasing with each row in analogy to the pre-dilution plate and the covered plate was incubated (37° C., 1 h).

To balance the spectrometer against a blank sample, two wells (bottom right) were treated only with dilution buffer. Subsequently, after slapping it, the plate was rinsed with washing buffer (10 times) and the plate was tapped to dry it off. In the following step, the enzyme, labelled goat anti-mouse IgG AP antibody was first taken up into dilution buffer in the ratio 1:1000 and, subsequently, pipetted into the wells of the test plate (100 μL per well). Incubation was carried out anew (37° C., 1 h) and the test plate was then washed with washing buffer (10 times) after removing the residue buffer by slapping. Since substrate pNPP is sensitive to light, all following steps were carried out in quick succession in the dark. The reaction of p-nitrophenyl phosphate into yellow product by the antibody-bound alkaline phosphatase was induced by adding substrate to each well of the test plate (100 μL). The plate was incubated in darkness (room temperature, 10-30 minutes) until an intensive yellow staining (extinction of 0.7-0.8) was observed in the well with the reacted standard. The evaluation of the intensities of the staining was carried out by spectrophotometry at 405 nm.

(4) hGM-CSF EILSA

Competitive ELISA (Bollati Fogolin, 2002) was used to detect the cytokine hGM-CSF. 96-well immunoplates (F96 Maxisorp, Nunc, Wiesbaden) were used as adsorbing solid phase for quantification of hGM-CSF by ELISA. Recombinant, unglycosylated HGM-CSF from *E. coli* which is commercially available (Leucomax, active ingredient: molgramostim, Schering-Plough corporation Kenilworth, N.J., USA) was used for coating the Maxisorp plates and as concentration standard. A monoclonal mouse-anti-GM-CSF antibody (M7E10) (Etcheverrigaray, 1998), which was kindly provided by Ms. Bollati Fogolin, was used as primary antibody. This antibody is directed against an hGM-CSF domain which is accessible independently of the glycosylation status of the protein. The enzyme labelled antibody was a peroxidase conjugate goat-anti-mouse-IgG-HRP that carries horseradish peroxidase as substrate-reacting enzyme and specifically binds to the Fab$_2$ fragment of the murine IgG primary antibody (Dianova 115-035-072, 0.8 mg mL$^{-1}$). The substrate 1,2-phenylenediamine-dihydrochloride (OPD, Fluka) was reacted into an orange end product by horseradish peroxidase after the enzyme reaction was stopped. The extinction was evaluated by photometry. The extinction of the resulting staining was read in spectrophotometric analyser (492 nm, measuring time 1 second/well, Wallac Victor$^2$, Perkin Elmer Life Sciences, Bad Wildbach).

In order to coat the Maxisorp immunoplates with hGM-CSF from *E. coli* as competitor to glycosylated hGM-CSF from the fermentation supernatant, the first was pipetted into each well of the microtitre plate (per well 16.5 ng in 100 µL coating buffer). Subsequently, the closed test plate was incubated in an atmosphere saturated with water vapour (37° C., 1 h, subsequently 4° C., 14 h) and after removing the residue buffer by slapping rinsed with washing buffer (10 times) and tapped to dry off. In order to determine the standard curve, dilutions of the unglycosylated hGM-CSF standards in the range of 200-0.195 ng mL$^{-1}$ were carried out in dilution buffer. The samples from the culture supernatants were also diluted sequentially 1:2 in dilution buffer and pipetted together with the prepared standards into the wells of the coated microtitre plate (100 µL per well). Plain dilution buffer is used as control for complete binding without competition of hGM-CSF-containing standard or culture supernatant. Then, the primary antibody M7E10 (1:100 000 in dilution buffer, 100 µL per well) was added to the wells of the plate loaded with samples and standards and it was incubated (37° C., 1 h). After removing the solution and washing the plate with washing buffer (7 times), an incubation was carried out (37° C., 1 h) with conjugate antibody (1:5000 in dilution buffer, 100 µL per well). After washing the plate (7 times), the enzyme reaction was started by adding the freshly prepared dye solution. After 15 minutes incubation, the reaction was stopped by adding stop solution (50 µL per well) and the resulting extinction is evaluated at a wavelength of 492 nm (per 1 s).

(5) Flow Cytometric Cell Analysis

The correspondingly prepared samples were measured using FACSCalibur Calibur flow cytometer (Becton Dickinson, San Jose, Calif., USA) and CellQuest software version 3.3 (both Becton Dickinson, San Jose, Calif., USA). Off-line analysis of the data was carried out using CellQuest 3.3, Modfit and FCSassist 1.0 on a G4 Apple Macintosh computer.

Cell Cycle Phase Distribution

To determine the individual cell phases (G1, S, G2, M), the culture sample in form of a single cell suspension was liberated from supernatant (200 g, 7 min) and washed twice in ice-cold PBS (200 g, 7 min). The resulting pellet was resuspended dropwise in a mixture (−20° C.) of 80% (v/v) methanol (high-grade, Merck) under intensive agitation and incubated (4° C., 2 h—2 months). The cells were then pelleted (200 g, 7 min), subsequently, they were resuspended in a mixture of 0.1% (w/v) saponine (Roth) in PBS and washed twice (200 g, 7 min). Resuspension of 4×10$^6$ cells in 1 mL dye solution (0.1% w/v saponine, 1 g mL$^{-1}$ RNase S (Sigma), 0.02 mg mL$^{-1}$ propidium iodide (Sigma)) and incubation (RT, 30 min) resulted in a pink-stained cell pellet. First the enzymatic degradation of the RNA was stopped by storage on ice and, then, the stained cells were subjected to flow cytometry. Measuring was carried out according to the manufacturer's instructions and protocols of the relevant literature regarding flow cytometry (Melamed, 1990; Givan, 1992; Shapiro, 1994; BD-Biosciences 2000).

Intracellular pH Value

The intracellular pH value (pH$_i$) of animal cells is related to different cellular functions. Modifications in cell growth, metabolism and protein production as well as in enzyme activities, transport mechanisms, proliferation induction and maintenance energy requirement involve variances in pH$_i$ (Madshus, 1988; Grinstein, 1989). Thus, the control of pH$_i$ is of fundamental biological significance for the cell. The isoelectric points of many biologically important macro-molecules in the cell are near the physiological value of pH 7 so that comparatively small modifications in proton concentration can have major effects on the conformation and interaction of proteins and nucleic acids. To prevent an acidification of cytosol, the H$^+$ protons are directly removed from the cell or hydrogen carbonate ions HCO$_3^-$ are introduced into the cell in order to neutralize the protons in cytosol. For this pH$_i$ control, different mechanisms are available in animal cells (Madshus, 1988; Reusch, 1995): Na$^+$/H$^+$ exchanger, Na$^+$ dependent and independent Cl$^-$/HCO$_3^-$ antiporter, Na$^+$/HCO$_3^-$ symporter, H$^+$ translocating ATPases (proton pumps).

In contrast to the external pH (pH$_e$) which, in animal cell cultures, is in the range of 6.6-7.4, the above-mentioned mechanisms allow that the cell can actively maintain internal pH values which deviate from the external values by 0.1-0.5 pH units. The cell organelles have distinctive pH values in order to fulfil their biological functions. Furthermore, sensitively controlled pH gradients are important for posttranslational protein sorting and processing. Dysfunctions of this intracellular control may occur in cell cultures due to accumulation of organic acids and bases, such as e.g. lactate, ammonium or CO$_2$, in the culture medium. Correlations between pH$_i$ and cell cycle phases have also been described. Thus, in general, a more alkaline pH value is measured in the cytosol if the cell is in a metabolically active phase of the cell cycle (S and/or G2 phase, respectively) (Welsh and Al-Rubeai, 1996).

The intracellular pH value can be determined flow cytometrically using a pH-sensitive fluorescence dye that is stimulated in the cell. The fluorescence dye used in the present invention 5'(and 6')-carboxy-10-dimethylamino-3-hydroxyspiro[7H-benzo[c]xanthene-7,1'(3'H)-isobenzofuran]-3' one, often referred to as carboxy seminaphtorhodafluor acetoxymethyl ester or simply carboxy-SNARF-1-AM, in the following referred to as SNARF-1) is a weak acid with a pK$_a$ value of 7.3-7.4 at 37° C. and, upon excitation with light of a wavelength of 488 nm, exhibiting two fluorescence signal maxima of different wavelength (FL2: 580 nm, FL3: 640 nm, FIGS. 3-7) (C-1270, Molecular Probes). The relative correlation of these emission maxima shows a pH-dependent shift and, thus, allows to measure pH$_i$ independently of the amount of dye excited in the cell.

Being an acetoxymethyl derivative, the fluorescence dye is cell membrane dependent and is hydrolysed in the cytosol of unspecific esterases. This free-form fluorophor remains in the cell and can be exited for emission in the cell. In order to determine the intracellular pH value, a calibration curve must be established by implication of known pH$_i$ values. It must be based on the same cell population from which the sample to be measured is derived (Owen, 1991; Owen, Carango et al. 1992). In this context, the maintenance of the reactor conditions during the preparation of the samples and the selection of the calibration method are of equal importance (Cherlet, Franck et al., 1999; Bond and Varley, 2005; Jockwer, Gätgens et al., 2005) in order to obtain representative pH$_i$ values.

In the present invention, the pseudo zero-point calibration method which is based on the deflection of the stationary pH$_i$ by adding weak acids and bases in known mixture ratios to the cells was used to calibrate the intracellular pH value. According to this, the resulting fluorescence ratio reflects the new pH$_i$. If the molar concentration of the mixture of a weak acid and base was sufficiently high, a further addition of the same mixture will not alter either the fluorescence ratio or the pH$_i$, so that the deflected pH$_i$ represents a new pseudo zero-point satisfying the equation 3-3. If concentrated mixtures of different molar ratios of weak acid to weak base are added to the cells loaded with the pH-sensitive fluorescence dye are, it is possible to establish a calibration curve by plotting the pseudo zero-pH against the fluorescence ratios obtained. This calibration method can be reproduced flow-cytometrically and requires only little time for implementation, it is independent of the intracellular $K^+$ concentration and, thus, suitable for analysis in the course of the fermentation process.

For representative sampling from bioreactors (with pressure blanketing) and cultivation with defined compositions of dissolved gasses, a specific sampling (Jockwer, Gätgens et al., 2005) was developed which is the result of the present invention. The parameters which are relevant for the $pH_i$ during the period of dye absorption such as $pCO_2$, pressure, pH and temperature are entered into this device so that the cell sample is stained under reproducible reactor conditions. Thus, the $pH_i$ measured in said manner represents the real conditions in the bioreactor better than conventional methods. Together with the stained sample, an unstained sample of the same population was studied as a control under identical conditions.

Solutions and Buffers

| | | |
|---|---|---|
| HEPES buffer (N-[2-hydroxyethyl]piperazine-N'-[2-ethanesulfonic acid] | | (10 mM) |
| 2.383 g $L^{-1}$ HEPES | | (10 mM) |
| 7.802 g $L^{-1}$ NaCl | | (133.5 mM) |
| 0.298 g $L^{-1}$ KCl | | (4 mM) |
| 0.166 g $L^{-1}$ $NaH_2PO_4 \cdot H_2O$ | | (1.2 mM) |
| 0.144 g $L^{-1}$ $MgSO_4$ | | (1.2 mM) |
| 1.981 g $L^{-1}$ α-D-glucose | | (11 mM) |
| 0.294 g $L^{-1}$ $CaCl_2 \cdot 2H_2O$ | | (2 mM) |
| pH 7.4, sterile filtration, storage at 4° C. | | |
| dye SNARF-1 (carboxy seminaphtorhodafluor acetoxymethyl ester) | | (2 mM) |
| 50 µg | carboxy-SNARF-1-AM (C1272, Molecular Probes, Leiden, The Netherlands) | |
| 44 µl | DMSO | |
| Butyric acid BA (n-butyric acid) | 1M 4.6 mL butyric acid 10.9M ad 50 mL $H_2O$ pH 7.4, sterile filtration, storage at 4° C. | ($pK_a$ = 4.82, Sigma) |
| trimethylamine TMA | 1M 12.3 mL trimethylamine 4.06M ad 50 mL $H_2O$ pH 7.4, sterile filtration, storage at 4° C. | ($pK_a$ = 9.8, Sigma) |
| HDFBS | 10% (v/v) dialysed FBS in HEPES buffer | |

TABLE 1

Pseudo-zero calibration solutions (Chow, Hedley et al., 1996)

| 6-fold concentrate BA/TMA [mM] | 0.5 log ([BA/TMA]) | BA [µL] | TMA [µL] | HDFBS [mL] |
|---|---|---|---|---|
| 6/96 | −0.6 | 60 | 960 | 8.98 |
| 6/24 | −0.3 | 60 | 240 | 9.70 |
| 6/6 | 0 | 60 | 60 | 9.88 |
| 24/6 | 0.3 | 240 | 60 | 9.70 |
| 96/6 | 0.6 | 960 | 60 | 8.98 |

Prior to sampling from the relevant culture system by means of the sampling apparatus developed (Jockwer, Gätgens et al., 2005) the 6-fold concentrated pseudo-zero calibration solutions (Table 3-1) were placed into measurement tanks of the flow cytometer (200 µL each), the tanks were closed in a gas-tight manner and stored in a cool place (4° C.). The two calibration solutions of the highest and of the lowest mixture ratio of acid to base were prepared twice each for the adjustment of the measuring ranges of the flow cytometer. For the sample that was to be determined, 3 measuring tanks were treated with HDFBS (200 µL per tank) in the same manner. Prior to collecting the sample from the culture medium, 22 µL of the fluorescence dye were placed into the pre-incubated sampling apparatus (37° C.). The staining of the cells in esterase-free culture medium was started by mixing the cell suspension during the isobaric and gas-tight sampling and was continued in darkness under agitation (appropriate reactor pressure, 25 min, 37° C.). After 15 minutes incubation, the temperature of the calibration and measuring solutions, still sealed and gas-tight, is adjusted to reactor temperature (water bath, 37° C.). Once the incubation of the cells with the fluorescence dye under reactor conditions is terminated, the cells are immediately subjected to pressure control and dissolved gas analysis (Compact 3, Roche Diagnostics GmbH) and subsequently suspended in the corresponding measuring and calibration solutions (200 µL each) to be measured after 10 seconds by means of a flow cytometer (FACSCalibur, Becton Dickinson). For this purpose, first a repeat determination of the sample to be determined is carried out in measuring buffer (HDFBS) and only then the stained cells are measured sequentially in the corresponding measuring buffers. The pH value of each sample is measured (Compact 3, Roche Diagnostics GmbH) immediately after the flow cytometric measurement of this sample.

The time elapsing between the opening of the sampling apparatus and the dissolved gas analysis of stained and unstained cells is less than 5 seconds, the time elapsing until the flow cytometric measurement is terminated is less than 90 seconds. Between the termination of the fluorescence analysis and the determination of the external pH value, 15 seconds elapse. This procedure in combination with the (pressure maintaining) sampling apparatus allows to determine a representative $pH_i$ value (see also Chapter 4.2) (Chow, Hedley et al., 1996).

Measurement

The flow cytometric measurement of the fluorescence to determine the $pH_i$ values is carried out according the manufacturer's instructions for the device (FACSCalibur, Becton Dickinson), the dye (Carboxy-SNARF1-AM, Molecular Probes, Leiden, The Netherlands) and according to the relevant literature (Chow and Hedley, 1997).

The basic settings which must be optimized for each sample are listed below:
 measurement window 1: SSC/FSC (scatter diagram, scaling double linear, total cell population)
 measurement window 2: counts (linear)/FL2 (log.) (histogram)
 measurement window 3: counts (linear)/FL3 (log.) (histogram)
 measurement window 4: counts (linear)/fluorescence ratio (FL2/FL3)

Dead cells, agglomerations and insufficiently stained cells were excluded from the measurement by suitable limiting values. Since it is not possible to implement measurement window 4 in real time with the measuring device used, the fluorescence ratio is calculated using the program FCSassist (Becton Dickinson). The program CellQuest 3.3 (Becton Dickinson) was used for the evaluation. Plotting the "mean fluorescence intensity ratio" (MFI) against each induced $pH_i$ value according to equation 3-3 results in the calibration curve which allows to calculate the $pH_i$ of the sample.

(6) Dissolved Gases, pH Value and Depending Parameter

The blood gas analyzer AVL Compact 3 (Roche Diagnostics GmbH) is used for direct evaluation of the dissolved gases $CO_2$ and $O_2$, the pH value and the calculation of the dependent concentrations of hydrogen carbonate and "total $CO_2$" from the cell-containing culture samples (>55 µL, 37° C.) according to the manufacturer's instructions (Roche 2003). After placement of the relevant physiological sample, the device automatically determines the above-mentioned parameters. For this purpose, the following miniaturised electrodes are installed in a tempered measuring chamber:

pH reference electrode
pH measuring electrode
$pO_2$ measuring electrode
$pCO_2$ measuring electrode The direct $pCO_2$ measurement is a modification of pH measurement. Via a membrane that is impermeable to ions, only gaseous $CO_2$ gets into the measuring buffer the pH of which is modified by dissociated $CO_2$, is measured and, after amplification, is indicated as $pCO_2$ value [mmHg]. The conversion into [%] $pCO_2$ and/or $pO_2$, respectively, is carried out separately after the automatic measurement of the atmospheric pressure which is carried out for each sample measurement. Calibration gases and buffer solutions supplied to the device allow for automated calibration and cleaning according to defined cycles.

(D) Cultivation of Animal Cells

All operations were carried out in compliance with the standard operation regulations and directives for the handling of genetically modified organisms, security level S1.

(E) Bioreactor Cultivation

All tests were carried out in commercially available stirred reactors with a working volume of 1 L (Applikon Biotek, Knüllwald) and 10 L (B. Braun Biotech International, Melsungen), respectively, under sterile conditions. All measured values were transferred to the process computer via measurement amplifiers and analog-to-digital coder (SMP Interface, Siemens) and processed using the process control software LabView (National Instruments, USA) and stored. The following process parameters were identical in both systems throughout the cultivation period and were constantly monitored.

standard fermentation conditions (1 L & 10 L reactors)
stirring velocity 200 rpm
temperature 37° C.
dissolved oxygen saturation 40% (in relation to air)
pH 7.0
ratio gassing (1 L reactor: 2.4-5.0 $Lh^{-1}$; 10 L reactor: 30-45 $Lh^{-1}$)

The mixture of high-grade gas fractions of nitrogen ($N_2$), oxygen ($O_2$) and carbon dioxide ($CO_2$) for the maintenance of the controlled concentration of dissolved oxygen $pO_2$ with constant gassing rate is referred to as "ratio mode".

(1) Measurement of the Process Parameters

Dissolved Oxygen ($pO_2$)

The in situ measurement of the concentration of dissolved oxygen in the different aqueous solutions was carried out by means of oxygen electrodes according to Clark (InPro 6000, Mettler Toledo, Urdorf, CH).

Dissolved Carbon Dioxide ($pCO_2$)

The in situ measurement of the concentration of dissolved carbon dioxide in the different aqueous solutions and during fermentation was carried out by means of the commercially available probe YSI 8500, Yellow Springs Instruments (Yellow Springs, USA) and/or, for comparison measurements in the cell-free system, by means of the probe InPro 5000, Mettler Toledo (Urdorf, CH). Both devices were operated in display mode [% $CO_2$]. In this context, the indication [%] refers to the equilibrium conditions between $CO_2$ rate [%] in the gassing mixture and aqueous culture medium under standard fermentation conditions (37° C.) which were set under calibration conditions.

The calibration conditions used and the display values of $CO_2$ [%] allow the calculation of the equilibrium concentrations of dissolved $CO_2$ during the process. As in other publications in this technical field, the term $pCO_2$ [%] is used herein as a synonym for "dissolved concentration" and "partial pressure" of $CO_2$ though the absolute concentrations of $CO_2$ actually dissolved in the culture medium have to be calculated on its basis (Zhangi, Schmelzer et al., 1999; Pattison, Swamy et al., 2000; Schmelzer, de Zengotita et al., 2000). 1% saturation corresponds to approximately 7.5 mm Hg, 10% correspond to approximately 75 mm Hg.

Exhaust Gas Analysis

Oxygen and carbon dioxide quantification in the nonaqueous exhaust air of both processes is carried out using the exhaust analyzer Xentra 4900 (Servomex, Hamm). The oxygen rate is measured paramagnetically (0-100% v/v), the carbon dioxide rate is measured by infrared spectroscopy (0-25% v/v).

The pH value is measured using a single-rod pH measurement assembly with gel electrolyte (Applisens, The Netherlands). In contrast to conventional pH electrodes with liquid electrolyte, the pH electrode used exhibits, after autoclaving, an internal pressure which considerable reduces the permeation of the glass membrane by extraneous substances and the electrode drift associated therewith. Prior to installation and sterilisation, the pH electrode is calibrated to two defined pH values (pH 4.00 and pH 6.96) at 37° C. according to the manufacturer's instruction. Prior to starting the fermentation, correct operability was ensured by external comparison measurements with the blood gas analyzer (Chapter 3.3.4). Process overpressure is measured by means of two pre-pressurized gel-filled electrodes installed in the cover of the culture vessel (B. Braun International, Melsungen; Bioengineering AG, Wald, CH). The temperature in the culture vessel is measured at all operation stages by means of a PT 100 resistance thermometer of the reactor manufacturer installed in the probe ring.

(F) Mathematical Methods

For cultivation and fermentation, parameters allowing the description of growth and metabolic rates are determined by analytic methods. Cell densities are indicated in animal cell culture in contrast to microbial systems. In general, dry biomass is not of interest.

Viability describes the rate of viable cell density ZDL with respect to total cell density ZDG:

$$Viabilität = VIA = \frac{ZDL}{ZDG} \cdot 100\% \qquad \text{(equation 3-6)}$$

All cell density dependant values determined in the present invention refer to the viable cell number ZDL. It can be assumed that the contribution of non-viable cells to metabolism is not substantial. Viability is a measuring value with respect to the state of a culture. The growth rate WTR indicates the number of divisions taking place in one time interval.

$$v = WTR = \frac{n}{t_2 - t_1} \qquad \text{(equation 3-7)}$$

WTR=cell division rate, $h^{-1}$
n=number of division steps during period of time $t_2-t_1$
t=time, h The cell number increase is calculated based on the number of division steps as follows:

$$N_2 = N_1 \cdot 2^n \quad \text{(equation 3-8)}$$

N=number of cells, total number of cells or number of viable cells
n=number of division steps Solved for n and substituted into equation 3-8, the equation for the growth rate reads:

$$WTR = \frac{\log N_2 - \log N_1}{\log 2 \cdot (t_2 - t_1)} \quad \text{(equation 3-9)}$$

The specific growth rate μ is calculated by correlating growth velocity with viable cell density.

$$\mu = \frac{1}{ZDL} \cdot \frac{d(ZDL)}{dt} \quad \text{(equation 3-10)}$$

μ=specific growth velocity, $h^{-1}$
ZDL=cell density, viable, cells $mL^{-1}$
t=time, h For the increase in the number of viable cells it is true that:

$$ZDL_2 = ZDL_1 \cdot e^{\mu \cdot (t_2 - t_1)} \quad \text{(equation 3-11)}$$

Thus, for μ it is true that:

$$\mu = \frac{\ln ZDL_2 - \ln ZDL_1}{t_2 - t_1} \quad \text{(equation 3-12)}$$

Specific substrate consumption rates can easily be calculated for discontinuous processes. For pulsed feed (bolus) in fed-batch processes, the same correlations can be used since the duration of feeding (<15 s in the experiments of the present invention) and, thus, substrate consumption by the cultured cells during this period of time decreases towards zero. It is however necessary to include any modifications in substrates, metabolites and fermentation volumes resulting from feeding and to adjust them mathematically. (Cell-)specific consumption and formation rates are often the only factors allowing the comparison of different processes.

It is true that:

$$qS = \frac{dS}{dt} \cdot \frac{1}{ZDL} \quad \text{(equation 3-13)}$$

qS=specific substrate consumption rate, mol
S=substrate concentration, mol $L^{-1}$
t=time, h
ZDL=cell density, viable, cells/mL The mean cell number in the period of time Δt ($t_2 - t_1$) is determined by the logarithmic mean if the time interval between two sampling points is sufficiently long:

$$\overline{ZDL} = \frac{ZDL_2 - ZDL_1}{\ln ZDL_2 - \ln ZDL_1} \quad \text{(equation 3-14)}$$

$\overline{ZDL}$=mean of cell number, viable, cells $mL^{-1}$

The integration of equation 3-13 under consideration of equation 3-14 results in:

$$qS = \left(\frac{S_2 - S_1}{t_2 - t_1}\right) \cdot \frac{1}{\overline{ZDL}} \quad \text{(equation 3-15)}$$

The specific product formation rate is calculated analogously to the substrate consumption rate:

$$SPR = qPRO = \left(\frac{PRO_2 - PRO_1}{t_2 - t_1}\right) \cdot \frac{1}{\overline{ZDL}} \quad \text{(equation 3-16)}$$

SPR=qPRO=specific product formation rate, g $cell^{-1} \cdot h^{-1}$
PRO=product concentration, g $L^{-1}$ Yield Coefficient The correlation between consumption and formation rates of substrates and products, respectively, is indicated by the yield coefficient Y.

$$Y(A/B) = \frac{qA}{qB} \quad \text{(equation 3-17)}$$

Y(A/B)=yield coefficient for A in correlation to B
qA=cell-specific rate for substance A, mol $cell^{-1} \cdot h^{-1}$
qB=cell-specific rate for substance B, mol $cell^{-1} \cdot h^{-1}$ Chemostat For a continuous process, the volume flow into the reactor is equal to the volume flow from the reactor. In chemostat processes, the cell size distribution in the volume flow extracted corresponds to the cell size distribution in the reactor. Culture volume is constant. When calculating the rates, flow rate D has to be taken into consideration.

$$D = \frac{F}{V_R} \quad \text{(equation 3-18)}$$

D=flow rate, $h^{-1}$
F=flow, L
$V_R$=culture volume, L

Mean retention time of a volume element in the reactor is defined as retention time τ.

$$\tau = \frac{V_R}{F} \quad \text{(equation 3-19)}$$

τ=retention time, h

Thus, flow rate is the reciprocal of retention time.

Consequently, for chemostat, it applies that, in equilibrium, growth rate is adjustable via flow rate, it is true that: μ=D.

With respect to substrate consumption in continuous systems with constant culture volumes, it is true that:

$$\frac{dS}{dt} = D \cdot (S_i - S_0) - Q_S \quad \text{(equation 3-20)}$$

$S_i$=substrate concentration in the culture, mol L$^{-1}$
$S_0$=substrate concentration in the feed, mol L$^{-1}$
$Q_s$=volumetric consumption rate, mol L$^{-1}$
and consequently:

$$Q_S = D \cdot (S_i - S_0) - \left(\frac{S_1 - S_2}{t_2 - t_1}\right) \quad \text{(equation 3-21)}$$

In order to calculate the specific substrate consumption rate, the number of cells in form of the logarithmic mean is additionally included in the calculation.

$$qS = \frac{1}{ZDL} \cdot \left[D \cdot (S_i - S_0) + \left(\frac{S_2 - S_1}{t_2 - t_1}\right)\right] \quad \text{(equation 3-22)}$$

qS=specific substrate consumption rate, mol cell$^{-1}$·h$^{-1}$
$S_{1,2}$=substrate consumption for $t_{1,2}$, mol L$^{-1}$
Specific productivity is calculated analogously to the substrate consumption rate:

$$qPRO = \frac{1}{ZDL} \cdot \left[D \cdot PRO + \left(\frac{PRO_2 - PRO_1}{t_2 - t_1}\right)\right] \quad \text{(equation 3-23)}$$

qPRO=specific product forming rate, g cell$^{-1}$·h$^{-1}$
$PRO_{1,2}$=product concentration for $t_{1,2}$, g L$^{-1}$ The instantaneous space-time yield in continuous processes is calculated as follows:

$$RZA = \frac{PRO \cdot D}{V_R} \cdot 24 \quad \text{(equation 3-24)}$$

RZA=space-time yield, gL$^{-1}$·d$^{-1}$
Oxygen Uptake Rate OUR

Due to the relatively low growth rates of animal cell cultures, the high volume flows used in the present invention for gassing the culture and the high control performance of the developed PID controller for dissolved oxygen, it is possible to assume equilibrium conditions for oxygen balancing (Frahm, Blank et al., 2002). Thus, the oxygen uptake OUR can be equalised to the oxygen transfer rate OTR for transfer from the gas phase into the liquid phase and results from equation 3-25, $$OUR = OTR = k_L^{O_2} a \cdot (c_{in}^{O_2} - c_1^{O_2}) \quad \text{(equation 3-25)}$$

$k_L^{O_2}a$=volume-related oxygen transfer coefficient, h$^{-1}$
$c_{in}^{O_2}$=oxygen concentration in the gassing mixture, mol·L$^{-1}$
$c_1^{O_2}$=controlled concentration of dissolved oxygen, mol·L$^{-1}$ The concentration of dissolved oxygen and dissolved carbon dioxide and the oxygen and carbon dioxide concentrations of the gassing mixture are control and correcting variables, respectively, and are registered by the process control system. The volume-related oxygen transfer coefficient was determined earlier for the relevant process conditions by experiment.
Carbon Dioxide Evolution Rate CER Due to the controlled pCO$_2$ values and simultaneous pH control in the culture medium, CO$_2$ is not accumulated in the culture medium. Thus, the balance can be established analogously to dissolved oxygen balance (Frahm, Blank et al., 2002).

$$CER = CTR = 0.89 \cdot k_L a^{O_2} \cdot (c^{*CO_2} - c_1^{CO_2}) \quad \text{(equation 3-26)}$$

with
$k_L a^{CO_2} = 0.89 \cdot k_L a^{O_2}$=volume-related carbon dioxide transfer coefficient, h$^{-1}$
$c^{*CO_2}$=saturation concentration of carbon dioxide in the medium, mol L$^{-1}$ (calculated on the basis of the carbon dioxide concentration of exhaust air)
$c_1^{CO_2}$=controlled dissolved carbon dioxide concentration, mol·L$^{-1}$
Respiratory Quotient RQ The correlation of cell-specific carbon dioxide evolution rate qCER with cell-specific oxygen uptake rate qOUR is referred to as respiratory quotient RQ.

$$RQ = \frac{qCER}{qOUR} \quad \text{(equation 3-27)}$$

RQ=respiratory quotient
qCER=cell-specific carbon dioxide evolution rate, mol
qOUR=cell-specific oxygen uptake rate, mol cell$^{-1}$·h$^{-1}$ Example 2

Optimization of pCO$_2$-Associated Process Parameter

In industrial cell fermentation facilities there are hydrostatic pressures up to 350 mbar in the bottom region (filling point/level 3.5 m) due to the different reactor heights of stirred reactor. Due to reasons of sterility, the fermenters are additionally subjected to pressure blanketing involving overpressures of up to 300 mbar so that in production fermenters of 10 m$^3$ working volume total overpressures of up to 650 mbar could occur in the bottom region. With this overpressure, the CO$_2$ which is produced by the cells accumulates in the medium and can reach inhibiting levels with high density fermentations if the dissolved carbon dioxide discharge has not been optimized via gassing.

For the simulation of the production scale and for the uncoupled analysis of the involved parameters pressure and content of the dissolved carbon dioxide—synonymously referred to as pCO$_2$—with bioprocesses involving animal cells, a controller system has been established in analogy to the concentration of dissolved oxygen pO$_2$. In this context, the control of the content of the dissolved carbon dioxide in the medium should be possible under different pressure conditions, the correcting variable of the pCO$_2$ control system being transferable to bioreactors. Thus, gassing rates, stirring velocities and culture medium were based on industrial parameters.
(A) Control of the Content of the Dissolved Carbon Dioxide in the Culture Medium
(1) Set-Up and Procedure of the pCO$_2$ Control According to standard means, the reaction systems used were supplied with submersible ratio gassing. For the pCO$_2$ control, their CO$_2$ mass flow controllers (MFC, Type Brooks 5850 E CO$_2$, 0-5 L·h$^{-1}$) were actuated by implemented PID controllers in the process control system LabView (Texas Instruments). In addition, only with the 10 L stirred reactor an N$_2$ mass flow controller (Brooks 5850 TR N$_2$, 0-15 L·h$^{-1}$) was installed in the gassing section so that the gassing volume flow rate for pCO$_2$ saturation can be increased from 30 L·h$^{-1}$ to a maximum of 45 L·h$^{-1}$. The measurement of the control variable pCO$_2$ in the medium was carried out by means of an in situ pCO$_2$ probe YSI 8500 (Yellow Springs Instruments) every 15 seconds discontinuously (chapter 3.5.3.2).

Figure 1:
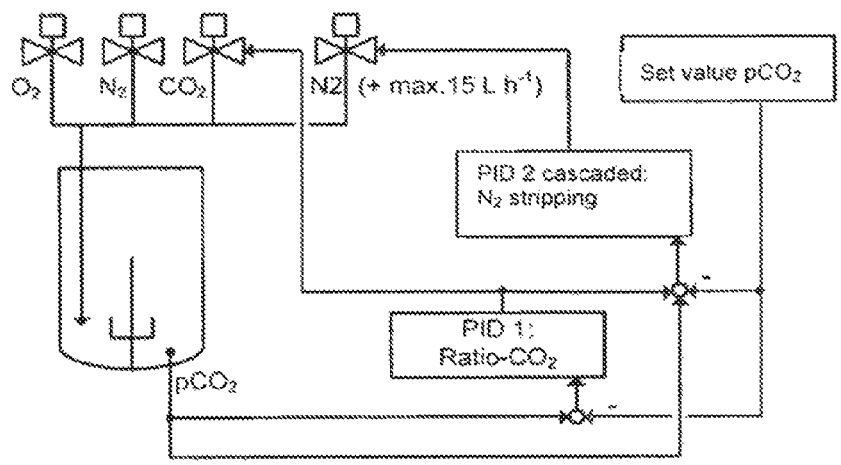
FIG. 1: Schematic control loop of the cascaded $pCO_2$ controller developed

The PID controllers implemented for the control variable in the process control system (LabView, National Instruments, USA) pCO$_2$ work in a cascaded manner (FIG. 1). In the case of a positive deviation from the pCO$_2$ set value, the CO$_2$ content in the ratio gassing is reduced correspondingly by the controller PID 1 (FIG. 1). If, despite the completely closed CO$_2$ MFC, the controller PID 1 does not successfully control the pCO$_2$ set value in the case of a positive deviation (e.g. by produced CO$_2$ of the cells), the cascaded controller PID 2 actuates an additional N$_2$ mass flow controller and appropriately increases the total volume flow rate of the gassing by 15 L·h$^{-1}$ at the most (FIG. 1).

Thus, the pCO$_2$ controller described herein is suitable for control of a set value for the concentration of dissolved carbon dioxide. By means of this pCO$_2$ controller it is now possible to adjust defined pCO$_2$ values during the whole culture process and to analyse their effect on the cultivated cells. According to Henry's Law, the solubility of a gas in liquid is proportional to its partial pressure in the gas phase above. Due to the controller, accumulation of CO$_2$ in the medium is possible by increasing the CO$_2$ ratio in the supply air. With the cultivation period progressing and the cell density in the reactor increasing, the ratio of CO$_2$ produced by the cells increases in the medium. Consequently, the controller reacts by reducing the CO$_2$ ratio in the supply air by the controller. If the volumetric carbon dioxide evolution rate (CER) of the cultivated cells is so high that by a complete reduction of the CO$_2$ ratio in the supply air down to naught the control variable of pCO$_2$ can no longer be reached, the cascaded controller increases the total volume flow of the gassing and, thus, the transfer of CO$_2$ from the liquid phase into the gas phase.

(2) Control Performance of pCO$_2$ and pO$_2$ Control

The increased gas volume flow by the addition of nitrogen in the supply air for an improved discharge of CO$_2$ takes effect as a disturbance variable on oxygen control. By means of the control of the set values shown in the following, the suitability of the pCO$_2$ control together with the pO$_2$ control was analysed both in the 1 L and in the volume. The interaction of the controllers with the pH controller using different titration agents is described below.

The initial parameters of the controller settings were determined according to the recommendations by Ziegler and Nichols (Rake, 1993). For this purpose, the PID controllers of both control systems were configured as simple P controllers (hold-back time T$_V$=0, reset time T$_N$=∞). Variation of the proportional region X$_P$ up to the critical system enhancement of the respective control system results in X$_{P, crit}$. The period of controlling oscillation with X$_{P, crit}$ corresponds to the time T$_{crit}$.

TABLE 2

Recommended controller parameters according to Ziegler and Nichols at stability margin

| PID ratio | setting value |
|---|---|
| P | X$_P$ ≈ 1.7 X$_{P, crit}$ |
| I | T$_N$ ≈ 0.5 T$_{crit}$ |
| D | T$_V$ ≈ 0.12 T$_{crit}$ |

By means of an appropriate control of the set values (Table 2) of both control systems, the quality of control for the use in fermentations of animal cells was optimized. Both control systems work independently from one another with minimal initial oscillating time and control deviation. It was possible to minimise the effect of the increased volume flow on the control of the dissolved oxygen with increased CO$_2$ discharge (FIG. 4-2 and FIG. 4-3).

TABLE 3

Set value profile for the qualification of control in FIG. 2 and FIG. 3

| set value | | time |
|---|---|---|
| pCO$_2$ [%] | pO$_2$ [%] | [h] |
| 5 | 40 | |
| 15 | 40 | |
| 15 | 50 | |
| 10 | 30 | |
| 5 | 40 | ↓ |

The absolute control deviation for dissolved oxygen in the case of set value variances (which do not occur in that manner under cultivation conditions) in processes with low overpressure (50 mbar) is less than 2%: Analogously, the control deviation for the dissolved carbon dioxide ratio is <1% (absolute) with set value variances of absolute 5-10%, which are unusual in fermentation processes (FIG. 2). Also in the case of a reactor involving pressure blanketing (750 mbar) for the simulation of high filling levels in industrial production facilities and the thus increased solubilities of CO$_2$ and O$_2$ in the liquid phase, the quality of the implemented control is sufficient for animal cell culture processes (FIG. 3).

With the set value control performed according to Table 3, the dissolved oxygen value alone temporarily exceeded the set value (<4% absolute) if the total volume flow is increased for discharge of the dissolved CO$_2$ (FIG. 3). The control of pCO$_2$ with deviations of <1% absolute was very exact. Due to a time-pending control of the set value of the pCO$_2$, it was possible to reproduce the defined profiles from production fermenters onto a small scale.

In the following the pCO$_2$ and pO$_2$ controllers described herein were optimized for the decoupled control in combination with the implemented overpressure controller in order to be able to reproduce large-scale fermenters with regard to these process parameters.

(B) Overpressure Controller

There is a trend towards large-scale production facilities also in animal cell fermentation so that for the simulation of the different hydrostatic pressure conditions from industrial production scales a pressure control system up to 1000 mbar overpressure was developed for the stirred reactor with a steal vessel used in the present invention (10 L working volume, B. Braun, chapter 3.5.2). This reactor was meant to control defined set values independently from the controllers for pCO$_2$, pO$_2$ and pH value.

(1) Set-Up and Functionality

At the non-sterile side of the exhaust air line of the fermenter a pressure control valve (Brooks pressure controller, Model 5866 Series, 0-68 L·h$^{-1}$) was installed. The opening width was the actuating variable for the developed PID pressure controller in the process control system (LabView). The control variable was measured on the inside of the reactor lid by means of a gel filled pressure sensor and transferred to the process control system. Due to the rapid decrease in pressure even with small opening widths of the pressure control valve in contrast to the slow increase in pressure due to the low gassing rate with closed pressure control valve, it was not possible to control the control process within the required tolerance. Thus, in addition, a membrane valve was installed further down the exhaust air line in the direction of the exhaust analyser, whose valve position could be preset manually (FIG. 4).

The set-up developed in said manner, i.e. with an additional membrane valve, has the following advantages:
 safety margin: Maintenance of an adjustable minimum pressure in case of failure of the pressure control valve during operation
 sufficient inertia of the control process despite sub-optimum flow rate of the pressure control valve (maximum possible valve throughput 68 L·h$^{-1}$, maximum gassing rate 45 L·h$^{-1}$)

Due to the variable gassing rates necessary for $pCO_2$ control, installation and manual adjustment of the pressure by means of the membrane valve alone was not possible.

(2) Quality Control of Overpressure Control

Figure 5:
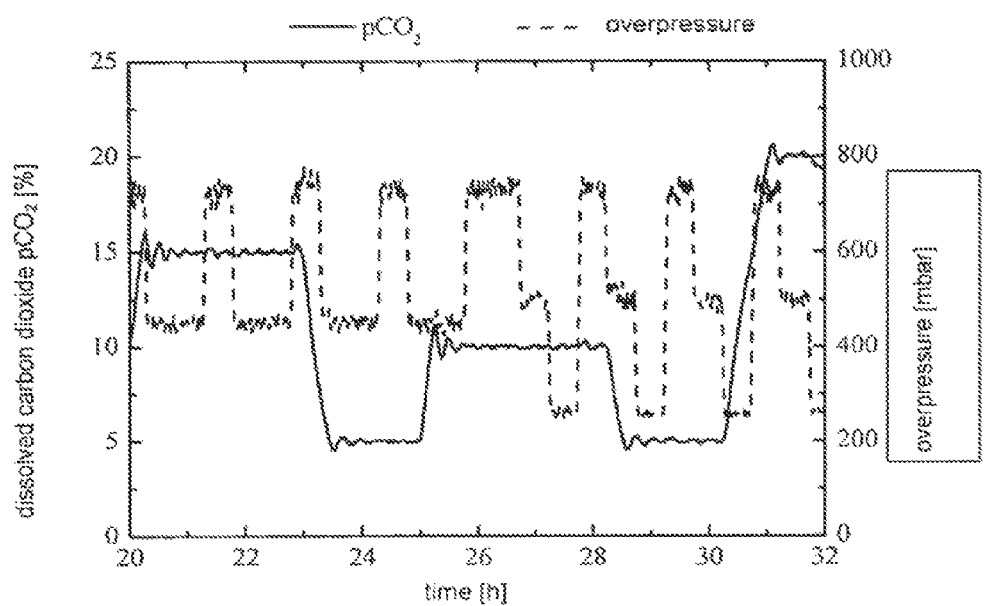

Control optimization was carried out according to Ziegler and Nichols (Rake, 1993). The operation capability of the overpressure control of a static set value with simultaneous control of $pCO_2$ set value profiles was furthermore complemented by an automated, process time dependent control of the set value. This allowed for the generation of defined overpressure profiles for, e.g., the simulation of mixture profiles prevailing in large-volume production fermenters. Due to mixing times of partly several minutes, the mixing profiles in these reactors deviate from the model of homogenously mixed reactors and according thereto different spatial positions of the suspended cells in the hydrostatic pressure profile. FIG. 5 shows an example of a time-dependent pressure profile in the 10 L stirring vessel based on a pressure profile of a production fermenter. At the same time a dynamic control of the $pCO_2$ set value is shown which can be carried out independently from the pressure profile adjusted.

The control of the intermittent set value of the reactor overpressure p (each for 30 min at 750 mbar and 1 h at 450 mbar) between the process times t=20 h and t=26 h shows a high quality of control (±30 mbar) without having significant effects on the control of the set value of the dissolved carbon dioxide concentration (<1% absolute) (FIG. 5). This is particularly important when considering the increasing solubility of the $CO_2$ in the case of increase in pressure. Likewise, changes of the $pCO_2$ set value do not show any changes of the quality of control of overpressure in the course of the process (FIG. 5) despite the fact that e.g. for decreasing the $pCO_2$ ratio in the fermenter medium by increased nitrogen flow, the total gas volume flow into the fermenter was increased by 50%. Set values between 1.5-25% $pCO_2$ with up to 1000 mbar overpressure could be adjusted and corrected in this set-up.

It was shown that it is possible to control oxygen, pressure and $pCO_2$ independently from one another and with high quality of control. Despite constant, low rotational speed of the stirrer the oxygen entry for animal cell cultures is sufficient. Due to appropriate control of the set value, the simulation of the enrichment of $CO_2$ is possible during the course of the process. Also, a profile for the simulation of changes in pressure due to hydrostatic effects in high production reactors can be adjusted. Thus, in total, it is possible that the existing requirements for the industrial process parameters considered can be implemented dynamically.

(C) pH Adjustment Agents

In the excess metabolism cultivated cell lines produce significant amounts of lactate and other organic acids which, together with the $CO_2$ discharged into the medium, lower the pH value of the culture medium in the course of the process. The effect of the pH value in the medium on the cell physiology and product quality (e.g. of secreted glycoproteins) has been examined sufficiently. Thus, in optimized processes, the pH value of the medium is adjusted in defined ranges, mostly between pH 6.6 and pH 7.4, by addition of different bases to the cultivated cell suspension. Common bases are NaOH, which is available for CIP (clean in place) processes in most validated production facilities, and $Na_2CO_3$ and/or $NaHCO_3$, which is a buffer component in most cell culture media. Often, $CO_2$ is mixed to the gassing air of cell culture processes in the starting phase to lower the pH value of the medium. In that way, even with media free of $NaHCO_3$ a balance is formed between the $CO_2$ added during gassing and the aqueous culture medium.

Negative effects of pH correction can occur in large-scale production facilities in the case of addition of strong bases via the head region. In this context, due to long mixing times of up to several minutes, pH gradients of up to 0.8 pH units between instillation site and pH measuring point were described (Langheinrich and Nienow, 1999). The settings of the pH controller also have great effects on cell density and induction of apoptosis in the culture vessel (Osman, Birch et al., 2001; Osman, Birch et al., 2002).

(1) Effect of the pH Adjustment Agent to a Cell-Free System

The basic pH adjustment agents NaOH and $Na_2CO_3$ were compared with different, simulated cell culture conditions but identical control settings (FIGS. 6 and 7). Their effect on cultivation of a CHO cell line in fed-batch processes is described in the following.

With identical pH control settings in Biostat ES, controlled 5% $pCO_2$ were adjusted in an aqueous phosphate/hydrogen carbonate buffer mixture in Biostat (30 L·h$^{-1}$, 37° C., 200 rpm, 750 mbar overpressure). The result was a pH initial value of 7.28. Then, due to a change in the set value in the process control system, a switch of $pCO_2$ from 5% $pCO_2$ to 15% $pCO_2$ was provoked and pH control was started simultaneously. For this purpose, the pH set value was adjusted to 7.2 with NaOH (1 M, FIG. 6) and/or $Na_2CO_3$ (1 M, FIG. 7). These test conditions simulated an accelerated enrichment of the $CO_2$ produced by the cells in the medium and the pH control with the corresponding base, which is directed against the acidification caused (FIGS. 6 and 7).

For pH control using NaOH, 2.6 h and 26 dosages were necessary for the change of the $pCO_2$ set value (FIG. 6). The resulting dosage frequency is 10 h$^{-1}$. For the pH control using $Na_2CO_3$, the $pCO_2$ setting time was reduced by 60% to 1.6 h (FIG. 7). The $CO_2$ additionally entered by the $Na_2CO_3$ causes reconcentration of the dissolved $CO_2$ parallel to the $pCO_2$ controller. In comparison to the NaOH, the dosage frequency (8 h$^{-1}$) is reduced. The tendency of reduced base consumption with use of $Na_2CO_3$ instead of NaOH is illustrated by means of the cumulative dosage profile in FIG. 8. For the $pCO_2$ set value change described, the double amount of 1 M NaOH is required for pH control. In total, 220 g 1 M NaOH (0.21 mol) in contrast to 110 g 1 M $Na_2CO_3$ (0.1 mol) were entered into the reactor (FIG. 8).

Thus, the entry of sodium ions is identical with both titration agents. Thus, a negative effect on the cell culture by potentially different osmotic effects due to use of the bases described can be excluded with $pCO_2$ control. Since the final conditions of both titration systems are identical due to the equilibrium conditions, the bases NaOH and $Na_2CO_3$ can have a different effect on the cultivated cells due to the following effects: number of dosages, frequency of dosages, disturbances of the $CO_2$ balance—extracellular & intracellular.

Osman et al. examined the effect of pH disturbances on the mouse myeloma cell line GS-NS0 in set cultures (Osman, Birch et al., 2002). For this purpose, they exposed the cells to pH increases to pH 8.0, several times sequentially, as they also occur by suboptimum mixing in production fermenters with addition of strong bases such as NaOH and/or $Na_2CO_3$ (Langheinrich and Nienow 1999). They found that with increasing number of pH deflections to pH 8.0 the cell viability decreases. Likewise, an increasing frequency of the bases addition to pH 9.0 decreased the cell viability significantly (Osman, Birch et al., 2002). Since with use of NaOH as pH adjustment agent in the present invention, both effects described by Osman et al. play a role (increase in dosage frequency and number of dosages), similarly negative effects on cultivated cells are to be expected. In contrast to the results achieved under the $pCO_2$-controlled conditions mentioned above, it has to be assumed that the negative effect of NaOH is significantly stronger on cell physiology if $pCO_2$ control is not used.

It is to be assumed that the strong disturbance of the $CO_2$ balance in the culture medium by titration with NaOH (prolonged $pCO_2$ adjustment time, compare FIGS. 6 and 7) can also have an effect on the cytosole of the cells present in the culture medium. This hypothesis is supported by the findings presented with the development of the pressure-controlled sampling apparatus and those shown in the following as to the effect of pH titration agents on cultivated animal cells on a small scale.

(2) Effect pH Adjustment Agents on Fed-Batch Cultivations of a CHO-K1 Cell Line at the 1 L Scale The above observations of effects of NaOH and $Na_2CO_3$ should be evaluated in fed-batch cultivations of the cell line CHO-MUC1 in small-scale fermenter systems (1 L Applikon). The small fermenter described was operated in the Fed Batch Modus with membrane gassing and overpressure to simulate the hydrostatic pressure effects of bigger reactors. The pressurizer unit (provided by Bioengineering) worked autonomously and the pressure was adjusted manually by means of a retention valve behind the exhaust filter. The pressure measurement took place on the sterile side with an adapter piece especially designed by means of a piezosensitive pressure sensor. During pre-fermentation of the cells in the reactor, an overpressure of 60 mbar was maintained to simulate small fermenters of industrial propagation. By means of partial harvesting of the fermenter volume, increasing the pressure to 150 mbar and use of a main fermentation medium, the main production process (100 L) was simulated. By means of feeding medium the glucose ratio was maintained above 1.0 g $L^{-1}$ and the glutamine ratio between 0.8 g $L^{-1}$ and 1.0 g $L^{-1}$.

In the following, the live cell densities and viabilities achieved in the course of the process are illustrated in the FIGS. 9 and 10 for different $CO_2$ profiles of the gassing mixture. The results illustrated in FIG. 9 were realised with a constant ratio of 5% (v/v) $CO_2$ in the gassing mixture. For manual pH control at pH 7.2, however, the $CO_2$ ratio in the gassing mixture was successively reduced for the fermentation illustrated in FIG. 10.

For both $CO_2$ gassing modes, higher viable cell densities, prolonged cultivation periods and higher product concentrations can be achieved when using $Na_2CO_3$ instead of NaOH (FIGS. 9 and 10). The lactate concentrations show a continuous increase over the whole course of process for both pH adjustment agents used (FIG. 11).

Therefore, the resulting cell-specific lactate formation rates are higher when NaOH is used as base than when $Na_2CO_3$ is used (calculated data not shown). When NaOH is used as adjustment agent, osmolalitites over the threshold of 400 mOsmol $kg^{-1}$ correlate with a slowing down of cell growth, when $Na_2CO_3$ is used, however, the cells continue to grow exponentially to enter the stationary growth phase at a later point in time (FIG. 12). High-osmolar processes, as described in the literature as to increase in productivity (Kim, Kim et al., 2002), can be further optimized by use of $Na_2CO_3$ instead of NaOH as pH adjustment agent, according to the results shown herein. Particularly in combination with the $pCO_2$ controller developed, processes of that kind can probably be further improved with regard to cell metabolism, cell physiology and product formation. On the basis of these results, $Na_2CO_3$ was used exclusively as pH adjustment agent for further cultivations in the present invention.

Example 3

Pressure-Controlled Sampling for Fermentation Accompanying Measurement of Cell-Physiological Parameters in Pressure Blanketing Fermentations of Animal Cells As already described above, industrial fermentations of animal cells are carried out on a large scale where, according to Henry's Law, hydrostatic pressure, in combination with sterilisation-related overpressure, causes increased solubility of gases contained in the culture medium. In particular, the solubility of carbon dioxide produced by the cells and released into the aqueous medium is approximately 25 times higher than that of oxygen under similar conditions (Bailey and Ollis, 1986). The related and easy-to-measure change of the pH value in the culture medium can be minimized by using suitable buffer systems and pH adjustment agents. Since $CO_2$ is a small unpolar molecule, it is capable to permeate the membrane of animal cells and, thus, influence the intracellular pH value (Thomas, 1995).

In general, cell-containing samples are collected in defined intervals from the culture for fermentation accompanying analysis. According to the state of the art, conventional sampling methods from fermentations with pressure blanketing, envisage opening a valve installed in the bottom region and releasing, due to the overpressure in the culture vessel, a defined volume of cell-containing sample without pressure into a suitable vessel. The related expansion of the cell suspension involves a time-dependent degasification of the suspension. The actual concentrations of dissolved gas in the corresponding fermenters may, consequently, be represented only insufficiently by the blood gas analyzers according to conventional sampling (see below).

The following Examples give results of studies on this matter which, in addition to the extracellular changes in the medium, feature on the effect of the sampling method on the intracellular pH value of the cells contained in the medium. The development of an apparatus for pressure-controlled sampling and the necessity to apply it with analysis of the intracellular pH value of animal cells, which accompanies cultivation in large-scale fermentation and/or fermentation with pressure blanketing, are presented.

(A) Construction and Development of a Pressure-Controlled Sampling Apparatus (1) Qualification by In Situ and Off-Line $pCO_2$ Measurements In order to examine the effect of different sampling methods on the concentrations of dissolved gas in the medium—according to the state of the art and using the apparatus developed—different concentrations of dissolved carbon dioxide and different pressures were set in the 10 L reactor Biostat ES to simulate the different conditions in industrial large-scale fermenters. For this purpose, the appropriate medium was gassed with defined carbon dioxide ratios in the gassing mixture under standard fermentation conditions (ratio gassing 30 L·h$^{-1}$, 37° C., 200 rpm) and otherwise the parameters indicated in Example 2(E). In this context, the pH value was not adjusted by the addition of a base. For the measurements, the $CO_2$ concentration increased by the increasing total pressure in the medium was in equilibrium with the gaseous phase (exhaust analysis. Xentra 4900, Servomex). FIG. 13 shows the parameters the combination of which led to the 30 experiments which were carried out.

The measurements of the dissolved carbon dioxide ratio were carried out using in situ $pCO_2$ probes (Yellow Springs Instruments, USA) and/or, subsequent to sampling, off-line using a blood gas analyzer (AVL Compact 3, Roche Diagnostics GmbH). FIG. 14 indicates exemplary results for 0.15 M NaCl as aqueous medium. From this, the relatively high loss of dissolved $CO_2$ between in situ measurement values and conventional sampling methods becomes clear ($\Delta pCO_2$=30%).

Figure 17:
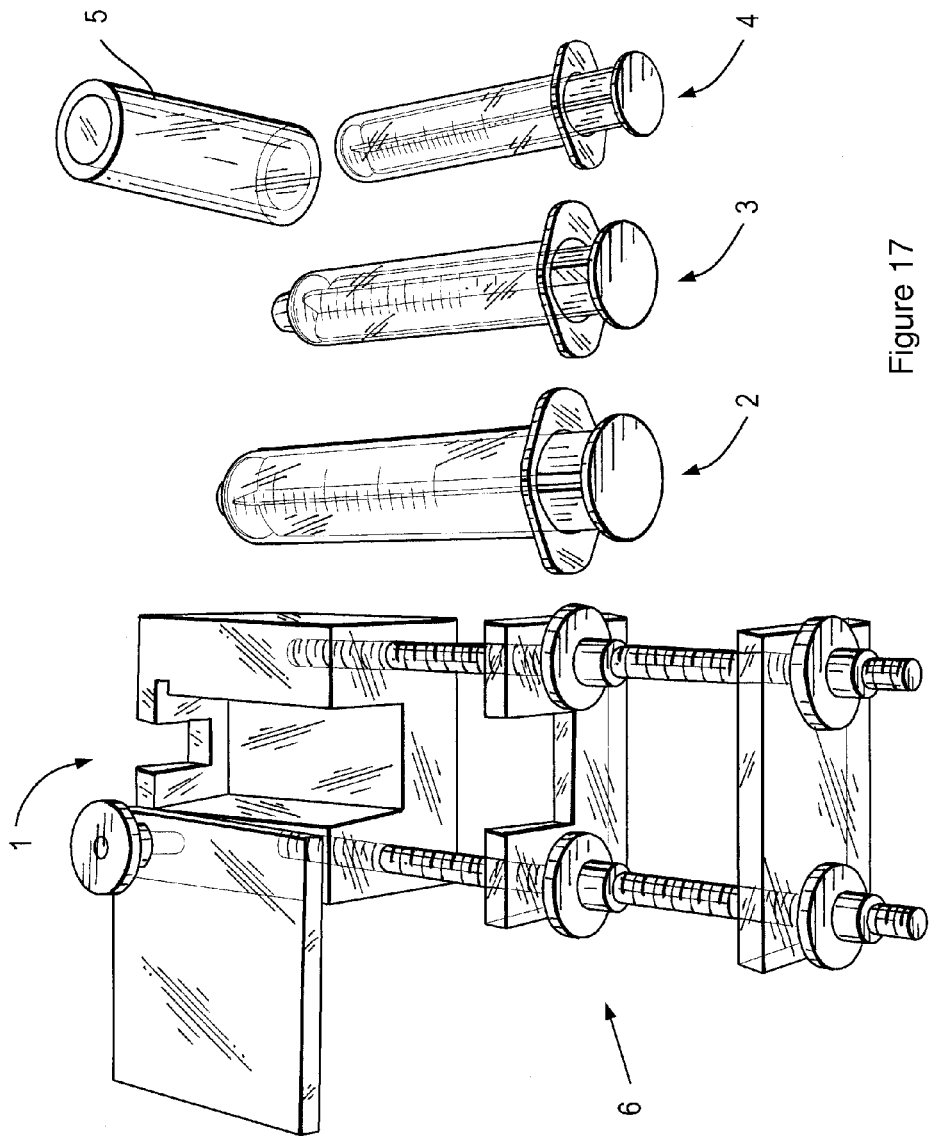

The smaller loss of $CO_2$ with use of the sealed syringe is to be attributed, primarily, to the lower degree of mixing with $CO_2$-free ambient air which inevitably occurs with conventional sampling. Sampling with the syringe is carried out by means of a sterile adapter which could be connected directly to the sampling valve of the reactor (FIG. 16). The internal pressure of the reactor moved the plunger installed in a gas-tight manner in the syringe fixed in a support against atmospheric pressure to the preset stop (FIGS. 17 and 18). Comparative results of this preferred sampling method with different reactor overpressures are shown in FIG. 15. Further reduction of $CO_2$ loss was pursued by modification of this sampling method.

The use of this syringe-based reactor sampling technique already allows to minimize the loss of dissolved gas concentration ($\Delta pCO_2$) from 30% to 20%.

The maintenance of the overpressure prevailing in the reactor at sampling time should further minimize the loss of dissolved gas. For continuous measurement of the sample pressure, a piezoelectric pressure receiver was integrated into the sampling line and connected to a digital display (FIG. 16).

Thus, pressure measurement was also possible after uncoupling the sampling unit from the reactor. Control of the sample pressure indicated on reactor level and, consequently, the isobaric collection of the sample was carried out manually by slowly releasing the (cell-)suspension from the pressure-blanketed fermenter into the sampling unit connected thereto (FIG. 16). The knurled screws installed allowed fine-tuning of the sample pressure subsequent to uncoupling the unit from the reactor (FIG. 16-18). The pressure-controlled sampling apparatus (DNP) developed in this way maintained the dissolved gas concentrations in the cell-free sample on reactor level over a period of several hours (Klinger, 2006). FIGS. 17 and 18 show a photography of the support unit for different sample volumes which were obtained using syringes and adapter sleeves and a top-view of the support unit with installed syringe.

At this stage of the development, due to the sterile construction, it was possible to use and qualify the specifically developed DPN for sampling in pressure-blanketed fermentations of animal cells. The sterile couplings (Stäubli, Switzerland) in combination with the steam-sterilisable sampling valve of the bioreactor, the sterile mode of operation of the stirring vessel was not limited (qualifications not shown).

Figure 19:
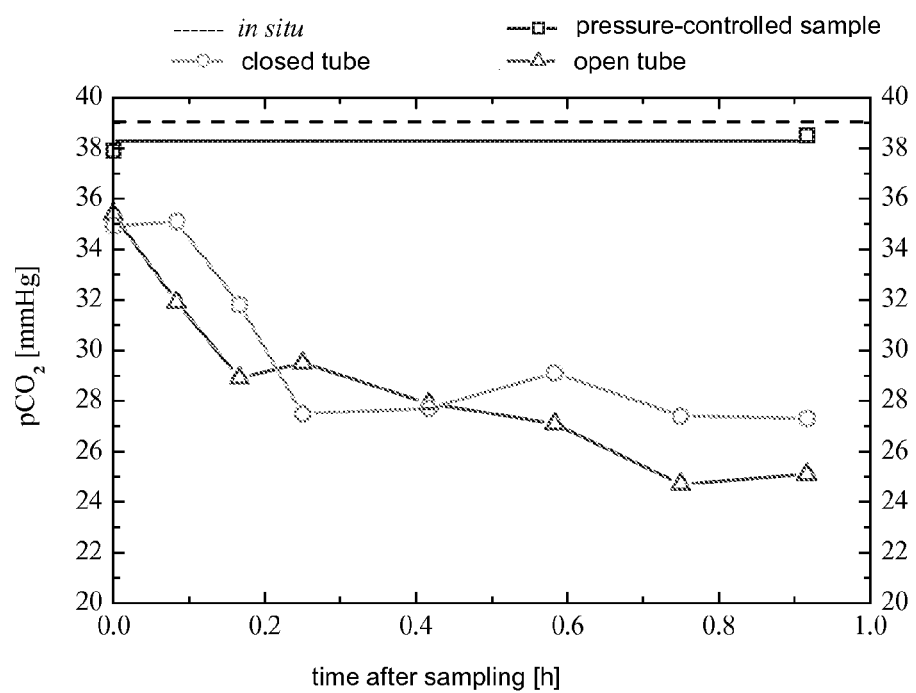

FIG. 19 shows in an exemplary manner, the $CO_2$ concentration measured off-line according to conventional sampling method in comparison with the pressure-controlled sampling method developed at termination of a pressure-blanketed fed-batch cultivation of the CHO-MUC1 cell line. Even though the dissolved carbon dioxide concentrations do not significantly differ in the different vessels immediately after sampling, the concentration of dissolved $CO_2$ in the conventional sampling methods decreases by 20% during the first 12 minutes already. Thus, if conventional sampling techniques are applied, a representative measurement of dissolved $CO_2$ in fermentations with pressure blanketing is only possible with immediate measurement by means of a blood gas analyzer.

The use of the sampling apparatus developed, while maintaining reactor pressure and reactor temperature, is an essential advantage. The sampling apparatus maintains the initial reactor concentration of dissolved $CO_2$ over a storage period of one hour (FIG. 19). In this context, the concentration of dissolved oxygen was not limiting at any time (Klinger, 2006). Due to fact that the pressure and $pCO_2$ concentrations of the reactor are maintained outside the reactor, the pressure-controlled sampling apparatus developed allows medium-term sample treatment (<1 h) under bioreactor conditions.

In particular, the period of time analysed in FIG. 19 is suited in an optimum manner for the treatment of cell-containing sample with a fluorescence dye as, for example, it is required for the measurement of the intracellular pH value. The fundamental correlations between the $pCO_2$ level in the culture medium and the intracellular pH value are shown in Example 4, the results of $pCO_2$-controlled fermentation obtained using the sampling apparatus as described herein are given in Examples 5 to 7.

In the following, exemplary results of flow cytometric studies on cell physiological qualifications of the different sampling methods are presented.

(2) Qualification by Means of Flow Cytometric Measurements

Maintaining the reactor conditions (temperature, pH value, components of the medium, concentrations of dissolved gas, pressure) was considered only to some extent by the flow cytometric determination of the intracellular pH value using conventional protocols according to the state of the art. Little attention was paid, in particular, to the sampling from pressure-blanketed fermentations and the associated degasification of the medium and their effect on the physiology of the cells contained in the sample. From the following Examples, it becomes clear that, even though the extracellular measurement values pH and $CO_2$ show no detectable changes in the medium after sampling, the cells suspended in the medium can already differ significantly with respect to the physiological conditions in the bioreactor.

By using the developed sampling apparatus in flow cytometric determinations, it is possible to measure intracellular pH values which represent the physiological state of the examined cells in the bioreactor essentially better than it is possible in the state of the art. The following FIGS. 20 and 21 show results from flow cytometric $pH_i$ measurements which were achieved without (FIG. 20) and with pressure-controlled sampling (FIG. 21), respectively. In the partial illustrations 2 and 3, to the right of the respective Figure, the intensities of the corresponding fluorescences (FL2-H AND FL3-H, respectively) are plotted against the cell size. The partial illustrations 1, on the left, show the ratio peak resulting from the ratios of fluorescence intensities FL3/FL2. This ratio determines the $pH_i$ value according to the calibration values. Its value is determined by the number of counts per detection channel.

In order to determine the $pH_i$ value of a CHO cell population in the pressure-blanketed fermenter according to the state of the art, first, a sample was collected in a sterile manner under decompression to atmospheric pressure and then incubated with the fluorescence dye SNARF-1 for 25 minutes as described above. The subsequent measurement in the flow cytometer showed the fluorescence intensity ratios shown in FIGS. 20 A and B. In FIG. 20 A1, a double-peak can be observed which is based on two cell populations with different fluorescence intensities (FIG. 20 A2 and A3). Despite the selection of suitable boundaries for the individual peaks (FIG. 20 B, upper populations), it is not possible to relate the peaks unequivocally to the initial $pH_i$ value of the population in the reactor.

Upon observation of the same sample after a period of 50 minutes (FIG. 2-20 C), the fluorescence of the cell population has completely shifted causing due to its homogeneity a single peak of the corresponding fluorescence intensity ratio (FIG. 20 C1). This single peak represents the final state of a time-dependent change of the fluorescent cell population for which, temporarily, a double population can be observed as shown in FIG. 20 A.

This assumption was to be confirmed by using the pressure-controlled sampling for the incubation of the reactor sample, which was obtained in an isobaric manner, with the fluorescence dye SNARF-1. If the partial populations with high fluorescence intensity (scatter diagrams in FIG. 20 A2, A3) and the position of the corresponding ratio peaks (FIG. 20 A1) after isobaric incubation in the pressure-controlled sampling apparatus are compared with those from incubation without pressure according to conventional sampling (scatter diagram in FIG. 21 D2 and D3 and ratio peak FIG. 20 D1), the following differences can be observed. Contrary to incubation without pressure (according to the state of the art), even after 25 minutes of incubation, a homogenous fluorescent cell population (FIG. 21 D2 and D3) and a corresponding single ratio peak (FIG. 21 D1) can be observed. If the same sample is incubated for further 25 minutes without overpressure, the whole fluorescent cell population is shifted analogously to the one without pressure (cf. FIG. 21 E2 and E3; FIG. 21 C2 and C3). The final positions of the single peaks are identical (cf. FIG. 21 E1 and FIG. 20 C1) after a period of 50 minutes, but they do not reflect the real $pH_i$ of the cell population in the reactor.

This supports the theory that, during incubation without pressure under expansion, cell populations from the reactor are subjected to a time-dependent $pH_i$ change which can be measured by means of the inhomogeneous shift of the fluorescence populations and the transient ratio double-peak. These intracellular changes can be measured before extracellular parameter such as pH and $pCO_2$ may cause significant changes of the measurement values and, thus, may falsify the measurement of the intracellular pH value of the cell population in pressure-blanketed fermenters considerably.

Al-Rubeai (Welsh and Al-Rubeai, 1996) attributed the time-dependent sub-peak (FIG. 20 A1, left peak) occurring due to (intracellular) degasification to the non-viable cell population. Thus, according to their studies, there is a striking correlation between the ratio of non-viable cells and the cell populations which are represented by an analogous sub-peak. This is not confirmed by the results presented herein. In fact, the cell populations used for the above-mentioned studies exhibited viabilities >95% and were in the exponential growth phase without limitations. Early apoptotic signals which coincide with an acidification of the cytosol can be excluded as cause for the ratio double-peak shown herein (FIG. 20, A1 left peak). According to this, with respect to the bioprocess, they would imply that the pressure variations observed with conventional sampling induced severe apoptosis analogously to e.g. the repetitive (fed-)batch processes, which, however, cannot be observed. The ratio double-peak as observed herein is transient and, thus, it is to be attributed only to sampling and/or incubation without pressure and the resulting degasification of the cells in suspension.

In fact, in the present invention, ratio double-peaks were also observed with the use of the pressure-controlled sampling apparatus, but only at the end of (fed-)batch cultivations when measurable decreases in viability can be registered (data not shown). These coincide with late phases of the apoptosis which were measured by parallely applied flow cytometry by means of DNA quantification (sub-G1 peak with cell cycle analysis using DNA fragments).

Thus, the results shown herein support the necessity of isobaric sampling with pressure-blanketed fermentations in order to correctly determine the intracellular pH values of the reactor population.

Example 4

Effects of the Content of the Dissolved Carbon Dioxide on the Intracellular pH Value of Animal Cells As a small unpolar molecule, physically dissolved $CO_2$, a product of metabolism of cultivated cells, can permeate the cell membrane relatively unhindered without requiring specific transporters (Thomas, 1995). However, within the cell and in the extracellular aqueous medium, it is in equilibrium with hydrogen carbonate for which active transports systems are provided to the cell (Hu, Seth et al., 2007). Thus, a change in the concentration of one of the species always causes a corresponding change of the other species involved in the equilibrium and, consequently, a change of the pH value. If changes in the concentration of dissolved $CO_2$ and/or hydrogen carbonate occur in the culture medium of the cells, this has always time-dependent effects on the intracellular pH value ($pH_i$) of the cells. The maintenance of the physiological medium and, thus, the intracellular processes is carried out by the cell via regulation of the $pH_i$ by using transporters in the cell membrane, in part, under energy-consumption conditions (Madshus, 1988; Reusch, 1995).

In the following, the correlation between the $pCO_2$ content of the culture medium and the $pH_i$ of the cells cultured therein is studied. The CHO-MUC1 cell line was cultured with controlled $pCO_2$ values in the reactor system (chemostat, 1 L), a sample was collected under maintenance of the reactor conditions and, for the determination of the $pH_i$, incubated with the pH-sensitive fluorescence dye according to the experiment in question. The concentrations of the $pCO_2$ in the sample were determined off-line (AVL Compact 3) and the intracellular pH value was measured by means of flow cytometry.

(A) In Vitro Effects of $pCO_2$ on $pH_i$

The $pCO_2$ saturation to the corresponding $pCO_2$ levels in the medium were achieved by gassing the stained cell suspension with air (AVL Compact 3) immediately (<5 s) before the flow cytometric $pH_i$ measurement. The effects on the intracellular pH value due to different $pCO_2$ saturations in the culture medium in vitro are shown in FIG. 22. The parallel graphs of the curves obtained from different reactor samples are indicative for a direct correlation between $pCO_2$ concentrations in the medium enclosing the cells and the intracellular pH value of the cells. The higher the $CO_2$ saturation in the culture medium, the higher was the temporary alkalization of the cytosol of the cells contained in the culture medium.

The observed phenomenon of the short-term intracellular alkalization with depletion of dissolved $CO_2$ in the culture medium can be attributed to the shift of its equilibrium. If the $CO_2$ which is physically dissolved in the medium and is in equilibrium with hydrogen carbonate and protons is removed, this will cause an increase in the pH value since the binding of hydrogen carbonate to hydronium ions will increase to replace the dispersing $CO_2$ with elimination of water. This equilibrium shift takes place in the cytosol so that with decreasing $pCO_2$ concentration in the medium, the measured $pH_i$ value increases as shown in FIG. 22. In the following, this short-time effect is referred to as "chemical effect" of the changes of the content of dissolved $CO_2$ on the intracellular pH value.

As the following studies show, a viable cell actively reacts to this change in its environment. On a deflection from the physiological equilibrium state, as upon the removal of dissolved $CO_2$ from the culture medium shown in FIG. 22, in addition to the short-term chemical effect described, the cells always exhibit a reaction in form of a "physiological effect" (FIG. 23). A biphasic development of the $pH_i$ could be observed in all experiments (FIGS. 23 and 24). In this context, the short-time alkalization of the cytosol due to $CO_2$ depletion was always followed by a phase of acidification of the cytosol, which is contrary to the shift of the $CO_2$ equilibrium. Only 30 to 40 minutes after in vitro $CO_2$ depletion in the medium, the intracellular pH value of the population dropped below the initial value (FIGS. 23 and 24). In this context, no significant changes of the extracellular pH value are measured in the cell culture medium used (FIG. 23), whereas the intracellular pH value shows the above-described biphasic change, with the extracellular pH value being constant.

This super-compensation of $pH_i$ deflection could be observed with different initial $pCO_2$ values (FIG. 24), wherein the $pCO_2$ gradient between the initial concentration in the culture medium and the final value after $CO_2$ depletion determines the degree of the intracellular alkalization via the "chemical effect" (FIG. 24).

The super-compensation with an acidification below the initial value if the intracellular pH, which was observed in the second phase, can be correlated with active transport processes through the cell membrane. As already discussed above, there are several relevant transporters in CHO cells which are responsible for $pH_i$ control. They adjust the intracellular pH value by means of a flow equilibrium prior to a dissolved $CO_2$ disturbance. This phenomenon will be further discussed in the following Example where the in situ effects of $CO_2$ enrichment in the culture medium on the cytosolic pH value will be examined.

(B) In Situ Effects of $pCO_2$ on $pH_i$

The observed in vitro effects of the time-dependent cell response on $CO_2$ depletion in the culture medium (FIGS. 23 and 24) were to be simulated in situ in the controlled small-scale fermentation system (Applikon 1 L). For this purpose, the set value profile of $pCO_2$ was raised gradually during a continuous chemostat cultivation. In FIG. 25, the resulting $pH_i$ values are plotted for the viable cell density in relation to process time.

As can be seen from FIG. 25, the above, in vitro observed, effects of the short-time alkalization and the long-time acidification of the cytosol after a decrease of the $pCO_2$ level in the culture medium also occur in situ with, in contrast, an escalated enrichment of the culture medium in the small-scale fermenter. In this context, corresponding short-time acidification and long-time alkalization can be observed as reactions of the cell to the escalated increase in dissolved $CO_2$ concentrations in the medium. It must be noted that the long-time alkalizations of the cells after the $pCO_2$ surge to a higher value (FIG. 25) remain at this level (+0.1 $pH_i$ units per surge from 2.5% to 5.0% and from 5.0% to 10.0% $pCO_2$, respectively, in the medium). Thus, the intracellular pH value seems to be directly correlated with the $pCO_2$ level of the culture medium, since, apart from this parameter, the cultivation conditions are constant in the chemostat process. Thus, there is the possibility to influence the $pH_i$ of the cells, with the described consequences regarding physiology and metabolism, via the $pCO_2$ concentration in the culture medium.

To date, only incomplete studies on this subject matter have been described in the literature. These examined continuous processes regarding the influence of $pCO_2$ on animal cells, however, they were based on methods using cell retention which could not ensure a constant cell population (size distribution, cell cycle phase distribution, metabolic consumption and formation rates). Phenomena which can be generally observed are the alkalization of the cytosol with accelerated cell growth and generally intensified metabolism and/or a more acidic $pH_i$ with resting cells (Engasser, Marc et al., 1996; Welsh and Al-Rubeai, 1996). In combination with the $pCO_2$ controller developed, the chemostat process as studied herein with a cell output over the complete size distribution and with constant cell density provides, for the first time, the possibility of detailed cell physiological and metabolic studies of the cells in equilibrium state. Thus, it is possible to decouple the effects of the $pCO_2$ content in the medium on $pH_i$ from the changes which, due to cell growth and cell cycle phase distribution, occur e.g. in batch processing or in processing with cell retention and associated size selection.

In the early 1990s, Wu et al. already began to work on single-cell-based computer simulation of the intracellular pH control in CHO cells (Wu, 1993). The "regular model" for cell growth in suspended batch cultures postulated by Wu describes $pH_i$ values for states of equilibrium and alkaline depletions in CHO cells in a satisfying manner, however, the description requires modifications with respect to the $pH_i$ after transient acidification of the cells. The modifications indicated by the authors in this context describe the property of CHO cells allowing activating the $NA^+/H^+$-antiporter with acute acidification of the cytosol and reducing the activity of said antiporter to a basal level once a new equilibrium is achieved even if the cytosolic pH is still more acidic than the initial pH. The above-mentioned findings from the pH- and $pCO_2$-controlled chemostat process are contrary to the modifications of the $pH_i$ regulation model of Wu. The effect described by Wu shows high similarity to the "chemical effect", which would be a possible explanation for short-time pHi changes in such simulations. However, once a new in situ equilibrium state is reached in the controlled system, the "physiological effect" prevails with super-compensation by active transport processes and also by activating the $NA^+/H^+$-antiporters, as postulated by Wu. This "physiological effect" in dynamic situation models of animal cells should be considered in an appropriate manner.

Example 5

$pCO_2$-Controlled Fed-Batch Cultivation of Cell Line CHO-MUC1 in 10 L-Scale

The findings obtained in the above Examples on the basis of the effect of the different pH adjustment agents, the reactions of the intracellular pH value to the $pCO_2$ in vitro and in situ and the procedural implementation of the control strategies for $pCO_2$ and overpressure will be consolidated in the following. For this purpose, the bioreactor Biostat ES was used with the model cell line CHO-MUC1 under industrial conditions (overpressure, $pCO_2$ profiles, medium, processing mode). Subsequent to revitalisation in spinner flasks, the inoculum was cultivated in a working volume of up to 1 liter at 5% $CO_2$ in the incubator. Subsequent to inoculation, the viable cell density in the 10 L reactor was $1.5 \times 10^5$ cells $mL^{-1}$. All further fermentations in 10 L-scale were carried out under standard fermentation conditions as described in Example 1(E) with constant energy transfer. Foaming was counteracted by manually adding an anti-foaming agent (Dow Medical Grade C). The overpressure in the fermenter was adjusted to 750 mbar, the $pCO_2$ values to constant 5%, 15%, 25% and/or a profile of 5-15% $pCO_2$, respectively. The dynamic set value profile of 5-15% $pCO_2$ was intended to simulate $CO_2$ enrichment in the culture medium during the fermentation process in industrial production processes. According to the relevant literature, 25% $pCO_2$ should have a deleterious $CO_2$ effect on the cultivated cells (Kimura and Miller, 1996; Pattison, Swamy et al., 2000; de Zingotita, 2002).

In all cultivations, the concentrations of the control substrates glucose and glutamine was maintained in the range of between 2-5 $L^{-1}$ and 0.5-1.0 g $L^{-1}$, respectively, by daily pulsed feed, so that amino acid eliminations were prevented. The abort criterion for the fermentation was a viability below 80% in order not to detect erroneously the incompletely translated fusion protein or fusion protein affected by proteases of the cell in ELISA.

(A) Growth Behaviour

Figure 26:
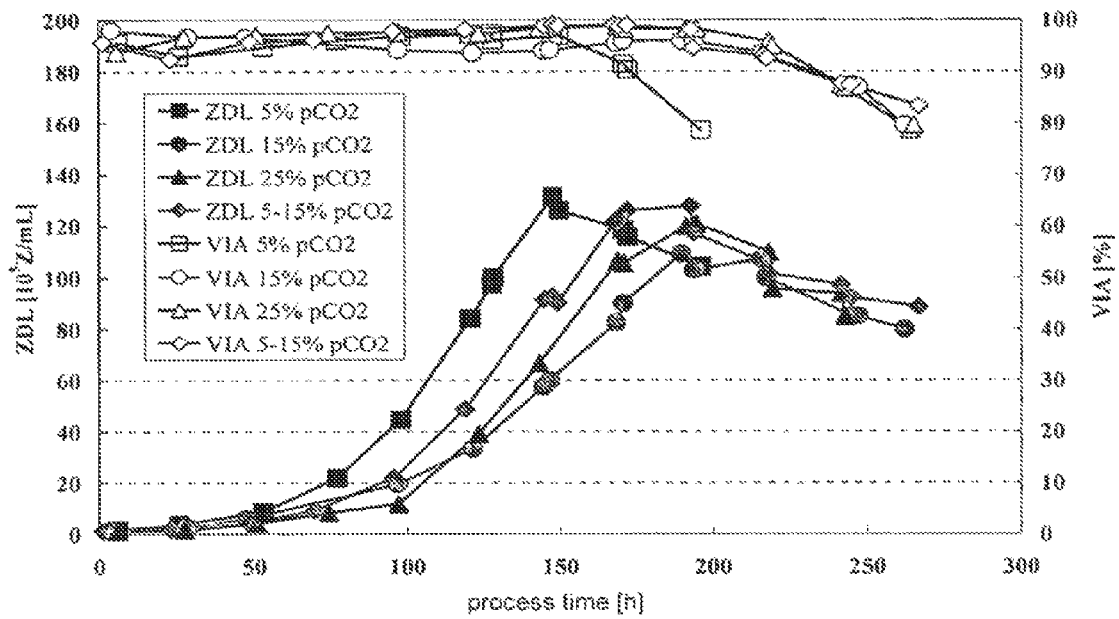

FIG. 26 shows growth behaviour and viabilities for the different $pCO_2$ control profiles. From this, the following tendency becomes apparent. In general, the cultures in the bioreactor grew more rapidly at lower $pCO_2$ values if these were adjusted to constant set values. At 5% $pCO_2$, the maximum density of viable cell achieved is highest ($1.3 \times 10^7$ $mL^{-1}$) and in minimum time (150 h). In this case, viability decreases comparatively early so that the duration of cultivation is significantly shortened (<200 h). Cultivation with a $pCO_2$ profile simulating the course of growth in an industrial fermenter on production scale shows a striking course of growth (see also FIG. 28 showing $pH_i$). In this case, the $pCO_2$ value is from 5% (start) to 15% (190 h and more) and the related growth curve is between the curves of controlled constant 5% and 15% $pCO_2$ (FIG. 26). At 25% $pCO_2$, the culture shows slower growth, but exhibits higher viable cell densities than the culture at 15% $pCO_2$. Thus, no toxic effect is observed at 25% $pCO_2$ yet, a further increase in $pCO_2$ was not possible due to technical factors. Viability curves and death rates are similar for all controlled constant $pCO_2$ values (FIG. 26).

(B) Cell Cycle Phase Distribution

In the following, the cell cycle curves of the G0G1 phase fractions of cultivations with different $pCO_2$ set value profiles are studied (FIG. 27). In this context, the relatively high G0G1 fraction at 15% $pCO_2$ is to be noted which increases from 150 h onward until cultivation is stopped and, thus, reflects a progressing cell arrestation.

The curve of the G0G1 phase fractions for cultivation with a $pCO_2$ profile of 5-15% is, up to 150 h, analogous to the curve for cultivation that is $pCO_2$-controlled at constant 5%. Thus, this curve is similar to the curve for 15% $pCO_2$. This industrial $pCO_2$ profile shows, however, a particularly distinct turning point at approximately 170 h with the G0G1 fraction decreasing. This correlates with a $pCO_2$ value of 13% (FIG. 28). A further increase in the $pCO_2$ value to 15% and its fixation at this level does not result in a further increase in the G0G1 phase fraction (FIG. 28). However, in the process which is adjusted to constant 15% $pCO_2$ since cultivation start, the G0G1 phase fraction further increases until the end of the process (FIG. 27).

(1) Consequences for Process Development

It remains to be examined whether, in this case, a higher G0G1 phase fraction could be achieved by means of static control of the set value at 13% (turning point G0G1 phase fraction) with the start of cultivation. Thus, a dynamic $pCO_2$ set value profile—as applied herein or similar—is useful for cell (line)-specific $pCO_2$ optimization, e.g. by applying the turning point method as shown herein to the curve of cell cycle distributions or other cell parameters (e.g. $pH_i$, specific rates). Contrary to the profile of industrial large-scale fermenters which is to be simulated, the $pCO_2$ set value profile as shown herein is applied externally via the control by means of $CO_2$ addition via gassing. In industrial production fermenters, $CO_2$ enriched in the medium is provided by the cells themselves. Therefore, it is possible that a corresponding $pH_i$ profile can differ accordingly. This might also be analysed analogously if the pressure-controlled sampling apparatus developed in the present invention is used.

(C) Intracellular pH Value

Since is has been shown that the $pH_i$ value can be influenced by applying the strategy of $pCO_2$ control, this should also affect cell cycle phase distribution. FIG. 29 shows the G0G1 fractions and $pH_i$ values for the process with controlled constant 25% $pCO_2$ as a comparison. An acidification process in the cytosol can be observed which coincides with the turning point in the G0G1 phase fraction curve (200 h). Thus, turning points in the $pH_i$ curve of the studied CHO-K1 cell line coincide with turning points in the curve of the G0G1 cell cycle.

In this context, the cell is exposed to a constant $pCO_2$ value in its environment throughout the whole cultivation process. The $pH_i$ value increases continuously until it reaches a value of 7.35 and, at the turning point of the G0G1 phase fraction curve, continuously decreases until it reaches pH 7.0. A short-time alkalization prior to the decrease of viability and termination of cultivation can also be observed.

In general, at a $pCO_2$ of this high level, the G0G1 fraction is similarly high at the beginning of cultivation (FIG. 27) which is reflected by the slow growth behaviour. Throughout the whole fermentation process, the G0G1 phase fraction is within a small range (50-60% G0G1 fraction).

Since intracellular enzyme activities also show pH dependencies, influencing the intracellular pH by means of $pCO_2$ and the corresponding control strategy is an important process parameter which is to be optimized. Bresnahan and Dittmer correlated, for example, increased specific antibody productivities with increased intracellular pH and cell cycle arrestation, respectively, in the late G1 phase (Bresnahan, Boldogh et al., 1996; Dittmer and Mocarski, 1997). The controller developed in this invention, for the first time, allows to study the decoupling of the $pCO_2$ level from the pH value of the culture medium and osmolality.

The correlations between $pCO_2$ with central cell metabolism will be examined in the following.

(D) Glutamine and Glutamate Metabolism

With increasing $pCO_2$, the glutamine uptake rate is slightly increased, this becomes particularly manifest at 25% $pCO_2$ (FIG. 30). Similar starting curves for specific glutamine uptake rates can be observed for 5% $pCO_2$ and 5-15% $pCO_2$ as already observed with the G0G1 phase fraction (FIG. 27).

Based on the yield coefficients for glutamate versus glutamine illustrated in FIG. 31, it is possible to assume that, in processes with high values of constant controlled $pCO_2$, the increased glutamine uptake contributes to the formation of glutamate to a lower degree. Y(GLT/GLN) which indicate the correlation between formed glutamate GLT with consumed glutamine GLN are, on average, lower with the constant $pCO_2$ control value increasing and, furthermore, show different progression curves. With progressing process, a continuous increase of the yield coefficient at a high level can be observed at 5% $pCO_2$, whereas, at 25% $pCO_2$, only a slight increase can be observed at a similarly low level. At 15% $pCO_2$, the process shows a more constant yield coefficient with a slight tendency to decrease throughout the process. With an increasing $pCO_2$ set value profile (5-15%), however, the curve of the corresponding yield coefficient is irregular. The local maximum of the yield coefficient at 170 h coincides with the turning point identified before for the G0G1 phase fraction (compare FIG. 31 and FIG. 28).

(E) Lactate Metabolism

The cell-specific lactate formation rates show the characteristics as depicted in FIG. 32 resulting in cumulative lactate concentration curves as depicted in FIG. 33. In this context, the cell-specific curve at 25% $pCO_2$ has to be noticed which shows an increase in the exponential growth phase (70 h-120 h) and again at the end of cultivation (>200 h). The other fermentations examined, in general, show a decrease with respect to the cell-specific lactate formation rate with progressing cultivation. The fermentation at 15% $pCO_2$ shows the highest specific lactate formation in the stationary growth phase.

(F) Product Formation

The product formations for the processes which are regulated to controlled constant $pCO_2$ values of 5% and 25% $pCO_2$ do not show any differences in their progression except with respect to the final antibody concentration MUC1-IgG, which is caused by the varying process durations. The substantially higher productivity of the process which was regulated to an increasing $pCO_2$ set value profile (FIG. 34), is significant.

(G) Consequences for Process Development

Thus, in general, with $pCO_2$ adjustment to controlled constant $pCO_2$ levels, it is possible to enhance process robustness under the conditions as shown herein. According to the results as shown herein, the adjusted $pCO_2$ set value profiles, in particular, have potential for cell line specific optimization. Thus, it was possible to increase productivity, under as constant conditions as possible, (e.g. energy transfer, overpressure, temperature, pH value) by increasing the $pCO_2$ profile. With regard to different industry-related issues, the $pCO_2$ control as well as the overpressure control developed were simultaneously and successfully used in the 10 L bioreactor in fed-batch processes. The results obtained by $pCO_2$ control show high potential for the optimization of industrial cell cultivation processes by controlling the following parameters: intracellular pH value, cell cycle distribution, central metabolism (e.g. glucose, lactate, glutamine, glutamate), apoptosis/duration of cultivation.

Example 6

Chemostat Culture of Cell Line CHO-MUC1-IgG: $pCO_2$ Set Value Control with Glucose Limitation and "Metabolic Shift"

The differences recognized in the central carbon metabolism caused by the different $pCO_2$ set value profiles were studied in greater detail in the chemostat process (1 L).

In the 1 L bioreactor described in Example 1(E), the recombinant CHO-K1 cell line CHO-MUC1-IgG was cultivated in the chemostat process. For this purpose, gassing was carried out by means of an L-shaped gassing tube (Applikon) which introduced the gassing mixture with constant volume flow into the medium below the propeller stirrer (2.4 $Lh^{-1}$). In this context, the cell suspension was removed from the near bottom region by means of an immersion nozzle in order to continuously add fresh medium via the head region so that the reactor volume was maintained constant. The corresponding flow rates D and growth rates p are shown in FIG. 35, viable cell density was within flow equilibrium at 7.5 ($\pm$1)$\times 10^6$ $mL^{-1}$.

In the batch phase (<120 h) the substrate glucose is consumed and the culture is delivered to the metabolic switch in order to initiate lactate remetabolisation. In this phase, glutamine is sufficiently available as an alternative carbon source, there were no amino acid limitations. Subsequent to a gradual increase in flow rate D with an increasing number of viable cells, pH control was started at 230 h (from pH 6.6 to pH 7.0 using 1M $Na_2CO_3$). Thus, the lactate remetabolisation prevailing up to then was stopped and an increased lactate formation occurred.

In the glucose-limited chemostat process, the cell-specific lactate formation rates decreased during the process. However, the growth rate remained equal to the flow rate (FIG. 35). If there is a set value surge from controlled 10% $pCO_2$ to 20% $pCO_2$ (420 h) in this flow equilibrium, the cell-specific lactate formation rate triples during the following 150 h and the glutamine uptake decreases (FIG. 36). At this position of the gradients between internal and external pH value, on the basis of the findings of the present invention, it is possible to influence the $pH_i$ and, thus, directly influence lactate transport and metabolism via an optimized $pCO_2$ control (also in combination with pH set value control in the culture medium).

Example 7

$pCO_2$ Controlled Fed-Batch Cultivations of Cell Line CHO-hGM-CSF-PYC2 on a 1 L-Scale As proven in the present invention so far, apart from the pH value of the culture medium, also $pCO_2$ and $pCO_2$ set value control affect the central metabolism significantly, even under glucose-limited conditions. Furthermore, exact knowledge of the intracellular pH value is essential for a metabolically and energetically optimized cell culture process. Since in particular the metabolic switch for lactate remetabolisation may enable efficient metabolic pathways with an associated increase in productivity in recombinant cell lines, high process robustness desirable for industrial processes. Therefore, in the experiments described herein, the combination of the $pCO_2$ process engineering developed herein should be carried out using a CHO cell line which is optimized via metabolic engineering and $pCO_2$-sensitive at the same time. Consequently, a sensitive alignment of the control strategies in the fermenter with the desired cell metabolism is required. In this context, the energy transfer must also be taken into account. In this study, the parameter of the empty tube velocity of gas was selected for $pCO_2$ control and regulation. However, if the stirrer interferes also with the control cascade for $pO_2$ and $pCO_2$, the effect of energy transfer has to be studied in an analogous approach according to the experimental set-up shown herein. In studies of this kind, the procedural parameter always have to be considered separately from the effect of the composition of the culture media.

Since direct effects of $pCO_2$ control on lactate metabolism could be identified, a cell line optimized with regard to lactate metabolism by means of metabolic engineering is used herein. The cell line CHO-hGM-CSF-PYC2 has a pyruvate carboxilase with cytosolic activity affecting also the central metabolism (Wagner, 1998; Irani, 1999; Bollati Fogolin, 2001; Bollati Fogolin, 2003) (FIG. 37). $pCO_2$ control should allow, for the first time, to purposefully change the hydrogen carbonate concentration in the cell and, thus, the concentration of a substrate of pyruvate carboxylase via the $pCO_2$ level in the medium and thus influence the central metabolism.

Subsequently, the effect of different controlled $pCO_2$ concentrations on parameters such as cell physiology and cell metabolism as well as on intracellular pH and productivity was to be studied on a 1 L-scale using the fed-batch fermentation of cell line CHO-hGM-CSF-PYC2 which secretes the growth factor hGM-CSF into the medium. Constant cultivation conditions which are analogous to the 10 L-scale allow to compare the results with the results obtained for the antibody producing cell line CHO-MUC1. The pyruvate carboxylase from *S. cerevisiae* which exhibits cytosolic activity in this recombinant cell line and which catalyses the anaplerotic reaction of pyruvate with hydrogen carbonate into oxalacetate allows the metabolic exploitation of hydrogen carbonate, which is present in the cytosol, by the cell via the citric acid cycle (FIG. 37*b*).

According to the analysis of the metabolic flows in BHK-PYC cells expressing the recombinant cytosolic pyruvate carboxilase (Paul, 2006), the flow of the recombinant cytolsolic pyruvate carboxylase was very low under the process conditions examined in this context. Consequently, a dependency on $pCO_2$ concentration and a $pH_i$ dependency of this metabolic pathway caused by said concentration dependency were to be studied. This approach was considered purposeful since the hydrogen carbonate concentration is an important parameter for the reaction of cytosolic pyruvate into oxalacetate and since, according to the results obtained herein, it should be possible to influence hydrogen carbonate concentration via the (controlled) $pCO_2$ level in the culture medium (and, thus, also in the cytosol). It is also conceivable to influence the newly introduced metabolic pathway in the model cell line CHO-hGM-CSF-PYC2 via the secondary parameter $pH_i$—which, also according to the results shown herein, can be influenced by the $pCO_2$ level—, for example, via the pH dependency of pyruvate carboxylase activity and lactate dehydrogenase activity.

(A) Process Conditions

Dependency of the cellular parameters on the controlled $pCO_2$ level was studied. The inoculum was cultivated at 5% $CO_2$ in the incubator as described above. All inoculum cultures used had viabilities higher than 95%. In the 1 L stirred reactor, standard fermentation conditions were used (Example 1(E)). Glucose concentration was maintained in the range of 2-5 gL$^{-1}$ by adding a sterile bolus (maximum 5% v/v; 1-2d$^{-1}$) of a concentrated feed solution. This allowed to prevent both, glucose limitation and the Crabtree effect (also: negative Pasteur effect) which occurs with a glucose concentration of approximately 10 gL$^{-1}$ and higher. Accordingly, the glutamine concentration was maintained between 0.5-1.0 gL$^{-1}$ and amino acid limitations were avoided. Throughout the entire cultivation process, $pCO_2$ values were controlled to be constant 5% $pCO_2$ and 15% $pCO_2$, respectively. A cultivation with uncontrolled $pCO_2$ concentration was run as reference (FIG. 38). Here, pH set value deflections of the culture medium were counteracted by adjusted admixture of $CO_2$ in the gassing air as well as by controlled addition of sodium carbonate solution (1 M). With this $CO_2$-based pH control, the increased formation of acidic metabolites (e.g. lactate) during the cultivation process results in a reduction of the $CO_2$ ratio in the supply air but it may cause a decrease of the $pCO_2$ concentration in the medium below physiological concentrations (<5%). This reduction can already be observed with the set-up with constant gassing rate as used herein (FIG. 38) and is probably further increased upon successive increase in the gassing rate which is used in order to increase the oxygen transfer into the culture medium.

(B) Viable Cell Densities and Viability

Figure 39:
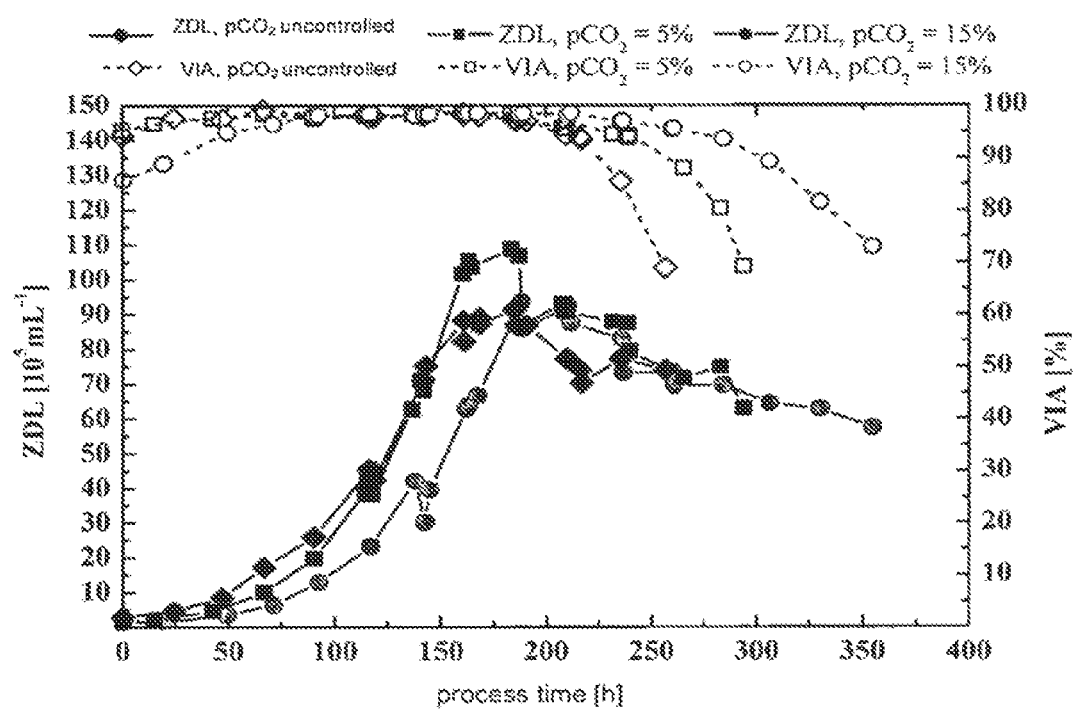

Viable cell densities and viabilities are shown in FIG. 39. In this context, the following tendencies can be observed. All cultures reach the stationary growth phase after approximately the same time span (170 h; 7 days). For the different $pCO_2$ profiles, the maximum viable cell densities do not differ significantly (9-11×10$^6$ mL$^{-1}$). The later entry into the stationary phase with controlled $pCO_2$ of 15% may be caused by the initially lower viability of the culture subsequent to inoculation of the stirring vessel. Possibly, the transition of the cells from the pre-cultivation at 5% $CO_2$ into the culture medium equilibrated at 15% $CO_2$ in the reactor first has a negative effect on the viability. Effects of these $pCO_2$ surges on the cells were studied in Example 4. It proved that, in comparison with the process according to the state of the art in which $pCO_2$ is not controlled, the control of $pCO_2$ concentrations throughout the whole fermentation process has a positive effect on the viability of the cultures and allows an extended stationary phase of high cell density. The higher the controlled $pCO_2$ value, the longer the culture is viable. The optimum for the recombinant CHO-K1 cell line studied is closer to 15% $pCO_2$ than to 5% $pCO_2$.

(C) Addition of Base and Osmolalities

Figure 40:
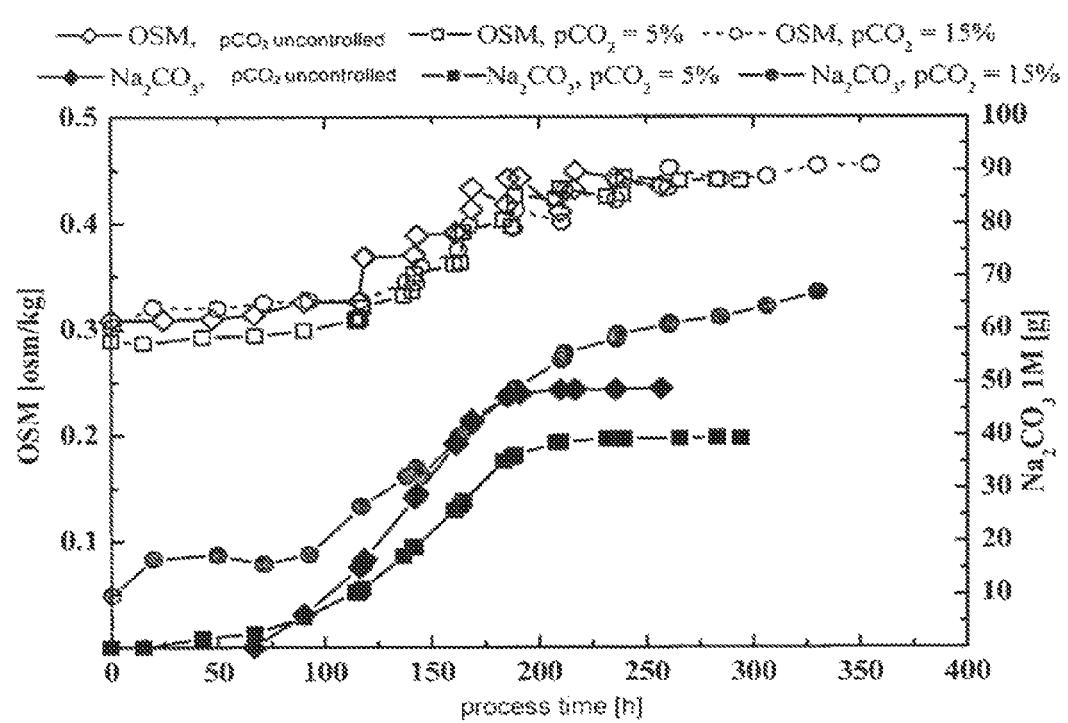

The adjustment of the initial controlled $pCO_2$ value upon inoculation was carried out with simultaneous control of the pH value. Thus, the pH value decrease due to the $CO_2$ added for high $pCO_2$ values was counteracted by the addition of sodium carbonate solution. This caused a higher initial addition of base into the fermenter at 15% $pCO_2$ as can be seen in FIG. 40. However, the process without $pCO_2$ control initially does not require any base since the acidification of the medium can first be counteracted by a reduction of the $CO_2$ ratio in the supply air (FIG. 40). Whereas the addition of base at controlled 5% $pCO_2$ and controlled 15% $pCO_2$ is identical for the intervals of the process time 80-180 h (parallel curves), the addition of base in processes with uncontrolled $pCO_2$ is greatly increased during this time. Thus, only the process at 15% $pCO_2$ requires a base until the process is terminated (FIG. 40), implying that the metabolism of the cultivated cells is still active. The final osmolalities of all described processes are, however, identical and show an analogous curve throughout the process period (FIG. 40). The extended process duration due to higher viabilities is, thus, not coupled to osmolality, but has to be primarily attributed to the controlled $pCO_2$ level.

(D) Lactate Metabolism

Also with the lactate formation of the different processes, graduation can be observed (FIG. 41). The non-controlled $pCO_2$ process forms more lactate from the start of the process already and achieves, compared to the other processes, a higher concentration maximum. Subsequently, there is the controlled 5% $pCO_2$ process involving decreasing lactate accumulation, followed by the controlled 15% $pCO_2$ process.

Independently from the controlled glucose and glutamine concentrations, respectively, which were all maintained between 2.0 to 5.0 gL$^{-1}$ and 0.5 to 1.0 gL$^{-1}$, respectively, over the entire fed-batch process (data not shown), in the processes with uncontrolled $pCO_2$ and with controlled 5% $pCO_2$ a lactate metabolisation with entry into the stationary phase can be observed (from 180 h and 220 h, respectively, FIG. 42). This diauxy behaviour is not very distinct in the controlled 15% $pCO_2$ process. Its cell-specific lactate formation rate is in the positive range over the entire course of cultivation (FIG. 42), however, the lactate accumulation in this process is the lowest (FIG. 41).

These observations allow for the following conclusions: In the studied fed-batch process, the cell line CHO-hGM-CSF- PYC2 used showed lower maximum lactate concentrations with controlled $pCO_2$ values (reduction by 30% with 15% $pCO_2$ compared to non-controlled $pCO_2$ process). The remetabolisation of lactate observed with entry into the stationary phase is more distinct with higher lactate concentrations. This change in metabolism is not coupled to a limitation of glucose or glutamine. The central metabolism, in this case lactate formation serves as an example, can thus be influenced by control of $pCO_2$. In this recombinant cell system with cytosolic pyruvate carboxylase, an increase in metabolic efficiency can be achieved by increase in $pCO_2$ in the culture medium (preferably carried out by an appropriate control and regulation, as shown herein).

(E) Product Formation

The specific product formation rate differs with different, controlled $pCO_2$ values significantly (FIG. 43). In comparison with the uncontrolled $pCO_2$ process, the specific product formation rates are strongly increased with continuously controlled $pCO_2$: for the controlled 15% $pCO_2$ process compared to the controlled 5% $pCO_2$ process by 15% on average (FIG. 43). Thus, by control of $pCO_2$ up to constant 15% $pCO_2$, the increased specific product formation rate and the extended process duration result in a maximisation of the hGM-CSF product titre by 100% in the case of the cell line CHO-hGM-CSF-PYC2 used (FIG. 44).

(F) $pH_i$ Cell Cycle Phase Distribution and Specific Productivity

In the following, the cause of the increased productivity with increased controlled $pCO_2$ concentrations was to be analysed. For this purpose, the intracellular pH curves, specific productivities and selected cell cycle phase distributions of the individual fermentations with different $pCO_2$ profiles were contrasted.

In Example 4 it was clearly shown which effects $pCO_2$ has on $pH_i$. Thus, $pCO_2$ jumps in the culture medium of the processes always cause a biphasic change of the intracellular pH value. In the following figures (FIG. 45-47), the curves of the intracellular pH value (before pulsed feed), the specific productivities and the ratios of the percentages of cells in the S-phase and cells in the G0G1 phase (S/G0G1) are shown.

In the fed-batch cultivation with uncontrolled $pCO_2$ (FIG. 45), the first feeding coincides with the decrease of the $pH_i$ by 0.3 units. With entry into the stationary growth phase, the $pH_i$ increases again. In comparison with the controlled $pCO_2$ processes, the SPR remains extremely low. The $pH_i$ also remains on an extremely low level ($pH_i$<7.1) during the entire cultivation.

With the 5% controlled $pCO_2$ culture (FIG. 46), the $pH_i$ decreases, independently from the entry into the stationary growth phase, due to the first feeding by approximately 0.3 units. The entry into the stationary growth phase coincides with an increase in the $pH_i$ by 0.5 units. The SPR also strongly increases in the stationary growth phase. In total, the $pH_i$ is on a higher level than with the uncontrolled $pCO_2$ culture (FIG. 45), however, it fluctuates more than with the 15% controlled $pCO_2$ process (FIG. 47). Furthermore, the increase in the S/(G0G1) ratio at the end of the stationary growth phase shows an incomplete arrestation of the cell cycle.

With the controlled 15% $pCO_2$ culture (FIG. 47), after the first feeding, the $pH_i$ does not decrease—contrary to the cultivations with uncontrolled and controlled 5% $pCO_2$, respectively. Even after entry into the stationary growth phase, the $pH_i$ only decreases slightly and for a short period. On the whole, with controlled 15% $pCO_2$, this cultivation shows the lowest variations of the $pH_i$ values and, moreover, the highest $pH_i$ level in the course of cultivation. Furthermore, in this context, a constant low cell cycle phase fraction S/(G0G1) can be observed from approximately 200 h, which corresponds to a successful arrestation of the cell cycle (FIG. 47). The thus extended viable culture period in combination with the increasing SPR during the stationary growth phase results in the highest end product titre in this cultivation series (FIG. 44).

In summary, the cell-specific productivities with the cell cycle phase fractions of the cells in the G0G1 phase are shown for the processes with different $pCO_2$ profiles in FIG. 48.

Accordingly, the following results can be summarised for the described fermentations with different $pCO_2$ profiles for the cell line CHO-hGM-CSF-PYC2 analysed: An increasing $pH_i$ correlates with the increased G0G1 phase fraction of cultivated cells. An increased G0G1 phase fraction correlates with an increase in the cell-specific productivity. The higher the controlled $pCO_2$ set value during the course of the process, the higher is the phase fraction G0G1 in the stationary growth phase.

The increase in the specific productivity by arrestation of cells in the G0/G1 phase is described in the literature. A three-fold higher specific production formation rate was observed e.g. with use of AMP (adenosine monophosphate), since the cells during the exponential growth phase were arrested and, thus, transferred into a long stationary phase.

The process strategy of $pCO_2$ control as pursued herein results for CHO-hGM-CSF-PYC2 in a product concentration which is 10-fold higher (at controlled 15% $pCO_2$) than with the strategy based on temperature decrease by Bollati et al. (Bollati Fogolin, 2003). According to the findings obtained therein, it can be assumed that also in the latter case solubility of $CO_2$ in the culture medium was increased due to the temperature decrease and, thus, may have played a role in the increased productivity via an extended process duration and an extended G0/G1 phase. Similar effects due to temperature decrease have already been described (Bloemkolk, 1992; Moore, 1997; Kaufmann, 1999). Even tough, contrary to the batch method, in the fed-batch method used, limitations of the substrate can of course be avoided and an extended process duration can be achieved, increased, controlled $pCO_2$ is a basic factor for higher specific product formation rates. This increase is probably related to the increased solubility of $CO_2$ in the culture medium.

(G) Cell Respiration

In combination with pH control, measurement and control of $pCO_2$ in the culture medium developed in the present invention an enrichment of $CO_2$ in the liquid phase was counteracted (Example 2). Thus, it became possible to balance $CO_2$ by means of supply and exhaust air. The correlation of the oxygen uptake rate (OUR) with the carbon dioxide evolution rate (CER) results in the respiratory quotient (RQ). A complete respiration of glucose into $CO_2$ would result in RQ=1. An RQ value >1 would only occur with fermentation, lipid or protein anabolism, whereas an RQ value <1 is an indicator for incomplete oxidation of amino acids and for protein and lipid catabolism (Hauser and Wagner, 1997; Alberts, 2002).

As described in Example 1, the oxygen transfer rate OTR can be calculated based on the $k_L a$ value. This value was determined cell-free under standard pressure in culture medium using the reconcentration method under standard fermentation conditions in both reactors. For the 1 L reactor used under atmospheric pressure, $k_L a_{O2}=3.55$ $h^{-1}$. Using the diffusivities of the gases oxygen and carbon dioxide via the proportionality factor 0.89 (Frahm, Blank et al., 2002), the value for this reactor is $k_L a_{CO2}=3.16$ $h^{-1}$.

The OUR was calculated using the flow volume of oxygen in the supply air. The partial pressure of oxygen in the reactor was measured online by means of an oxygen sensor. Based on the $pO_2$ value, the concentration of oxygen dissolved was calculated using the Henry constant for oxygen at 37° C. Based on the oxygen concentration in the supply air, the theoretical saturation concentration c* was calculated. This allowed to calculate the OTR value. In a stationary controlled state, OTR is equal to OUR and CTR is equal to CER, respectively.

In analogy to OUR, CER can be calculated on the basis of the measurement of the exhaust air. FIGS. 49 and 50 show the OUR, CER and RQ values for the $pCO_2$ controlled processes. After reaching a maximum value, the RQ value shows a substantially more rapid decrease at 5% $pCO_2$ than in the controlled 15% $pCO_2$ process. After a process time of 300 h, the RQ value of the process at 5% $pCO_2$ is merely a third of the RQ value at 15% $pCO_2$. The metabolism of this comparatively more productive process with controlled 15% $pCO_2$ is more oxidative throughout the whole process duration than the metabolism of the process with controlled 5% $pCO_2$.

Due to the comparatively high gas volume flows, the low cell consumption and production rates allow no balancing with respect to the differences in concentrations in supply and exhaust air. In this respect, the RQ calculations presented herein have some disadvantages in comparison with calculations described for microbial cultivations. Nonetheless, the RQ calculations demonstrate the potential of $pCO_2$ control to determine the parameter RQ in real time during fermentations also in animal cell cultivation processes. This would allow RQ parameter based process control in industrial high cell density processes via $pCO_2$ and, consequently, via purposeful adjustment of $pH_i$ with the above-mentioned optimization potentials.

The product formation occurs essentially in the G0G1 phase of the cell line studied. The higher the controlled $pCO_2$, the higher is the number of cells remaining in this phase. Thus, the higher viability of cells at a higher controlled $pCO_2$ implies that cells remain longer in the G0G1 phase with an increased $pCO_2$.

(H) Apoptosis

It was studied whether a higher controlled $pCO_2$ level has an anti-apoptotic effect on the cell culture. The 5-phase $pH_i$ curve is a common characteristic of all cultivations described above, which is clear from FIGS. 45 to 47. It is highly probably that, in all cultivations, the last turning point of the $pH_i$ curve marks the beginning apoptosis. In this context, the cell alkalinizes intracellularly before viabilities decrease below 80%, which was the criterion for stopping all cultivations. In the flow cytometric measurements of cell cycle which accompanied cultivation, a higher number of DNA fragments was also detected as sub-G1-peak after this late $pH_i$ turning point (data not shown) which in general can be observed in late phases of apoptosis (budding).

(I) Consequences for Process Development

Figure 45:
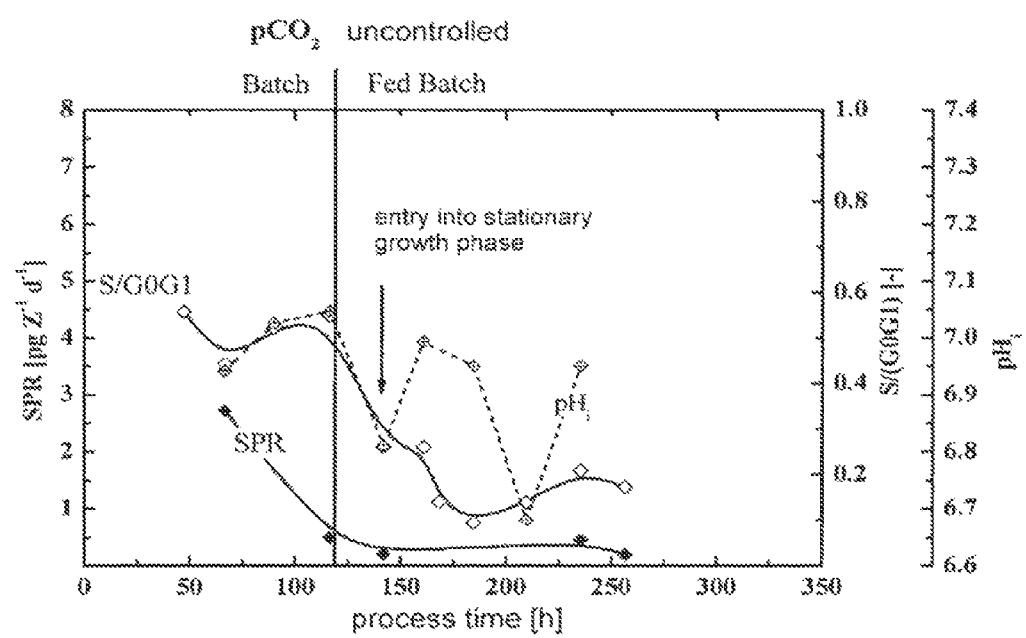

With uncontrolled $pCO_2$ or $pCO_2$ controlled at a low level (5%), pulsed feeds can have unfavourable effects on the intracellular pH value (FIG. 45-47). Apart from this feed technique, the pharmaceutical industry uses continuous feed throughout the whole fed-batch process in analogous processes. If $pCO_2$ is not controlled to maintain a relatively constant and/or high level, respectively (see above), this is a possibility not to provoke uncontrolled $pH_i$ oscillations based on the results shown herein to begin with. It would, however, be possible to purposefully achieve the same effect on the pHi of cells and, thus, on their physiology and metabolism by combining pulsed and continuous feed, which would have to optimized, preferably in combination with $pCO_2$-controlled cultivation. A strategy adapted to the process phases of growth and production might be rationally optimized on the basis of the findings of the present invention. Due to the high intracellular buffer capacity by $HCO_3^-$, a high (controlled) $pCO_2$ content in the medium causes lower environment-dependent $pH_i$ oscillations.

ABBREVIATIONS

| Abbreviation | Explanation |
|---|---|
| ATCC | American Type Culture Collection |
| BA | butyric acid |
| BGA | blood gas analyzer |
| BHK | baby hamster kidney |
| BSA | bovine serum albumin |
| CA | carboanhydrase |
| CD | chemically defined |
| CER | $CO_2$ evolution rate |
| CHO | Chinese hamster ovary |
| CIP | clean-in-place |
| CMV | cytomegalovirus |
| CTR | $CO_2$ transfer rate |
| DMSO | dimethyl sulfoxide |
| DNA | deoxyribonucleic acid |
| DPN | pressure-controlled sampling apparatus |
| E. coli | Escherichia coli |
| ELISA | enzyme-linked immunosorbent assay |
| FACS | fluorescence-assisted cell sorting |
| FBS | fetal bovine serum |
| FL | fluorescent light |
| FSC | forward scatter |
| G418 | genicitin |
| GFP | green fluorescent protein |
| GLC | glucose |
| GLN | glutamine |
| GLT | glutamate |
| HDFSB | dialysed FBS in HEPES buffer |
| HEPES | N-[2-hydroxyethyl]piperazine-N'-[2-ethanesulfonic acid] |
| hGM-CSF | human granulocyte-macrophage colony-stimulating factor |
| HPLC | high performance liquid chromatography |
| HPTS | hydroxypyrene-3-sulfonic acid |
| HRP | horseradish peroxidase |
| HTS | high throughput screening |
| IgG | immunoglobulin |
| LAC | lactate |
| LGH | lactate dehydrogenase |
| MCB | master cell bank |
| MFC | mass flow controller |
| MUC1 | mucin glycoprotein |
| NAD | nicotinamide adenine dinucleotide |
| NHE | sodium/proton exchanger |
| OPA | ortho-phthaldialdehyde |
| OPD | 1,2-phenylenediamine dihydrochloride |
| OSM | osmolality |
| OTR | oxygen transfer rate |
| OUR | oxygen uptake rate |
| PBS | phosphate buffered saline |
| $pH_i$ | intracellular pH |
| pNPP | p-nitrophenol phosphate |
| PRO | product |
| PYC | pyruvate carboxylase |
| RNA | ribonucleic acid |
| RP | reverse phase |
| rpm | revolutions per minute |
| RQ | respiratory quotient |
| RZA | space-time yield |
| SNARF-1 | 5'(and 6')-carboxy-10-dimethylamino-3-hydroxyspiro[7H-benzo[c]xanthene-7,1'(3'H)-isobenzofuran]-3'one |
| SSC | sideward scatter |
| TCA | tricarboxilic acid cycle, citric acid cycle, citrate cycle |
| TMA | trimethylamine |
| tPA | tissue plasminogene activator |
| VIA | viability |

| Abbreviation | Explanation |
|---|---|
| WCB | working cell bank |
| WTR | growth rate |
| ZDG | total cell density |
| ZDL | viable cell density |

REFERENCES

Alberts, B. J. et al. (2002). *Molecular Biology of the cell*, Garland Science.
Bailey, J. and D. 011 is (1986). *Biochemical Engineering Fundamentals*, McGraw-Hill.
BD_Biosciences (2000) Manual Part Number 11-11032-01.
Bell S L, et al. (1995) Enzyme Microb Technol 17: 98
Bloemkolk, J. et al. (1992) *Biotechnol Bioeng* 40:427-431.
Bollati Fogolin, M., et al. (2002) *Electron. J. Biotechnol.*
Bollati Fogolin, et al. (2001) Proceeding of the 17th ESACT Meeting, Tylösand, Kluwer Academic Publishers, Dordrecht, The Netherlands.
Bollati Fogolin, M., et al. (2003) *J. Biotechnol.* 109 (2004): 179-191.
Bond, J. and J. Varley (2005). *Cytometry* Part A (64A): 43-50.
Bresnahan, W. A., et al. (1996) *Virology* 224: 150-160.
Büntemeyer, H. (1988) Entwicklung eines Perfusionsprozesses zur kontinuierlichen Kultivierung tierischer Zellen in Suspension. Hannover, Universität Hannover.
Büntemeyer, H., et al. (1991). *Cytotechnol.* 5: 57-67.
Chen, K., et al. (2001) Biotechnol. Bioeng. 72:55
Cherlet, M., et al. (1999) *Biotechnol Prog* 15(4): 630-9.
Chow, S. and D. Hedley (1997) *Current Protocols in Flow Cytometry*, 9.3.1-9.3.10, John Wiley & Sons, Inc.
Chow, S., et al. (1996) *Cytometry* 24(4): 360-7.
deZengotita, V. M., et al. (2002) *Biotechnol. Bioeng.* 77(4): 369-380.
Dittmer, D. and E. S. Mocarski (1997) *J. Virol.* 71: 1629-1634.
Engasser, J. M., et al. (1996) *Flow cytometry applications in cell culture*. M. Al-Rubeai and A. N. Emery. New York, Marcel Dekker.
Etcheverrigaray, M., (1998) *Animal Cell Technology: New Developments, New Applications*. J. B. Griffiths, Merten, O. W. (Ed.), Kluwer Academic Publishers, Dordrecht, The Netherlands.
Frahm, B., et al. (2002) *J Biotechnol* 99(2): 133-48.
Givan, A. L. (1992). *Flow Cytometry: First Principles* New York, Wiley-Liss.
Grinstein, S., et al. (1989). *Biochim. Biophys. Acta* 988: 73-97.
Hauser, H. and R. Wagner (1997) *J Biotechnol* 59(1-2): 103-115.
Hu, W. S., et al. (2007) An advanced course in cellular bioprocess technology—Fundamentals and frontiers. Garmisch-Partenkirchen.
Irani, N., et al. (1999). *Biotechnol. Bioeng.* 66: 238-246.
Jockwer, A., et al. (2005) *Pressurisable sampling device for representative measurement of dissolved gases in large-scale fermentation processes*. Vortrag Bioperspectives 2005, Wiesbaden.
Jockwer, A., et al. (2005) DE 10 2005 020 985.8-41.
Kaufmann, H. M., (1999) *Biotechnol Bioeng* 3: 573-582.
Kim, M. S., et al. (2002) *In Vitro Cell. Dev. Biol. Animal* 38: 314-319.
Kimura, R. M. et al. (1996) *Biotechnol Bioeng* 52(1): 152-160.
Klinger, C. (2006) Diplom Thesis. Weihenstephan, University of Applied Sciences Weihenstephan.
Langheinrich, C. (1999) *Biotechnol. Bioeng.* 66(3).
Lim, C. K. (1987). HPLC of small molecules—a practical approach. Oxford, IRL Press, Oxford.
Link, T. (2003) Thesis Mathematisch-Naturwissenschaftliche Fakultät. Bonn, Rheinische Friedrich-Wilhelms-Universität Bonn.
Link, T. et al. (2004) Journal of Biotechnology 110: 51-62
Madshus, I. H. (1988) *Biochem. J.* 250:1-8.
Melamed, M: R. (1990). *Flow Cytometry and Sorting* New York, Wiley-Liss.
Moore, A. M., et al. (1997) *Cytotechnology* 23: 47-54.
Osman, J. J., et al. (2001) *Biotechnol Bioeng* 75(1): 63-73.
Osman, J. J., et al. (2002) *Biotechnol Bioeng* 79(4): 398-407.
Owen, C. S. (1991). *Anal. Biochem.* 204: 65-71.
Owen, C. S., et al. (1992) *J. Fluorescence* 2(2): 75-80.
Parker, C. (1990) *Methods Enzymol.* 182: 700-718.
Paredes C, et al. (1999) Cytotechnology 30: 85
Pattison, R. N., et al. (2000) *Biotechnol Prog* 16: 769-774.
Rake, H. (1993) Umdruck zur Vorlesung Regelungstechnik A and Ergänzungen (Regelungstechnik B). Aachen, RWTH Aachen.
Reusch, H. P., et al. (1995) *Am. J. Physiol.* 268: C147-C153.
Schmelzer, A. E., et al. (2000) *Biotechnol Bioeng* 67(2): 189-96.
Shapiro, H. (1994) *Practical Flow Cytometry*. 3rd ed. New York, Alan R. Liss.
Stucka, R., et al. (1991) *Mol. Gen. Genet.* 229: 307-315.
Thomas, J. A., et al. (1979) *Biochemistry* 18: 2210-2218.
Thomas, R. (1995) *Nature* 374(6523): 597-598.
Wagner, R., et al. (1998) Process for the improvement of the primary energy metabolism of mammalian cell lines
Welsh, J. P. and M. Al-Rubeai (1996) in *Flow Cytometry: Application in cell culture*. M. E. Al-Rubeai, A. N. New York, Marcel Dekker Inc.: 163-175.
Wu, P., et al. (1993) *Biotechnol Prog* 9(4): 374-84.
Wurm, F. M. (2004) *Nature Biotechnology* 22: 553-558.
Zhangi, J. A., et al. (1999) *Biotechnol Bioeng* 65: 182-191.
"DNA Sequences in Chromosomes II and VII Code for Pyruvate Carboxylase Isoenzymes in *Saccharomyces Cerevisiae*: Analysis of Pyruvate Carboxylase-Deficient Strains", Stucka et al., Mol Gen Genet 229, pp. 307-315, 1991.

The invention claimed is:

1. A method for the recombinant production of a polypeptide in a eukaryotic host cell modified in the citrate cycle to express a cytosolic pyruvate carboxylase, the method comprising the following steps:
   (a) cultivating the eukaryotic host cell in a suitable medium under conditions which allow the expression of the polypeptide, wherein the content of dissolved $CO_2$ in the medium is maintained at a constant value in the range of 10% to 20% of the saturated solution of $CO_2$ under a given set of conditions, and wherein a base is added to adjust the pH of the medium; and
   (b) recovering the polypeptide from the cell or from the medium.

2. The method of claim 1, wherein the host cell is an animal cell.

3. The method of claim 2, wherein the animal cell is a mammalian cell.

4. The method of claim 3, wherein the mammalian cell is a CHO, BHK, hybridoma or myeloma cell.

5. The method of claim 1, wherein the host cell modified in the citrate cycle is a cell which expresses a cytosolic pyruvate carboxylase.

6. The method of claim 1, wherein the polypeptide is a fusion protein, an antibody or a fragment thereof, an interferon, cytokine or growth factor.

7. The method of claim 1, wherein the content of dissolved $CO_2$ in the medium is maintained at a constant value in the range of 12.5% to 17.5% of the saturated solution of $CO_2$ under a given set of conditions.

8. The method of claim 1, characterized in that it is carried out as a fed-batch method.

9. The method of claim 1, wherein the content of dissolved $CO_2$ in the medium is maintained constant by means of a control system with a cascaded $pCO_2$-controller via mass flow controllers (MFC).

10. The method of claim 9, wherein any increase in the content of dissolved $CO_2$ in the medium is first reduced by decreasing a $CO_2$ ratio in a supply air, and if the $CO_2$ ratio in the supply air is reduced to zero, and the content of dissolved $CO_2$ still exceeds a set value, then the cascaded controller delivers an additional amount of $N_2$.

11. The method of claim 1, wherein the host cell is an insect cell.

12. The method of claim 1, wherein the base is $Na_2CO_3$.

13. The method of claim 1, wherein the content of dissolved $CO_2$ in the medium is maintained at a constant value of 15%.

* * * * *

UNITED STATES PATENT AND TRADEMARK OFFICE
CERTIFICATE OF CORRECTION

PATENT NO. : 8,460,895 B2  Page 1 of 1
APPLICATION NO. : 12/920915
DATED : June 11, 2013
INVENTOR(S) : Eisenkraetzer et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 150 days.

Signed and Sealed this
Eighth Day of September, 2015

Michelle K. Lee
*Director of the United States Patent and Trademark Office*